US010023628B2

United States Patent
(12) United States Patent
Low et al.

(10) Patent No.: US 10,023,628 B2
(45) Date of Patent: Jul. 17, 2018

(54) CELL LINE EXPRESSING SINGLE CHAIN FACTOR VIII POLYPEPTIDES AND USES THEREOF

(71) Applicant: Bioverativ Therapeutics Inc., Waltham, MA (US)

(72) Inventors: Susan Low, Pepperell, MA (US); Jennifer A. Dumont, Groton, MA (US); Alan J. Bitonti, Acton, MA (US)

(73) Assignee: Bioverativ Therapeutics Inc., Waltham, MA (US)

( * ) Notice: Subject to any disclaimer, the term of this patent is extended or adjusted under 35 U.S.C. 154(b) by 0 days.

(21) Appl. No.: 14/412,823

(22) PCT Filed: Jul. 5, 2013

(86) PCT No.: PCT/US2013/049460
§ 371 (c)(1),
(2) Date: Jan. 5, 2015

(87) PCT Pub. No.: WO2014/008480
PCT Pub. Date: Jan. 9, 2014

(65) Prior Publication Data

US 2015/0191526 A1 Jul. 9, 2015

Related U.S. Application Data

(60) Provisional application No. 61/668,889, filed on Jul. 6, 2012.

(51) Int. Cl.

| | |
|---|---|
| ***C07K 14/765*** | (2006.01) |
| ***A61K 38/00*** | (2006.01) |
| ***A61K 35/00*** | (2006.01) |
| ***C07K 14/755*** | (2006.01) |

(52) U.S. Cl.
CPC ............ *C07K 14/755* (2013.01); *A61K 35/00* (2013.01); *A61K 38/00* (2013.01); *C07K 2319/30* (2013.01); *C07K 2319/31* (2013.01)

(58) Field of Classification Search
None
See application file for complete search history.

(56) References Cited

U.S. PATENT DOCUMENTS 4,757,006 A 7/1988 Toole, Jr. et al.
4,868,112 A 9/1989 Toole, Jr.
4,965,199 A 10/1990 Capon et al.
4,994,371 A 2/1991 Davie et al.
5,004,803 A 4/1991 Kaufman et al.
5,112,950 A 5/1992 Meulien et al.
5,171,844 A 12/1992 Van Ooyen et al.
5,543,502 A 8/1996 Nordfang et al.
5,595,886 A 1/1997 Chapman et al.
5,610,278 A 3/1997 Nordfang et al.
5,648,260 A 7/1997 Winter et al.
5,712,122 A 1/1998 Boime et al.
5,739,277 A 4/1998 Presta et al.
5,789,203 A 8/1998 Chapman et al.
5,834,250 A 11/1998 Wells et al.
5,869,046 A 2/1999 Presta et al.
5,972,885 A 10/1999 Spira et al.
6,030,613 A 2/2000 Blumberg et al.
6,048,720 A 4/2000 Dalborg et al.
6,060,447 A 5/2000 Chapman et al.
6,086,875 A 7/2000 Blumberg et al.
6,096,871 A 8/2000 Presta et al.
6,121,022 A 9/2000 Presta et al.
6,194,551 B1 2/2001 Idusogie et al.
6,228,620 B1 5/2001 Chapman et al.
6,242,195 B1 6/2001 Idusogie et al.
6,251,632 B1 6/2001 Lillicrap et al.
6,277,375 B1 8/2001 Ward
6,316,226 B1 11/2001 Van Ooyen et al.
6,346,513 B1 2/2002 Van Ooyen et al.
6,458,563 B1 10/2002 Lollar
6,485,726 B1 11/2002 Blumberg et al.
6,528,624 B1 3/2003 Idusogie et al.
6,538,124 B1 3/2003 Idusogie et al.
6,686,179 B2 2/2004 Fleer et al.
6,737,056 B1 5/2004 Presta
6,821,505 B2 11/2004 Ward
6,998,253 B1 2/2006 Presta et al.
7,041,635 B2 5/2006 Kim et al.
(Continued)

FOREIGN PATENT DOCUMENTS

EP 0154316 A2 9/1985
EP 0295597 A2 12/1988
(Continued)

OTHER PUBLICATIONS

Pittman et al., Post-translational Requirements for Functional Factor V and Factor VIII Secretion in Mammalian Cells; JBC, vol. 269, No. 25, pp. 17329-17377, 1994.*
Tian et al., Computational prediction of furin cleavage sites by a hybrid method and understanding mechanism underlying diseases; Scientific Reports; vol. 2, No. 261, pp. 1-7, Feb. 16, 2012.*
Buyue, Y., et al., "A Single Chain Variant of Factor VIII Fc Fusion Protein Retains Normal in Vivo Efficacy but Exhibits Altered in Vitro Activity," *PLoS One* 9(11):e113600, Public Library of Science, United States, 19 pages (Nov. 2014).
Camire, R.M. and Bos, M.H., "The Molecular Basis of Factor V and VIII Procofactor Activation," *Journal of Thrombosis and Haemostasis* 7(12): 1951-1961, Blackwell Pub., England (2009).
(Continued)

*Primary Examiner* — Addison D Ault
(74) *Attorney, Agent, or Firm* — Sterne, Kessler, Goldstein & Fox P.L.L.C.

(57) ABSTRACT

The present invention provides cell lines for producing single chain FVIII polypeptides, e.g., chimeric single chain FVIII polypeptides, methods of producing single chain FVIII polypeptides, single chain FVIII polypeptides, and methods of treating Hemophilia A with a single chain Factor VIII polypeptide.

17 Claims, 4 Drawing Sheets

(56) References Cited

U.S. PATENT DOCUMENTS

Figure 1:
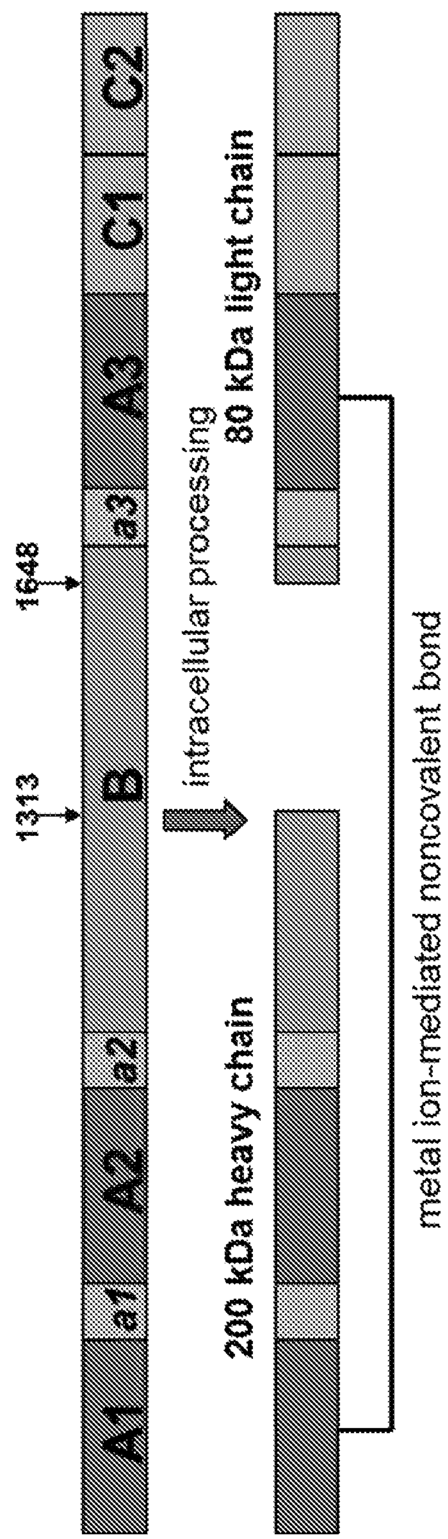

| | | | | |
|---|---|---|---|---|
| 7,083,784 | B2 | 8/2006 | Dall'Acqua et al. | |
| 7,317,091 | B2 | 1/2008 | Lazar et al. | |
| 7,348,004 | B2 | 3/2008 | Peters et al. | |
| 7,404,956 | B2 | 7/2008 | Peters et al. | |
| 7,592,010 | B2 | 9/2009 | Rosen et al. | |
| 7,632,921 | B2 | 12/2009 | Pan et al. | |
| 7,862,820 | B2 | 1/2011 | Peters et al. | |
| 8,329,182 | B2 | 12/2012 | Peters et al. | |
| 8,449,884 | B2 | 5/2013 | Rivera et al. | |
| 8,815,250 | B2 | 8/2014 | Rivera et al. | |
| 8,932,830 | B2 | 1/2015 | Peters et al. | |
| 2003/0235536 | A1 | 12/2003 | Blumberg et al. | |
| 2005/0032174 | A1 | 2/2005 | Peters et al. | |
| 2005/0100990 | A1 | 5/2005 | Saenko et al. | |
| 2005/0260194 | A1 | 11/2005 | Peters et al. | |
| 2007/0172928 | A1 | 7/2007 | Peters et al. | |
| 2007/0231329 | A1 | 10/2007 | Lazar et al. | |
| 2007/0237765 | A1 | 10/2007 | Lazar et al. | |
| 2007/0237766 | A1 | 10/2007 | Lazar et al. | |
| 2007/0237767 | A1 | 10/2007 | Lazar et al. | |
| 2007/0243188 | A1 | 10/2007 | Lazar et al. | |
| 2007/0248603 | A1 | 10/2007 | Lazar et al. | |
| 2007/0286859 | A1 | 12/2007 | Lazar et al. | |
| 2008/0057056 | A1 | 3/2008 | Lazar et al. | |
| 2009/0087411 | A1 | 4/2009 | Fares et al. | |
| 2009/0092582 | A1 | 4/2009 | Bogin et al. | |
| 2010/0189682 | A1 | 7/2010 | Schellenberger et al. | |
| 2010/0292130 | A1 | 11/2010 | Skerra et al. | |
| 2011/0182896 | A1 | 7/2011 | Rivera et al. | |
| 2011/0182919 | A1 | 7/2011 | Peters et al. | |
| 2012/0308641 | A1* | 12/2012 | Arruda ................ | C07K 14/755<br>424/450 |
| 2013/0108629 | A1* | 5/2013 | Dumont ................ | A61K 38/37<br>424/134.1 |
| 2013/0171138 | A1 | 7/2013 | Peters et al. | |
| 2013/0273047 | A1 | 10/2013 | Rivera et al. | |
| 2013/0281671 | A1 | 10/2013 | Peters et al. | |
| 2015/0023959 | A1 | 1/2015 | Chhabra et al. | |
| 2015/0044207 | A1 | 2/2015 | Rivera et al. | |
| 2015/0139947 | A1 | 5/2015 | Peters et al. | |

FOREIGN PATENT DOCUMENTS

| | | | |
|---|---|---|---|
| EP | 0401384 | A1 | 12/1990 |
| EP | 2173890 | B1 | 3/2011 |
| WO | WO-8704187 | A1 | 7/1987 |
| WO | WO-8707144 | A1 | 12/1987 |
| WO | WO-8800831 | A1 | 2/1988 |
| WO | WO-8803558 | A1 | 5/1988 |
| WO | WO-8807089 | A1 | 9/1988 |
| WO | WO-8808035 | A1 | 10/1988 |
| WO | WO-9109122 | A1 | 6/1991 |
| WO | WO-9216221 | A1 | 10/1992 |
| WO | WO-9534326 | A1 | 12/1995 |
| WO | WO-9614339 | A1 | 5/1996 |
| WO | WO-9805787 | A1 | 2/1998 |
| WO | WO-9823289 | A1 | 6/1998 |
| WO | WO-9951642 | A1 | 10/1999 |
| WO | WO-9958572 | A1 | 11/1999 |
| WO | WO-0009560 | A2 | 2/2000 |
| WO | WO-0032767 | A1 | 6/2000 |
| WO | WO-0042072 | A2 | 7/2000 |
| WO | WO-0244215 | A2 | 6/2002 |
| WO | WO-02060919 | A2 | 8/2002 |
| WO | WO-03074569 | A2 | 9/2003 |
| WO | WO-03077834 | A2 | 9/2003 |
| WO | WO-2004016750 | A2 | 2/2004 |
| WO | WO-2004029207 | A2 | 4/2004 |
| WO | WO-2004035752 | A2 | 4/2004 |
| WO | WO-2004063351 | A2 | 7/2004 |
| WO | WO-2004074455 | A2 | 9/2004 |
| WO | WO-2004099249 | A2 | 11/2004 |
| WO | WO-2004101740 | A2 | 11/2004 |
| WO | WO-2005040217 | A2 | 5/2005 |
| WO | WO-2005047327 | A2 | 5/2005 |
| WO | WO-2005070963 | A1 | 8/2005 |
| WO | WO-2005077981 | A2 | 8/2005 |
| WO | WO-2005092925 | A2 | 10/2005 |
| WO | WO-2005123780 | A2 | 12/2005 |
| WO | WO-2006019447 | A1 | 2/2006 |
| WO | WO-2006047350 | A2 | 5/2006 |
| WO | WO-2006074199 | A1 | 7/2006 |
| WO | WO-2006085967 | A2 | 8/2006 |
| WO | WO-2007103515 | A2 | 9/2007 |
| WO | WO-2008155134 | A1 | 12/2008 |
| WO | WO-2009023270 | A2 | 2/2009 |
| WO | WO-2010091122 | A1 | 8/2010 |
| WO | WO-2011041770 | A1 | 4/2011 |
| WO | WO-2012006623 | A1 | 1/2012 |
| WO | WO 2013/009627 | A2 | 1/2013 |
| WO | WO 2013/106787 | A1 | 7/2013 |
| WO | WO-2014008480 | A2 | 1/2014 |

OTHER PUBLICATIONS

Dumont, J.A., et al., "Prolonged Activity of a Recombinant Factor VIII-Fc Fusion Protein in Hemophilia A Mice and Dogs," *Blood* 119(13):3024-3030, The American Society of Hematology, United States (2012).

Extended European Search Report for EP Application No. 13813225.3, European Patent Office, Germany, dated Jan. 11, 2016, 15 pages.

Greene, T.K., et al., "Understanding Ectopically Expressed Factor VIII (F8) In Megakaryocytes: Implications for Optimum Platelet-Delivered F8 Activity for Gene Therapy," Abstract No. 2205, 52nd ASH Annual Meeting and Exposition, Dec. 4-7, Orlando, Florida, American Society of Hematology, 2 pages (2010).

Peters, R.T., et al., "Biochemical and Functional Characterization of a Recombinant Monomeric Factor VIII-Fc Fusion Protein," *Journal of Thrombosis and Haemostasis* 11 (1):132-141, Blackwell Publishing, England (2012).

Powell, J.S., et al., "Safety and Prolonged Activity of Recombinant Factor VIII Fc Fusion Protein in Hemophilia A Patients," *Blood* 119 (13):3031-3037, The American Society of Hematology, United States (2012).

Sabatino, D.E., et al., "Recombinant Canine B-Domain Deleted FVIII Exhibits High Specific Activity and is Safe in the Canine Hemophilia A Model," *Blood* 114 (20):4562-4565, American Society of Hematology, United States (2009).

Siner, J.I., et al., "Bioengineering Factor VIII B-Domain Sequences Improves Function and Efficacy in Hemophilia A Models," Abstract No. 2208, 54th ASH Annual Meeting and Exposition, Dec. 8-11, Atlanta, Georgia, American Society of Hematology, 1 page (2012).

Siner, J.I., et al., "Minimal Modification in the Factor VIII B-Domain Sequence Ameliorates the Murine Hemophilia A Phenotype," *Blood* 121 (21):4396-4403, American Society of Hematology, United States (May 2013).

Armour, K.L., et al., "Recombinant Human IgG Molecules Lacking Fcγ Receptor I Binding and Monocyte Triggering Activities," European Journal of Immunology 29(8):2613-2624, Wiley-VCH, Germany (1999).

Bai, Y., et al., "Recombinant granulocyte colony-stimulating factor-transferrin fusion protein as an oral myelopoietic agent," Proceedings of the National Academy of Sciences USA 102(20):7292-7296, National Academy of Sciences, United States (2005).

Brandsma, M.E., et al., "Recombinant human transferrin: Beyond iron binding and transport," Biotechnology Advances 29(2):230-238, Elsevier, United States (2011).

Burmeister, W.P., et al., "Crystal structure of the complex of rat neonatal Fc receptor with Fc," Nature 372(6504):379-383, Nature Publishing Group, England (1994).

Cameron, C., et al., "The Canine Factor VIII cDNA and 5' Flanking Sequence," Thrombosis and Haemostasis 79(2)317-322, Schattauer Verlag, Germany (1998).

Cutler, J.A., et al., "The identification and Classification of 41 novel Mutations in the Factor VIII Gene (F8C)," Human Mutation 19(3):274-278, Wiley-Liss, Inc., England (2002).

(56) References Cited

OTHER PUBLICATIONS

Dennis, M.S., et al., "Albumin Binding as a General Strategy for Improving the Pharmacokinetics of Proteins," The Journal of Biological Chemistry 277(38):35035-35043, The American Society for Biochemistry and Molecular Biology, Inc., United States (2002).
Donath, M-J., S.H, et al., "Characterization of Des-(741-1668)-Factor VIII, a Single-Chain Factor VIII Variant with a Fusion Site Susceptible to Proteolysis by Thrombin and Factor Xa," The Biochemical Journal 312(Pt 1):49-55, Portland Press, England(1995).
Eaton, D.L., et al., "Construction and Characterization of an Active Factor VIII Variant Lacking the Central One-Third of the Molecule," Biochemistry 25(26):8343-8347, American Chemical Society, United States (1986).
Fatouros, A., et al., "Recombinant Factor VIII SQ—Influence of Oxygen, Metal Ions, pH and Ionic Strength on its Stability in Aqueous Solution," International Journal of Pharmaceutics 155(1):121-131, Elsevier, United States (1997).
Francis, G.E., "Protein Modification and Fusion Proteins," Focus on Growth Factors 3(2):4-10, Mediscript, England (1992).
Friend, P.J., et al.. "Phase I Study of an Engineered Aglycosylated Humanized CD3 Antibody in Renal Transplant Rejection," Transplantation 68(11):1632-1637, Lippincott Williams & Wilkins, Inc., United States (1999).
GenBank, "*Homo sapiens* Transferrin (TF), mRNA," Accession No. NM001063 published on May 25, 2014, accessed at http://www.ncbi.nlm.nih.gov/nuccore/NM_001063, accessed on Sep. 24, 2014, 5 pages.
GenBank, "*Homo sapiens* Transferrin (TF), mRNA," Accession No. XM002793 published on May 13, 2002, accessed at https://www.ncbi.nlm.nih.gov/nuccore/XM_002793.7?report=genbank, accessed on Sep. 24, 2014, 2 pages.
GenBank, "*Homo sapiens* Transferrin (TF), mRNA," Accession No. XM039847 published on Jul. 16, 2001, accessed at http://www.ncbi.nlm.nih.gov/nuccore/XM_039847.1?report=genbank, accessed on Sep. 24, 2014, 2 pages.
GenBank, "*Homo sapiens* Transferrin (TF), mRNA," Accession No. XM039845 published Jul. 16, 2001, accessed at https://www.ncbi.nlm.nih.gov/nuccore/XM_039845.1?report=genbank, accessed on Sep. 24, 2014, 2 pages.
GenBank, "Human Transferrin mRNA, Complete cds," Accession No. M12530.1, published on Jan. 14, 1995, accessed at http://www.ncbi.nlm.nih.gov/nuccore/M1253014, accessed on Jan. 15, 2015, 2 pages.
GenBank, "Transferrin [human, liver, mRNA, 2347 nt]," Accession No. S95936.1, published on May 7, 1993, accessed at http://www.ncbi.nlm.nih.gov/nuccore/S95936, accessed on Sep. 24, 2014, 2 pages.
Gitschier, J., et al., "Characterization of the Human Factor VIII Gene," Nature 312(5992):326-330, Nature Publishing Group, England (1984).
Hoeben, R.C., et al., "Expression of Functional Factor VIII in Primary Human Skin Fibroblasts after Retrovirus-mediated Gene Transfer," The Journal of Biological Chemistry 265(13):7318-7323, The American Society for Biochemistry and Molecular Biology, United States (1990).
Holt, L.J., et al., "Anti-Serum Albumin Domain Antibodies for Extending the Half-Lives of Short Lived Drugs," Protein Engineering, Design and Selection 21(5):283-288, Oxford University Press, England (2008).
International Preliminary Report on Patentability for International Application No. PCT/US2013/049460, The International Bureau of WIPO, Switzerland, dated Jan. 6, 2015, 9 pages.
International Search Report and Written Opinion for International Application No. PCT/US2013/049460, International Searching Authority, Alexandria, Virginia, USA, dated Feb. 18, 2014, 13 pages.
Israel, E.J., et al., "Expression of the neonatal Fc receptor, FcRn, on human intestinal epithelial cells," Immunology 92(1):69-74, Blackwell Sciences, England (1997).
Kasuda, S., et al., "Establishment of embryonic stem cells secreting human factor VIII for cell-based treatment of hemophilia A," Journal of Thrombosis and Haemostasis 6(8):1352-1359, International Society on Thrombosis and Haemostasis, England (2008).
Kim, B-J., et al., "Transferrin Fusion Technology: a Novel Approach to Prolonging Biological Half-Life of Insulinotropic Peptides," The Journal of Pharmacology and Experimental Therapeutics 334(3):682-692, American Society for Pharmacology and Experimental Therapeutics, United States (2010).
Kobayashi, N., et al., "FcRn-Mediated Transcytosis of Immunoglobulin G in Human Renal Proximal Tubular Epithelial Cells," American Journal of Physiology 282(2):F358-F365, American Physiological Society, United States (2002).
Kraulis, P.J., et al., "The Serum Albumin-Binding Domain of Streptococcal Protein G is a Three-Helical Bundle: a Heteronuclear NMR study," FEBS Letters 378(2):190-194, Federation of European Biochemical Societies, England (1996).
Langner, K-D., et al., "Synthesis of Biologically Active Deletion Mutants of Human Factor VIII:C," Behring Institute Mitteilungen 82:16-25, Behringwerke AG, Germany (1988).
Li, H., et al., "The role of the transferrin-transferrin-receptor system in drug delivery and targeting," TRENDS in Pharmacological Sciences 23(5):206-209, Elsevier Science Ltd., England (2002).
Linhult, M., et al., "Mutational Analysis of the Interaction Between Albumin-Binding Domain from Streptococcal Protein G and Human Serum Albumin," Protein Science 11(2):206-213, Cold Spring Harbor Laboratory Press, United States (2002).
Malik, F., et al., "Polyethylene Glycol (PEG)-modified Granulocyte-Macrophage Colony-stimulating Factor (GM-CSF) with Conserved Biological Activity," Experimental Hematology 20(8):1028-1035, International Society for Experimental Hematology, United States (1992).
Mannucci, P.M. and Tuddenham, E.G.D., "The Hemophilias—from Royal Genes to Gene Therapy," New England Journal of Medicine 344(23):1773-1779, Massachusetts Medical Society, United States (2001).
McCue, J.T., et al., "Application of a Novel Affinity Adsorbent for the Capture and Purification of Recombinant Factor VIII Compounds," Journal of Chromatography A 1216(45):7824-7830, Elsevier, Netherlands (2009).
Mei, B., et al., "Rational Design of a Fully active, Long-Acting PEGylated Factor VIII for Hemophilia A Treatment," Blood 116(2):270-279, The American Society of Hematology, United States (2010).
Meulien, P., et al., "A new Recombinant Procoagulant Protein Derived from the cDNA Encoding Human Factor VIII," Protein Engineering 2(4):301-306, IRL Press Ltd., England (1988).
Miao, H.Z., et al., "Bioengineering of coagulation factor VIII for improved secretion," Blood 103(9):3412-3419, The American Society of Hematology, United States (2004).
Muller, D. and Kontermann, R.E., "Recombinant Bispecific Antibodies for Cellular Cancer Immunotherapy," Current Opinion in Molecular Therapeutics 9(4):319-326, The Thomson Corporation, United States (2007).
Peyvandi, F., el al,, "Genetic diagnosis of haemophilia and other inherited bleeding disorders," Haemophilia 12(Suppl 3):82-89, Blackwell Publishing Ltd., England (2006).
Pipe, S.W. and Kaufman, R.J., "Characterization of a Genetically Engineered Inactivation-Resistant Coagulation Factor VIIIa," Proceedings of the National Acedemy of Sciences 94(22):11851-11856, National Academy of Sciences, Unites States (1997).
Pipe, S.W., et al., "Functional factor VIII made with von Willebrand factor at high levels in transgenic milk," Journal of Thrombosis and Haemostasis 9(11):2235-2242, International Society on Thrombosis and Haemostasis, England (2011).
Plantier, J-L., et al., "B-Domain Deleted Factor VIII is Aggregated and Degraded Through Proteasomal and Lysosomal Pathways," Thrombosis and Haemostasis 93(5):824-832, Stuttgart, Schattauer, Germany (2005).
Rodriguez-Merchan, E.C. "Management of Musculoskeletal Complications of Hemophilia," Seminars in Thrombosis and Hemostasis 29(1):87-95, Thieme, United States (2003).

(56) References Cited

OTHER PUBLICATIONS

Roovers, R.C., et al., "Efficient Inhibition of EGFR Signaling and of Tumour Growth by Antagonistic Anti-EGFR Nanobodies," Cancer Immunology, Immunotherapy 56(3):303-317, Springer Verlag, Germany (2007).
Routledge, E.G., et al., "The Effect of Aglycosylation on the Immunogenicity of a Humanized Therapeutic CD3 Monoclonal Antibody," Transplantation 60(8):847-853, Williams & Wilkins, United States (1995).
Sandberg, H., et al., "Structural and Functional Characterization of B-domain Deleted Recombinant Factor VIII," Seminars in Hematology 38(2 Supp 4):4-12, W.B. Saunders, New York (2001).
Sarver, N., et al., "Stable Expression of Recombinant Factor VIII Molecules Using a Bovine Papillomavirus Vector," DNA 6(6):553-564, Mary Ann Liebert, Inc., United States (1987).
Scallan, C.D., et al., "Phenotypic Correction of a Mouse Model of Hemophilia A Using AAV2 Vectors Encoding the Heavy and Light Chains of FVIII," Blood 102(12):3919-3926, American Society of Hematology, United States (2003).
Schellenberger, V., et al., "A Recombinant Polypeptide Extends the in Vivo Half-Life of Peptides and Proteins in a Tunable Manner," Nature Biotechnology 27(12):1186-1190, Nature America, Inc., United States (2009).
Schulte, S., "Half-life Extension Through Albumin Fusion Technologies," Thrombosis Research 124(Suppl. 2):S6-S8, Elsevier Ltd, United States (2009).
Shields, R.L., et al., "High Resolution Mapping of the Binding Site on Human IgG1 for FcGammaRI, FcGammaRII, FcGammaRIII, and FcRn and Design of IgG1 Variants with Improved Binding to the FcGammaR*," The Journal of Biological Chemistry 276(9):6591-6604, The American Society for Biochemistry and Molecular Biology, Inc., United States (2001).
Sommermeyer, V.K., et al., "Klinisch Verwendete Hydroxyethylstarke: Physikalisch-Chemische Charakterisierung," Krankenhauspharmazie 8(8):271-278, Deutscher Apotheker Verlag, Birkenwaldstr, Germany (1987).
Story, C.M., et al., "A Major Histocompatibility Complex Class I-like Fc Receptor Cloned from Human Placenta: Possible Role in Transfer of Immunoglobulin G from Mother to Fetus," The Journal of Experimental Medicine 180(6):2377-2381, The Rockefeller University Press, United States (1994).
Toole, J.J., et al., "A large region (≈95 kDa) of human factor VIII is dispensable for in vitro procoagulant activity," Proceedings of the National Academy of Sciences USA 83(16):5939-5942, National Academy of Sciences, United States (1986).
Toole, J.J., et al., "Molecular Cloning of a cDNA Encoding Human Antihaemophilic Factor," Nature 312(5992):342-347, Nature Publishing Group, England (1984).
Tr Ssel, S., et al., "New Strategy for the Extension of the Serum Half-Life of Antibody Fragments," Bioconjugate Chemistry 20(12):2286-2292, American Chemical Society, United States (2009).
Vehar, G.A., et al., "Structure of Human Factor VIII," Nature 312(5992):337-342, Nature Publishing Group, England (1984).
Wakabayashi, H., et al., "Residues 110-126 in the A1 Domain of Factor VIII Contain a $Ca^{2+}$ Binding Site Required for Cofactor Activity," The Journal of Biological Chemistry 279(13):12677-12684, The American Society for Biochemistry and Molecular Biology, Inc., United States (2004).
Wang, Y., et al., "Receptor-Mediated Activation of a Proinsulin-Transferrin Fusion Protein in Hepatoma Cells," Journal of Controlled Release 155(3):386-392, Elsevier B.V., Netherlands (2011).
Ward, E.S. and Ghetie, V., "The Effector Functions of Immunoglobulins: Implications for Therapy," Therapeutic Immunology 2(2):77-94, Blackwell Science Ltd., England (1995).
Weidler, B., et al., "Pharmakokinetische Merkmale als Kriterien fur den klinischen Einsatz von Hydroxyethylstarke," Arzneimittel-Forschung 41(5):494-498, Editio Cantor, Germany (1991).
Wood, W.I., et al., "Expression of Active Human Factor VIII from Recombinant DNA Clones," Nature 312(5992):330-337, Nature Publishing Group, England (1984).
Capon, D.J., et al., "Designing CD4 Immunoadhesins for AIDS Therapy," Nature 337(6207):525-531, Nature Publishing Group, England (1989).

* cited by examiner

SEQUENCE LISTING

```
<160> NUMBER OF SEQ ID NOS: 28

<210> SEQ ID NO 1
<211> LENGTH: 5052
<212> TYPE: DNA
<213> ORGANISM: Artificial Sequence
<220> FEATURE:
<223> OTHER INFORMATION: B-Domain Deleted FVIIIFc Chain
<220> FEATURE:
<221> NAME/KEY: misc_feature
<222> LOCATION: (1)..(57)
<223> OTHER INFORMATION: FVIII signal
<220> FEATURE:
<221> NAME/KEY: misc_feature
<222> LOCATION: (4372)..(5052)
<223> OTHER INFORMATION: Fc region

<400> SEQUENCE: 1

atgcaaatag agctctccac ctgcttcttt ctgtgccttt tgcgattctg ctttagtgcc     60

accagaagat actacctggg tgcagtggaa ctgtcatggg actatatgca aagtgatctc    120

ggtgagctgc ctgtggacgc aagatttcct cctagagtgc caaaatcttt tccattcaac    180

acctcagtcg tgtacaaaaa gactctgttt gtagaattca cggatcacct tttcaacatc    240

gctaagccaa ggccaccctg gatgggtctg ctaggtccta ccatccaggc tgaggtttat    300

gatacagtgg tcattacact taagaacatg gcttcccatc ctgtcagtct tcatgctgtt    360

ggtgtatcct actggaaagc ttctgaggga gctgaatatg atgatcagac cagtcaaagg    420

gagaaagaag atgataaagt cttccctggt ggaagccata catatgtctg gcaggtcctg    480

aaagagaatg gtccaatggc ctctgaccca ctgtgcctta cctactcata tctttctcat    540

gtggacctgg taaaagactt gaattcaggc ctcattggag ccctactagt atgtagagaa    600

gggagtctgg ccaaggaaaa gacacagacc ttgcacaaat ttatactact tttgctgta    660

tttgatgaag ggaaaagttg gcactcagaa acaaagaact ccttgatgca ggatagggat    720

gctgcatctg ctcgggcctg gcctaaaatg cacacagtca atggttatgt aaacaggtct    780

ctgccaggtc tgattggatg ccacaggaaa tcagtctatt ggcatgtgat tggaatgggc    840

accactcctg aagtgcactc aatattcctc gaaggtcaca catttcttgt gaggaaccat    900

cgccaggcgt ccttggaaat ctcgccaata actttcctta ctgctcaaac actcttgatg    960

gaccttggac agtttctact gttttgtcat atctcttccc accaacatga tggcatggaa   1020

gcttatgtca aagtagacag ctgtccagag gaaccccaac tacgaatgaa aaataatgaa   1080
```

```
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatatacctt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctctcaaa acccaccagt cttgaaacgc catcaacggg aaataactcg tactactctt   2340
cagtcagatc aagaggaaat tgactatgat gataccatat cagttgaaat gaagaaggaa   2400
gattttgaca tttatgatga ggatgaaaat cagagccccc gcagctttca aaagaaaaca   2460
cgacactatt ttattgctgc agtggagagg ctctgggatt atgggatgag tagctcccca   2520
catgttctaa gaaacagggc tcagagtggc agtgtccctc agttcaagaa agttgttttc   2580
caggaattta ctgatggctc ctttactcag cccttatacc gtggagaact aaatgaacat   2640
ttgggactcc tggggccata tataagagca gaagttgaag ataatatcat ggtaactttc   2700
agaaatcagg cctctcgtcc ctattccttc tattctagcc ttatttctta tgaggaagat   2760
cagaggcaag gagcagaacc tagaaaaaac tttgtcaagc ctaatgaaac caaaacttac   2820
ttttggaaag tgcaacatca tatggcaccc actaaagatg agtttgactg caaagcctgg   2880
gcttatttct ctgatgttga cctggaaaaa gatgtgcact caggcctgat tggacccctt   2940
ctggtctgcc acactaacac actgaaccct gctcatggga gacaagtgac agtacaggaa   3000
tttgctctgt tttcaccat ctttgatgag accaaaagct ggtacttcac tgaaaatatg   3060
gaaagaaact gcagggctcc ctgcaatatc cagatggaag atcccacttt taaagagaat   3120
tatcgcttcc atgcaatcaa tggctacata atggatacac tacctggctt agtaatggct   3180
caggatcaaa ggattcgatg gtatctgctc agcatgggca gcaatgaaaa catccattct   3240
attcatttca gtggacatgt gttcactgta cgaaaaaaag aggagtataa aatggcactg   3300
tacaatctct atccaggtgt ttttgagaca gtggaaatgt taccatccaa agctggaatt   3360
tggcgggtgg aatgccttat tggcgagcat ctacatgctg ggatgagcac actttttctg   3420
gtgtacagca ataagtgtca gactcccctg ggaatggctt ctggacacat tagagatttt   3480
```

```
cagattacag cttcaggaca atatggacag tgggccccaa agctggccag acttcattat   3540

tccggatcaa tcaatgcctg gagcaccaag gagccctttt cttggatcaa ggtggatctg   3600

ttggcaccaa tgattattca cggcatcaag acccagggtg cccgtcagaa gttctccagc   3660

ctctacatct ctcagtttat catcatgtat agtcttgatg ggaagaagtg gcagacttat   3720

cgaggaaatt ccactggaac cttaatggtc ttctttggca atgtggattc atctgggata   3780

aaacacaata tttttaaccc tccaattatt gctcgataca tccgtttgca cccaactcat   3840

tatagcattc gcagcactct tcgcatggag ttgatgggct gtgatttaaa tagttgcagc   3900

atgccattgg gaatggagag taaagcaata tcagatgcac agattactgc ttcatcctac   3960

tttaccaata tgtttgccac ctggtctcct tcaaaagctc gacttcacct ccaagggagg   4020

agtaatgcct ggagacctca ggtgaataat ccaaaagagt ggctgcaagt ggacttccag   4080

aagacaatga aagtcacagg agtaactact cagggagtaa aatctctgct taccagcatg   4140

tatgtgaagg agttcctcat ctccagcagt caagatggcc atcagtggac tctctttttt   4200

cagaatggca aagtaaaggt ttttcaggga aatcaagact ccttcacacc tgtggtgaac   4260

tctctagacc caccgttact gactcgctac cttcgaattc acccccagag ttgggtgcac   4320

cagattgccc tgaggatgga ggttctgggc tgcgaggcac aggacctcta cgacaaaact   4380

cacacatgcc caccgtgccc agctccagaa ctcctgggcg gaccgtcagt cttcctcttc   4440

cccccaaaac ccaaggacac cctcatgatc tcccggaccc ctgaggtcac atgcgtggtg   4500

gtggacgtga gccacgaaga ccctgaggtc aagttcaact ggtacgtgga cggcgtggag   4560

gtgcataatg ccaagacaaa gccgcgggag gagcagtaca acagcacgta ccgtgtggtc   4620

agcgtcctca ccgtcctgca ccaggactgg ctgaatggca aggagtacaa gtgcaaggtc   4680

tccaacaaag ccctcccagc ccccatcgag aaaaccatct ccaaagccaa agggcagccc   4740

cgagaaccac aggtgtacac cctgccccca tcccgggatg agctgaccaa gaaccaggtc   4800

agcctgacct gcctggtcaa aggcttctat cccagcgaca tcgccgtgga gtgggagagc   4860

aatgggcagc cggagaacaa ctacaagacc acgcctcccg tgttggactc cgacggctcc   4920

ttcttcctct acagcaagct caccgtggac aagagcaggt ggcagcaggg gaacgtcttc   4980

tcatgctccg tgatgcatga ggctctgcac aaccactaca cgcagaagag cctctccctg   5040

tctccgggta aa                                                       5052
```

```
<210> SEQ ID NO 2
<211> LENGTH: 1684
<212> TYPE: PRT
<213> ORGANISM: Artificial Sequence
<220> FEATURE:
<223> OTHER INFORMATION: B domain deleted FVIII-Fc chain
<220> FEATURE:
<221> NAME/KEY: MISC_FEATURE
<222> LOCATION: (1)..(19)
<223> OTHER INFORMATION: Signal
<220> FEATURE:
<221> NAME/KEY: MISC_FEATURE
<222> LOCATION: (20)..(753)
<223> OTHER INFORMATION: Heavy chain (HC)
<220> FEATURE:
<221> NAME/KEY: MISC_FEATURE
<222> LOCATION: (760)..(773)
<223> OTHER INFORMATION: B domain
<220> FEATURE:
<221> NAME/KEY: MISC_FEATURE
<222> LOCATION: (1457)..(1684)
<223> OTHER INFORMATION: Fc region
```

<400> SEQUENCE: 2

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415
```

```
Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830
```

```
Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu  Phe Ala Leu Phe Phe  Thr Ile Phe
        995                 1000                1005

Asp Glu  Thr Lys Ser Trp Tyr  Phe Thr Glu Asn Met  Glu Arg Asn
    1010                1015                1020

Cys Arg  Ala Pro Cys Asn Ile  Gln Met Glu Asp Pro  Thr Phe Lys
    1025                1030                1035

Glu Asn  Tyr Arg Phe His Ala  Ile Asn Gly Tyr Ile  Met Asp Thr
    1040                1045                1050

Leu Pro  Gly Leu Val Met Ala  Gln Asp Gln Arg Ile  Arg Trp Tyr
    1055                1060                1065

Leu Leu  Ser Met Gly Ser Asn  Glu Asn Ile His Ser  Ile His Phe
    1070                1075                1080

Ser Gly  His Val Phe Thr Val  Arg Lys Lys Glu Glu  Tyr Lys Met
    1085                1090                1095

Ala Leu  Tyr Asn Leu Tyr Pro  Gly Val Phe Glu Thr  Val Glu Met
    1100                1105                1110

Leu Pro  Ser Lys Ala Gly Ile  Trp Arg Val Glu Cys  Leu Ile Gly
    1115                1120                1125

Glu His  Leu His Ala Gly Met  Ser Thr Leu Phe Leu  Val Tyr Ser
    1130                1135                1140

Asn Lys  Cys Gln Thr Pro Leu  Gly Met Ala Ser Gly  His Ile Arg
    1145                1150                1155

Asp Phe  Gln Ile Thr Ala Ser  Gly Gln Tyr Gly Gln  Trp Ala Pro
    1160                1165                1170

Lys Leu  Ala Arg Leu His Tyr  Ser Gly Ser Ile Asn  Ala Trp Ser
    1175                1180                1185

Thr Lys  Glu Pro Phe Ser Trp  Ile Lys Val Asp Leu  Leu Ala Pro
    1190                1195                1200

Met Ile  Ile His Gly Ile Lys  Thr Gln Gly Ala Arg  Gln Lys Phe
    1205                1210                1215

Ser Ser  Leu Tyr Ile Ser Gln  Phe Ile Ile Met Tyr  Ser Leu Asp
    1220                1225                1230

Gly Lys  Lys Trp Gln Thr Tyr  Arg Gly Asn Ser Thr  Gly Thr Leu
```

```
    1235                1240                1245

Met Val  Phe Phe Gly Asn Val  Asp Ser Ser Gly Ile  Lys His Asn
    1250                1255                1260

Ile Phe  Asn Pro Pro Ile Ile  Ala Arg Tyr Ile Arg  Leu His Pro
    1265                1270                1275

Thr His  Tyr Ser Ile Arg Ser  Thr Leu Arg Met Glu  Leu Met Gly
    1280                1285                1290

Cys Asp  Leu Asn Ser Cys Ser  Met Pro Leu Gly Met  Glu Ser Lys
    1295                1300                1305

Ala Ile  Ser Asp Ala Gln Ile  Thr Ala Ser Ser Tyr  Phe Thr Asn
    1310                1315                1320

Met Phe  Ala Thr Trp Ser Pro  Ser Lys Ala Arg Leu  His Leu Gln
    1325                1330                1335

Gly Arg  Ser Asn Ala Trp Arg  Pro Gln Val Asn Asn  Pro Lys Glu
    1340                1345                1350

Trp Leu  Gln Val Asp Phe Gln  Lys Thr Met Lys Val  Thr Gly Val
    1355                1360                1365

Thr Thr  Gln Gly Val Lys Ser  Leu Leu Thr Ser Met  Tyr Val Lys
    1370                1375                1380

Glu Phe  Leu Ile Ser Ser Ser  Gln Asp Gly His Gln  Trp Thr Leu
    1385                1390                1395

Phe Phe  Gln Asn Gly Lys Val  Lys Val Phe Gln Gly  Asn Gln Asp
    1400                1405                1410

Ser Phe  Thr Pro Val Val Asn  Ser Leu Asp Pro Pro  Leu Leu Thr
    1415                1420                1425

Arg Tyr  Leu Arg Ile His Pro  Gln Ser Trp Val His  Gln Ile Ala
    1430                1435                1440

Leu Arg  Met Glu Val Leu Gly  Cys Glu Ala Gln Asp  Leu Tyr Asp
    1445                1450                1455

Lys Thr  His Thr Cys Pro Pro  Cys Pro Ala Pro Glu  Leu Leu Gly
    1460                1465                1470

Gly Pro  Ser Val Phe Leu Phe  Pro Pro Lys Pro Lys  Asp Thr Leu
    1475                1480                1485

Met Ile  Ser Arg Thr Pro Glu  Val Thr Cys Val Val  Val Asp Val
    1490                1495                1500

Ser His  Glu Asp Pro Glu Val  Lys Phe Asn Trp Tyr  Val Asp Gly
    1505                1510                1515

Val Glu  Val His Asn Ala Lys  Thr Lys Pro Arg Glu  Glu Gln Tyr
    1520                1525                1530

Asn Ser  Thr Tyr Arg Val Val  Ser Val Leu Thr Val  Leu His Gln
    1535                1540                1545

Asp Trp  Leu Asn Gly Lys Glu  Tyr Lys Cys Lys Val  Ser Asn Lys
    1550                1555                1560

Ala Leu  Pro Ala Pro Ile Glu  Lys Thr Ile Ser Lys  Ala Lys Gly
    1565                1570                1575

Gln Pro  Arg Glu Pro Gln Val  Tyr Thr Leu Pro Pro  Ser Arg Asp
    1580                1585                1590

Glu Leu  Thr Lys Asn Gln Val  Ser Leu Thr Cys Leu  Val Lys Gly
    1595                1600                1605

Phe Tyr  Pro Ser Asp Ile Ala  Val Glu Trp Glu Ser  Asn Gly Gln
    1610                1615                1620

Pro Glu  Asn Asn Tyr Lys Thr  Thr Pro Pro Val Leu  Asp Ser Asp
    1625                1630                1635
```

```
Gly Ser  Phe Phe Leu Tyr Ser  Lys Leu Thr Val Asp  Lys Ser Arg
    1640                 1645                 1650

Trp Gln  Gln Gly Asn Val Phe  Ser Cys Ser Val Met  His Glu Ala
    1655                 1660                 1665

Leu His  Asn His Tyr Thr Gln  Lys Ser Leu Ser Leu  Ser Pro Gly
    1670                 1675                 1680

Lys


<210> SEQ ID NO 3
<211> LENGTH: 741
<212> TYPE: DNA
<213> ORGANISM: Artificial Sequence
<220> FEATURE:
<223> OTHER INFORMATION: Fc region
<220> FEATURE:
<221> NAME/KEY: misc_signal
<222> LOCATION: (1)..(60)
<223> OTHER INFORMATION: Mouse Ig kappa signal

<400> SEQUENCE: 3

atggagacag acacactcct gctatgggta ctgctgctct gggttccagg ttccactggt     60

gacaaaactc acacatgccc accgtgccca gcacctgaac tcctgggagg accgtcagtc    120

ttcctcttcc ccccaaaacc caaggacacc ctcatgatct cccggacccc tgaggtcaca    180

tgcgtggtgg tggacgtgag ccacgaagac cctgaggtca agttcaactg gtacgtggac    240

ggcgtggagg tgcataatgc caagacaaag ccgcgggagg agcagtacaa cagcacgtac    300

cgtgtggtca gcgtcctcac cgtcctgcac caggactggc tgaatggcaa ggagtacaag    360

tgcaaggtct ccaacaaagc cctcccagcc cccatcgaga aaaccatctc caaagccaaa    420

gggcagcccc gagaaccaca ggtgtacacc ctgcccccat cccgcgatga gctgaccaag    480

aaccaggtca gcctgacctg cctggtcaaa ggcttctatc ccagcgacat cgccgtggag    540

tgggagagca atgggcagcc ggagaacaac tacaagacca cgcctcccgt gttggactcc    600

gacggctcct tcttcctcta cagcaagctc accgtggaca agagcaggtg gcagcagggg    660

aacgtcttct catgctccgt gatgcatgag gctctgcaca accactacac gcagaagagc    720

ctctccctgt ctccgggtaa a                                              741


<210> SEQ ID NO 4
<211> LENGTH: 247
<212> TYPE: PRT
<213> ORGANISM: Artificial Sequence
<220> FEATURE:
<223> OTHER INFORMATION: Fc chain
<220> FEATURE:
<221> NAME/KEY: MISC_FEATURE
<222> LOCATION: (1)..(20)
<223> OTHER INFORMATION: heterologous signal from Mouse Ig kappa chain

<400> SEQUENCE: 4

Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
```

```
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys
                245


<210> SEQ ID NO 5
<211> LENGTH: 7734
<212> TYPE: DNA
<213> ORGANISM: Artificial Sequence
<220> FEATURE:
<223> OTHER INFORMATION: Full length FVIIIFc
<220> FEATURE:
<221> NAME/KEY: misc_signal
<222> LOCATION: (1)..(57)
<223> OTHER INFORMATION: FVIII signal
<220> FEATURE:
<221> NAME/KEY: misc_feature
<222> LOCATION: (7054)..(7734)
<223> OTHER INFORMATION: Fc region

<400> SEQUENCE: 5

atgcaaatag agctctccac ctgcttcttt ctgtgccttt tgcgattctg ctttagtgcc      60

accagaagat actacctggg tgcagtggaa ctgtcatggg actatatgca aagtgatctc     120

ggtgagctgc ctgtggacgc aagatttcct cctagagtgc caaaatcttt tccattcaac     180

acctcagtcg tgtacaaaaa gactctgttt gtagaattca cggatcacct tttcaacatc     240

gctaagccaa ggccaccctg gatgggtctg ctaggtccta ccatccaggc tgaggtttat     300

gatacagtgg tcattacact taagaacatg gcttcccatc ctgtcagtct tcatgctgtt     360

ggtgtatcct actggaaagc ttctgaggga gctgaatatg atgatcagac cagtcaaagg     420

gagaaagaag atgataaagt cttccctggt ggaagccata catatgtctg gcaggtcctg     480

aaagagaatg gtccaatggc ctctgaccca ctgtgcctta cctactcata tctttctcat     540

gtggacctgg taaaagactt gaattcaggc ctcattggag ccctactagt atgtagagaa     600

gggagtctgg ccaaggaaaa gacacagacc ttgcacaaat ttatactact ttttgctgta     660

tttgatgaag ggaaaagttg gcactcagaa acaaagaact ccttgatgca ggatagggat     720

gctgcatctg ctcgggcctg gcctaaaatg cacacagtca atggttatgt aaacaggtct     780
```

```
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag gaaccccaac tacgaatgaa aaataatgaa   1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatatacctt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctcccaga attcaagaca ccctagcact aggcaaaagc aatttaatgc caccacaatt   2340
ccagaaaatg acatagagaa gactgaccct tggtttgcac acagaacacc tatgcctaaa   2400
atacaaaatg tctcctctag tgatttgttg atgctcttgc gacagagtcc tactccacat   2460
gggctatcct tatctgatct ccaagaagcc aaatatgaga ctttttctga tgatccatca   2520
cctggagcaa tagacagtaa taacagcctg tctgaaatga cacacttcag gccacagctc   2580
catcacagtg ggacatggtt atttacccct gagtcaggcc tccaattaag attaaatgag   2640
aaactgggga caactgcagc aacagagttg aagaaacttg atttcaaagt ttctagtaca   2700
tcaaataatc tgatttcaac aattccatca gacaatttgg cagcaggtac tgataataca   2760
agttccttag gacccccaag tatgccagtt cattatgata gtcaattaga taccactcta   2820
tttggcaaaa agtcatctcc ccttactgag tctggtggac ctctgagctt gagtgaagaa   2880
aataatgatt caaagttgtt agaatcaggt ttaatgaata gccaagaaag ttcatgggga   2940
aaaaatgtat cgtcaacaga gagtggtagg ttatttaaag ggaaaagagc tcatggacct   3000
gctttgttga ctaaagataa tgccttattc aaagttagca tctctttgtt aaagacaaac   3060
aaaacttcca ataattcagc aactaataga aagactcaca ttgatggccc atcattatta   3120
attgagaata gtccatcagt ctggcaaaat atattagaaa gtgacactga gtttaaaaaa   3180
```

```
gtgacacctt tgattcatga cagaatgctt atggacaaaa atgctacagc tttgaggcta   3240
aatcatatgt caaataaaac tacttcatca aaaaacatgg aaatggtcca acagaaaaaa   3300
gagggcccca ttccaccaga tgcacaaaat ccagatatgt cgttctttaa gatgctattc   3360
ttgccagaat cagcaaggtg gatacaaagg actcatggaa agaactctct gaactctggg   3420
caaggcccca gtccaaagca attagtatcc ttaggaccag aaaaatctgt ggaaggtcag   3480
aatttcttgt ctgagaaaaa caaagtggta gtaggaaagg gtgaatttac aaaggacgta   3540
ggactcaaag agatggtttt tccaagcagc agaaacctat ttcttactaa cttggataat   3600
ttacatgaaa ataatacaca caatcaagaa aaaaaaattc aggaagaaat agaaaagaag   3660
gaaacattaa tccaagagaa tgtagttttg cctcagatac atacagtgac tggcactaag   3720
aatttcatga agaacctttt cttactgagc actaggcaaa atgtagaagg ttcatatgac   3780
ggggcatatg ctccagtact tcaagatttt aggtcattaa atgattcaac aaatagaaca   3840
aagaaacaca cagctcattt ctcaaaaaaa ggggaggaag aaaacttgga aggcttggga   3900
aatcaaacca agcaaattgt agagaaatat gcatgcacca caaggatatc tcctaataca   3960
agccagcaga attttgtcac gcaacgtagt aagagagctt tgaaacaatt cagactccca   4020
ctagaagaaa cagaacttga aaaaaggata attgtggatg acacctcaac ccagtggtcc   4080
aaaaacatga aacatttgac cccgagcacc ctcacacaga tagactacaa tgagaaggag   4140
aaaggggcca ttactcagtc tcccttatca gattgcctta cgaggagtca tagcatccct   4200
caagcaaata gatctccatt acccattgca aaggtatcat catttccatc tattagacct   4260
atatatctga ccagggtcct attccaagac aactcttctc atcttccagc agcatcttat   4320
agaaagaaag attctggggt ccaagaaagc agtcatttct tacaaggagc caaaaaaaat   4380
aacctttctt tagccattct aaccttggag atgactggtg atcaaagaga ggttggctcc   4440
ctggggacaa gtgccacaaa ttcagtcaca tacaagaaag ttgagaacac tgttctcccg   4500
aaaccagact tgcccaaaac atctggcaaa gttgaattgc ttccaaaagt tcacatttat   4560
cagaaggacc tattccctac ggaaactagc aatgggtctc ctggccatct ggatctcgtg   4620
gaagggagcc ttcttcaggg aacagaggga gcgattaagt ggaatgaagc aaacagacct   4680
ggaaaagttc cctttctgag agtagcaaca gaaagctctg caaagactcc ctccaagcta   4740
ttggatcctc ttgcttggga taaccactat ggtactcaga taccaaaaga agagtggaaa   4800
tcccaagaga agtcaccaga aaaaacagct tttaagaaaa aggataccat tttgtccctg   4860
aacgcttgtg aaagcaatca tgcaatagca gcaataaatg agggacaaaa taagcccgaa   4920
atagaagtca cctgggcaaa gcaaggtagg actgaaaggc tgtgctctca aaacccacca   4980
gtcttgaaac gccatcaacg ggaaataact cgtactactc ttcagtcaga tcaagaggaa   5040
attgactatg atgataccat atcagttgaa atgaagaagg aagattttga catttatgat   5100
gaggatgaaa atcagagccc ccgcagcttt caaaagaaaa cacgacacta ttttattgct   5160
gcagtggaga ggctctggga ttatgggatg agtagctccc cacatgttct aagaaacagg   5220
gctcagagtg gcagtgtccc tcagttcaag aaagttgttt tccaggaatt tactgatggc   5280
tcctttactc agcccttata ccgtggagaa ctaaatgaac atttgggact cctggggcca   5340
tatataagag cagaagttga agataatatc atggtaactt tcagaaatca ggcctctcgt   5400
ccctattcct tctattctag ccttatttct tatgaggaag atcagaggca aggagcagaa   5460
cctagaaaaa actttgtcaa gcctaatgaa accaaaactt acttttggaa agtgcaacat   5520
```

```
catatggcac ccactaaaga tgagtttgac tgcaaagcct gggcttattt ctctgatgtt   5580
gacctggaaa aagatgtgca ctcaggcctg attggacccc ttctggtctg ccacactaac   5640
acactgaacc ctgctcatgg gagacaagtg acagtacagg aatttgctct gtttttcacc   5700
atctttgatg agaccaaaag ctggtacttc actgaaaata tggaaagaaa ctgcagggct   5760
ccctgcaata tccagatgga agatcccact tttaaagaga attatcgctt ccatgcaatc   5820
aatggctaca taatggatac actacctggc ttagtaatgg ctcaggatca aaggattcga   5880
tggtatctgc tcagcatggg cagcaatgaa aacatccatt ctattcattt cagtggacat   5940
gtgttcactg tacgaaaaaa agaggagtat aaaatggcac tgtacaatct ctatccaggt   6000
gtttttgaga cagtggaaat gttaccatcc aaagctggaa tttggcgggt ggaatgcctt   6060
attggcgagc atctacatgc tgggatgagc acacttttc tggtgtacag caataagtgt   6120
cagactcccc tgggaatggc ttctggacac attagagatt ttcagattac agcttcagga   6180
caatatggac agtgggcccc aaagctggcc agacttcatt attccggatc aatcaatgcc   6240
tggagcacca aggagccctt ttcttggatc aaggtggatc tgttggcacc aatgattatt   6300
cacggcatca agacccaggg tgcccgtcag aagttctcca gcctctacat ctctcagttt   6360
atcatcatgt atagtcttga tgggaagaag tggcagactt atcgaggaaa ttccactgga   6420
accttaatgg tcttctttgg caatgtggat tcatctggga taaaacacaa tatttttaac   6480
cctccaatta ttgctcgata catccgtttg cacccaactc attatagcat tcgcagcact   6540
cttcgcatgg agttgatggg ctgtgattta aatagttgca gcatgccatt gggaatggag   6600
agtaaagcaa tatcagatgc acagattact gcttcatcct actttaccaa tatgtttgcc   6660
acctggtctc cttcaaaagc tcgacttcac ctccaaggga ggagtaatgc ctggagacct   6720
caggtgaata atccaaaaga gtggctgcaa gtggacttcc agaagacaat gaaagtcaca   6780
ggagtaacta ctcagggagt aaaatctctg cttaccagca tgtatgtgaa ggagttcctc   6840
atctccagca gtcaagatgg ccatcagtgg actctctttt ttcagaatgg caaagtaaag   6900
gtttttcagg gaaatcaaga ctccttcaca cctgtggtga actctctaga cccaccgtta   6960
ctgactcgct accttcgaat tcacccccag agttgggtgc accagattgc cctgaggatg   7020
gaggttctgg gctgcgaggc acaggacctc tacgacaaaa ctcacacatg cccaccgtgc   7080
ccagctccag aactcctggg cggaccgtca gtcttcctct tcccccaaa acccaaggac   7140
accctcatga tctcccggac ccctgaggtc acatgcgtgg tggtggacgt gagccacgaa   7200
gaccctgagg tcaagttcaa ctggtacgtg gacggcgtgg aggtgcataa tgccaagaca   7260
aagccgcggg aggagcagta caacagcacg taccgtgtgg tcagcgtcct caccgtcctg   7320
caccaggact ggctgaatgg caaggagtac aagtgcaagg tctccaacaa agccctccca   7380
gcccccatcg agaaaaccat ctccaaagcc aaagggcagc cccgagaacc acaggtgtac   7440
accctgcccc catcccggga tgagctgacc aagaaccagg tcagcctgac ctgcctggtc   7500
aaaggcttct atcccagcga catcgccgtg gagtgggaga gcaatgggca gccggagaac   7560
aactacaaga ccacgcctcc cgtgttggac tccgacggct ccttcttcct ctacagcaag   7620
ctcaccgtgg acaagagcag gtggcagcag gggaacgtct tctcatgctc cgtgatgcat   7680
gaggctctgc acaaccacta cacgcagaag agcctctccc tgtctccggg taaa         7734
```

<210> SEQ ID NO 6
<211> LENGTH: 2578
<212> TYPE: PRT
<213> ORGANISM: Artificial Sequence

```
<220> FEATURE:
<223> OTHER INFORMATION: Full length FVIIIFc chain
<220> FEATURE:
<221> NAME/KEY: MISC_FEATURE
<222> LOCATION: (1)..(19)
<223> OTHER INFORMATION: FVIII signal
<220> FEATURE:
<221> NAME/KEY: MISC_FEATURE
<222> LOCATION: (20)..(759)
<223> OTHER INFORMATION: HC
<220> FEATURE:
<221> NAME/KEY: MISC_FEATURE
<222> LOCATION: (760)..(1667)
<223> OTHER INFORMATION: B domain
<220> FEATURE:
<221> NAME/KEY: MISC_FEATURE
<222> LOCATION: (2352)..(2578)
<223> OTHER INFORMATION: Fc region

<400> SEQUENCE: 6

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
```

```
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735
```

```
Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
        755                 760                 765

Ser Thr Arg Gln Lys Gln Phe Asn Ala Thr Thr Ile Pro Glu Asn Asp
    770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
        835                 840                 845

Ser Leu Ser Glu Met Thr His Phe Arg Pro Gln Leu His His Ser Gly
    850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
        915                 920                 925

Pro Val His Tyr Asp Ser Gln Leu Asp Thr Thr Leu Phe Gly Lys Lys
    930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro  Ala Leu Leu Thr Lys  Asp Asn Ala
        995                 1000                1005

Leu Phe  Lys Val Ser Ile Ser  Leu Leu Lys Thr Asn  Lys Thr Ser
    1010                1015                1020

Asn Asn  Ser Ala Thr Asn Arg  Lys Thr His Ile Asp  Gly Pro Ser
    1025                1030                1035

Leu Leu  Ile Glu Asn Ser Pro  Ser Val Trp Gln Asn  Ile Leu Glu
    1040                1045                1050

Ser Asp  Thr Glu Phe Lys Lys  Val Thr Pro Leu Ile  His Asp Arg
    1055                1060                1065

Met Leu  Met Asp Lys Asn Ala  Thr Ala Leu Arg Leu  Asn His Met
    1070                1075                1080

Ser Asn  Lys Thr Thr Ser Ser  Lys Asn Met Glu Met  Val Gln Gln
    1085                1090                1095

Lys Lys  Glu Gly Pro Ile Pro  Pro Asp Ala Gln Asn  Pro Asp Met
    1100                1105                1110

Ser Phe  Phe Lys Met Leu Phe  Leu Pro Glu Ser Ala  Arg Trp Ile
    1115                1120                1125

Gln Arg  Thr His Gly Lys Asn  Ser Leu Asn Ser Gly  Gln Gly Pro
    1130                1135                1140
```

```
Ser Pro  Lys Gln Leu Val Ser  Leu Gly Pro Glu Lys  Ser Val Glu
    1145                 1150                 1155

Gly Gln  Asn Phe Leu Ser Glu  Lys Asn Lys Val Val  Val Gly Lys
    1160                 1165                 1170

Gly Glu  Phe Thr Lys Asp Val  Gly Leu Lys Glu Met  Val Phe Pro
    1175                 1180                 1185

Ser Ser  Arg Asn Leu Phe Leu  Thr Asn Leu Asp Asn  Leu His Glu
    1190                 1195                 1200

Asn Asn  Thr His Asn Gln Glu  Lys Lys Ile Gln Glu  Glu Ile Glu
    1205                 1210                 1215

Lys Lys  Glu Thr Leu Ile Gln  Glu Asn Val Val Leu  Pro Gln Ile
    1220                 1225                 1230

His Thr  Val Thr Gly Thr Lys  Asn Phe Met Lys Asn  Leu Phe Leu
    1235                 1240                 1245

Leu Ser  Thr Arg Gln Asn Val  Glu Gly Ser Tyr Asp  Gly Ala Tyr
    1250                 1255                 1260

Ala Pro  Val Leu Gln Asp Phe  Arg Ser Leu Asn Asp  Ser Thr Asn
    1265                 1270                 1275

Arg Thr  Lys Lys His Thr Ala  His Phe Ser Lys Lys  Gly Glu Glu
    1280                 1285                 1290

Glu Asn  Leu Glu Gly Leu Gly  Asn Gln Thr Lys Gln  Ile Val Glu
    1295                 1300                 1305

Lys Tyr  Ala Cys Thr Thr Arg  Ile Ser Pro Asn Thr  Ser Gln Gln
    1310                 1315                 1320

Asn Phe  Val Thr Gln Arg Ser  Lys Arg Ala Leu Lys  Gln Phe Arg
    1325                 1330                 1335

Leu Pro  Leu Glu Glu Thr Glu  Leu Glu Lys Arg Ile  Ile Val Asp
    1340                 1345                 1350

Asp Thr  Ser Thr Gln Trp Ser  Lys Asn Met Lys His  Leu Thr Pro
    1355                 1360                 1365

Ser Thr  Leu Thr Gln Ile Asp  Tyr Asn Glu Lys Glu  Lys Gly Ala
    1370                 1375                 1380

Ile Thr  Gln Ser Pro Leu Ser  Asp Cys Leu Thr Arg  Ser His Ser
    1385                 1390                 1395

Ile Pro  Gln Ala Asn Arg Ser  Pro Leu Pro Ile Ala  Lys Val Ser
    1400                 1405                 1410

Ser Phe  Pro Ser Ile Arg Pro  Ile Tyr Leu Thr Arg  Val Leu Phe
    1415                 1420                 1425

Gln Asp  Asn Ser Ser His Leu  Pro Ala Ala Ser Tyr  Arg Lys Lys
    1430                 1435                 1440

Asp Ser  Gly Val Gln Glu Ser  Ser His Phe Leu Gln  Gly Ala Lys
    1445                 1450                 1455

Lys Asn  Asn Leu Ser Leu Ala  Ile Leu Thr Leu Glu  Met Thr Gly
    1460                 1465                 1470

Asp Gln  Arg Glu Val Gly Ser  Leu Gly Thr Ser Ala  Thr Asn Ser
    1475                 1480                 1485

Val Thr  Tyr Lys Lys Val Glu  Asn Thr Val Leu Pro  Lys Pro Asp
    1490                 1495                 1500

Leu Pro  Lys Thr Ser Gly Lys  Val Glu Leu Leu Pro  Lys Val His
    1505                 1510                 1515

Ile Tyr  Gln Lys Asp Leu Phe  Pro Thr Glu Thr Ser  Asn Gly Ser
    1520                 1525                 1530

Pro Gly  His Leu Asp Leu Val  Glu Gly Ser Leu Leu  Gln Gly Thr
```

```
    1535                1540                1545

Glu Gly  Ala Ile Lys Trp Asn  Glu Ala Asn Arg Pro  Gly Lys Val
    1550                1555                1560

Pro Phe  Leu Arg Val Ala Thr  Glu Ser Ser Ala Lys  Thr Pro Ser
    1565                1570                1575

Lys Leu  Leu Asp Pro Leu Ala  Trp Asp Asn His Tyr  Gly Thr Gln
    1580                1585                1590

Ile Pro  Lys Glu Glu Trp Lys  Ser Gln Glu Lys Ser  Pro Glu Lys
    1595                1600                1605

Thr Ala  Phe Lys Lys Lys Asp  Thr Ile Leu Ser Leu  Asn Ala Cys
    1610                1615                1620

Glu Ser  Asn His Ala Ile Ala  Ala Ile Asn Glu Gly  Gln Asn Lys
    1625                1630                1635

Pro Glu  Ile Glu Val Thr Trp  Ala Lys Gln Gly Arg  Thr Glu Arg
    1640                1645                1650

Leu Cys  Ser Gln Asn Pro Pro  Val Leu Lys Arg His  Gln Arg Glu
    1655                1660                1665

Ile Thr  Arg Thr Thr Leu Gln  Ser Asp Gln Glu Glu  Ile Asp Tyr
    1670                1675                1680

Asp Asp  Thr Ile Ser Val Glu  Met Lys Lys Glu Asp  Phe Asp Ile
    1685                1690                1695

Tyr Asp  Glu Asp Glu Asn Gln  Ser Pro Arg Ser Phe  Gln Lys Lys
    1700                1705                1710

Thr Arg  His Tyr Phe Ile Ala  Ala Val Glu Arg Leu  Trp Asp Tyr
    1715                1720                1725

Gly Met  Ser Ser Ser Pro His  Val Leu Arg Asn Arg  Ala Gln Ser
    1730                1735                1740

Gly Ser  Val Pro Gln Phe Lys  Lys Val Val Phe Gln  Glu Phe Thr
    1745                1750                1755

Asp Gly  Ser Phe Thr Gln Pro  Leu Tyr Arg Gly Glu  Leu Asn Glu
    1760                1765                1770

His Leu  Gly Leu Leu Gly Pro  Tyr Ile Arg Ala Glu  Val Glu Asp
    1775                1780                1785

Asn Ile  Met Val Thr Phe Arg  Asn Gln Ala Ser Arg  Pro Tyr Ser
    1790                1795                1800

Phe Tyr  Ser Ser Leu Ile Ser  Tyr Glu Glu Asp Gln  Arg Gln Gly
    1805                1810                1815

Ala Glu  Pro Arg Lys Asn Phe  Val Lys Pro Asn Glu  Thr Lys Thr
    1820                1825                1830

Tyr Phe  Trp Lys Val Gln His  His Met Ala Pro Thr  Lys Asp Glu
    1835                1840                1845

Phe Asp  Cys Lys Ala Trp Ala  Tyr Phe Ser Asp Val  Asp Leu Glu
    1850                1855                1860

Lys Asp  Val His Ser Gly Leu  Ile Gly Pro Leu Leu  Val Cys His
    1865                1870                1875

Thr Asn  Thr Leu Asn Pro Ala  His Gly Arg Gln Val  Thr Val Gln
    1880                1885                1890

Glu Phe  Ala Leu Phe Phe Thr  Ile Phe Asp Glu Thr  Lys Ser Trp
    1895                1900                1905

Tyr Phe  Thr Glu Asn Met Glu  Arg Asn Cys Arg Ala  Pro Cys Asn
    1910                1915                1920

Ile Gln  Met Glu Asp Pro Thr  Phe Lys Glu Asn Tyr  Arg Phe His
    1925                1930                1935
```

```
Ala Ile  Asn Gly Tyr Ile Met  Asp Thr Leu Pro Gly  Leu Val Met
    1940                 1945                 1950

Ala Gln  Asp Gln Arg Ile Arg  Trp Tyr Leu Leu Ser  Met Gly Ser
    1955                 1960                 1965

Asn Glu  Asn Ile His Ser Ile  His Phe Ser Gly His  Val Phe Thr
    1970                 1975                 1980

Val Arg  Lys Lys Glu Glu Tyr  Lys Met Ala Leu Tyr  Asn Leu Tyr
    1985                 1990                 1995

Pro Gly  Val Phe Glu Thr Val  Glu Met Leu Pro Ser  Lys Ala Gly
    2000                 2005                 2010

Ile Trp  Arg Val Glu Cys Leu  Ile Gly Glu His Leu  His Ala Gly
    2015                 2020                 2025

Met Ser  Thr Leu Phe Leu Val  Tyr Ser Asn Lys Cys  Gln Thr Pro
    2030                 2035                 2040

Leu Gly  Met Ala Ser Gly His  Ile Arg Asp Phe Gln  Ile Thr Ala
    2045                 2050                 2055

Ser Gly  Gln Tyr Gly Gln Trp  Ala Pro Lys Leu Ala  Arg Leu His
    2060                 2065                 2070

Tyr Ser  Gly Ser Ile Asn Ala  Trp Ser Thr Lys Glu  Pro Phe Ser
    2075                 2080                 2085

Trp Ile  Lys Val Asp Leu Leu  Ala Pro Met Ile Ile  His Gly Ile
    2090                 2095                 2100

Lys Thr  Gln Gly Ala Arg Gln  Lys Phe Ser Ser Leu  Tyr Ile Ser
    2105                 2110                 2115

Gln Phe  Ile Ile Met Tyr Ser  Leu Asp Gly Lys Lys  Trp Gln Thr
    2120                 2125                 2130

Tyr Arg  Gly Asn Ser Thr Gly  Thr Leu Met Val Phe  Phe Gly Asn
    2135                 2140                 2145

Val Asp  Ser Ser Gly Ile Lys  His Asn Ile Phe Asn  Pro Pro Ile
    2150                 2155                 2160

Ile Ala  Arg Tyr Ile Arg Leu  His Pro Thr His Tyr  Ser Ile Arg
    2165                 2170                 2175

Ser Thr  Leu Arg Met Glu Leu  Met Gly Cys Asp Leu  Asn Ser Cys
    2180                 2185                 2190

Ser Met  Pro Leu Gly Met Glu  Ser Lys Ala Ile Ser  Asp Ala Gln
    2195                 2200                 2205

Ile Thr  Ala Ser Ser Tyr Phe  Thr Asn Met Phe Ala  Thr Trp Ser
    2210                 2215                 2220

Pro Ser  Lys Ala Arg Leu His  Leu Gln Gly Arg Ser  Asn Ala Trp
    2225                 2230                 2235

Arg Pro  Gln Val Asn Asn Pro  Lys Glu Trp Leu Gln  Val Asp Phe
    2240                 2245                 2250

Gln Lys  Thr Met Lys Val Thr  Gly Val Thr Thr Gln  Gly Val Lys
    2255                 2260                 2265

Ser Leu  Leu Thr Ser Met Tyr  Val Lys Glu Phe Leu  Ile Ser Ser
    2270                 2275                 2280

Ser Gln  Asp Gly His Gln Trp  Thr Leu Phe Phe Gln  Asn Gly Lys
    2285                 2290                 2295

Val Lys  Val Phe Gln Gly Asn  Gln Asp Ser Phe Thr  Pro Val Val
    2300                 2305                 2310

Asn Ser  Leu Asp Pro Pro Leu  Leu Thr Arg Tyr Leu  Arg Ile His
    2315                 2320                 2325
```

```
Pro Gln  Ser Trp Val His Gln  Ile Ala Leu Arg Met  Glu Val Leu
    2330                 2335                 2340

Gly Cys  Glu Ala Gln Asp Leu  Tyr Asp Lys Thr His  Thr Cys Pro
    2345                 2350                 2355

Pro Cys  Pro Ala Pro Glu Leu  Leu Gly Gly Pro Ser  Val Phe Leu
    2360                 2365                 2370

Phe Pro  Pro Lys Pro Lys Asp  Thr Leu Met Ile Ser  Arg Thr Pro
    2375                 2380                 2385

Glu Val  Thr Cys Val Val Val  Asp Val Ser His Glu  Asp Pro Glu
    2390                 2395                 2400

Val Lys  Phe Asn Trp Tyr Val  Asp Gly Val Glu Val  His Asn Ala
    2405                 2410                 2415

Lys Thr  Lys Pro Arg Glu Glu  Gln Tyr Asn Ser Thr  Tyr Arg Val
    2420                 2425                 2430

Val Ser  Val Leu Thr Val Leu  His Gln Asp Trp Leu  Asn Gly Lys
    2435                 2440                 2445

Glu Tyr  Lys Cys Lys Val Ser  Asn Lys Ala Leu Pro  Ala Pro Ile
    2450                 2455                 2460

Glu Lys  Thr Ile Ser Lys Ala  Lys Gly Gln Pro Arg  Glu Pro Gln
    2465                 2470                 2475

Val Tyr  Thr Leu Pro Pro Ser  Arg Asp Glu Leu Thr  Lys Asn Gln
    2480                 2485                 2490

Val Ser  Leu Thr Cys Leu Val  Lys Gly Phe Tyr Pro  Ser Asp Ile
    2495                 2500                 2505

Ala Val  Glu Trp Glu Ser Asn  Gly Gln Pro Glu Asn  Asn Tyr Lys
    2510                 2515                 2520

Thr Thr  Pro Pro Val Leu Asp  Ser Asp Gly Ser Phe  Phe Leu Tyr
    2525                 2530                 2535

Ser Lys  Leu Thr Val Asp Lys  Ser Arg Trp Gln Gln  Gly Asn Val
    2540                 2545                 2550

Phe Ser  Cys Ser Val Met His  Glu Ala Leu His Asn  His Tyr Thr
    2555                 2560                 2565

Gln Lys  Ser Leu Ser Leu Ser  Pro Gly Lys
    2570                 2575
```

<210> SEQ ID NO 7
<211> LENGTH: 5055
<212> TYPE: DNA
<213> ORGANISM: Artificial Sequence
<220> FEATURE:
<223> OTHER INFORMATION: SC BDD FVIIIFc

<400> SEQUENCE: 7

```
atgcaaatag agctctccac ctgcttcttt ctgtgccttt tgcgattctg ctttagtgcc      60

accagaagat actacctggg tgcagtggaa ctgtcatggg actatatgca aagtgatctc     120

ggtgagctgc ctgtggacgc aagatttcct cctagagtgc caaaatcttt tccattcaac     180

acctcagtcg tgtacaaaaa gactctgttt gtagaattca cggatcacct tttcaacatc     240

gctaagccaa ggccaccctg gatgggtctg ctaggtccta ccatccaggc tgaggtttat     300

gatacagtgg tcattacact taagaacatg gcttcccatc ctgtcagtct tcatgctgtt     360

ggtgtatcct actggaaagc ttctgaggga gctgaatatg atgatcagac cagtcaaagg     420

gagaaagaag atgataaagt cttccctggt ggaagccata catatgtctg gcaggtcctg     480

aaagagaatg gtccaatggc ctctgaccca ctgtgcctta cctactcata tctttctcat     540
```

-continued

```
gtggacctgg taaaagactt gaattcaggc ctcattggag ccctactagt atgtagagaa    600
gggagtctgg ccaaggaaaa gacacagacc ttgcacaaat ttatactact ttttgctgta    660
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag gaaccccaac tacgaatgaa aaataatgaa   1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatatacctt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctctcaaa acccaccagt cttgaaagcc catcaggcgg aaataactcg tactactctt   2340
cagtcagatc aagaggaaat tgactatgat gataccatat cagttgaaat gaagaaggaa   2400
gattttgaca tttatgatga ggatgaaaat cagagccccc gcagctttca aaagaaaaca   2460
cgacactatt ttattgctgc agtggagagg ctctgggatt atgggatgag tagctcccca   2520
catgttctaa gaaacagggc tcagagtggc agtgtccctc agttcaagaa agttgttttc   2580
caggaattta ctgatggctc ctttactcag cccttatacc gtggagaact aaatgaacat   2640
ttgggactcc tggggccata tataagagca gaagttgaag ataatatcat ggtaactttc   2700
agaaatcagg cctctcgtcc ctattccttc tattctagcc ttatttctta tgaggaagat   2760
cagaggcaag gagcagaacc tagaaaaaac tttgtcaagc ctaatgaaac caaaacttac   2820
ttttggaaag tgcaacatca tatggcaccc actaaagatg agtttgactg caaagcctgg   2880
gcttatttct ctgatgttga cctggaaaaa gatgtgcact caggcctgat tggacccctt   2940
```

```
ctggtctgcc acactaacac actgaaccct gctcatggga gacaagtgac agtacaggaa   3000
tttgctctgt ttttcaccat ctttgatgag accaaaagct ggtacttcac tgaaaatatg   3060
gaaagaaact gcagggctcc ctgcaatatc cagatggaag atcccacttt taaagagaat   3120
tatcgcttcc atgcaatcaa tggctacata atggatacac tacctggctt agtaatggct   3180
caggatcaaa ggattcgatg gtatctgctc agcatgggca gcaatgaaaa catccattct   3240
attcatttca gtggacatgt gttcactgta cgaaaaaaag aggagtataa aatggcactg   3300
tacaatctct atccaggtgt ttttgagaca gtggaaatgt taccatccaa agctggaatt   3360
tggcgggtgg aatgccttat tggcgagcat ctacatgctg ggatgagcac actttttctg   3420
gtgtacagca ataagtgtca gactcccctg ggaatggctt ctggacacat tagagatttt   3480
cagattacag cttcaggaca atatggacag tgggccccaa agctggccag acttcattat   3540
tccggatcaa tcaatgcctg gagcaccaag gagccctttt cttggatcaa ggtggatctg   3600
ttggcaccaa tgattattca cggcatcaag acccagggtg cccgtcagaa gttctccagc   3660
ctctacatct ctcagtttat catcatgtat agtcttgatg ggaagaagtg gcagacttat   3720
cgaggaaatt ccactggaac cttaatggtc ttctttggca atgtggattc atctgggata   3780
aaacacaata tttttaaccc tccaattatt gctcgataca tccgtttgca cccaactcat   3840
tatagcattc gcagcactct tcgcatggag ttgatgggct gtgatttaaa tagttgcagc   3900
atgccattgg gaatggagag taaagcaata tcagatgcac agattactgc ttcatcctac   3960
tttaccaata tgtttgccac ctggtctcct tcaaaagctc gacttcacct ccaagggagg   4020
agtaatgcct ggagacctca ggtgaataat ccaaaagagt ggctgcaagt ggacttccag   4080
aagacaatga aagtcacagg agtaactact cagggagtaa aatctctgct taccagcatg   4140
tatgtgaagg agttcctcat ctccagcagt caagatggcc atcagtggac tctctttttt   4200
cagaatggca aagtaaaggt tttcaggga aatcaagact ccttcacacc tgtggtgaac   4260
tctctagacc caccgttact gactcgctac cttcgaattc acccccagag ttgggtgcac   4320
cagattgccc tgaggatgga ggttctgggc tgcgaggcac aggacctcta cgacaaaact   4380
cacacatgcc caccgtgccc agctccagaa ctcctgggcg gaccgtcagt cttcctcttc   4440
cccccaaaac ccaaggacac cctcatgatc tcccggaccc ctgaggtcac atgcgtggtg   4500
gtggacgtga gccacgaaga ccctgaggtc aagttcaact ggtacgtgga cggcgtggag   4560
gtgcataatg ccaagacaaa gccgcgggag gagcagtaca acagcacgta ccgtgtggtc   4620
agcgtcctca ccgtcctgca ccaggactgg ctgaatggca aggagtacaa gtgcaaggtc   4680
tccaacaaag ccctcccagc ccccatcgag aaaaccatct ccaaagccaa agggcagccc   4740
cgagaaccac aggtgtacac cctgccccca tcccgggatg agctgaccaa gaaccaggtc   4800
agcctgacct gcctggtcaa aggcttctat cccagcgaca tcgccgtgga gtgggagagc   4860
aatgggcagc cggagaacaa ctacaagacc acgcctcccg tgttggactc cgacggctcc   4920
ttcttcctct acagcaagct caccgtggac aagagcaggt ggcagcaggg gaacgtcttc   4980
tcatgctccg tgatgcatga ggctctgcac aaccactaca cgcagaagag cctctccctg   5040
tctccgggta aatga                                                    5055
```

<210> SEQ ID NO 8
<211> LENGTH: 1684
<212> TYPE: PRT
<213> ORGANISM: Artificial Sequence
<220> FEATURE:

<223> OTHER INFORMATION: SC BDD FVIIIFc

<400> SEQUENCE: 8

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400
```

```
Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Ala His Gln Ala Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
```

```
            820                 825                 830

Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu  Phe Ala Leu Phe Phe  Thr Ile Phe
        995                 1000                1005

Asp Glu  Thr Lys Ser Trp Tyr  Phe Thr Glu Asn Met  Glu Arg Asn
    1010                1015                1020

Cys Arg  Ala Pro Cys Asn Ile  Gln Met Glu Asp Pro  Thr Phe Lys
    1025                1030                1035

Glu Asn  Tyr Arg Phe His Ala  Ile Asn Gly Tyr Ile  Met Asp Thr
    1040                1045                1050

Leu Pro  Gly Leu Val Met Ala  Gln Asp Gln Arg Ile  Arg Trp Tyr
    1055                1060                1065

Leu Leu  Ser Met Gly Ser Asn  Glu Asn Ile His Ser  Ile His Phe
    1070                1075                1080

Ser Gly  His Val Phe Thr Val  Arg Lys Lys Glu Glu  Tyr Lys Met
    1085                1090                1095

Ala Leu  Tyr Asn Leu Tyr Pro  Gly Val Phe Glu Thr  Val Glu Met
    1100                1105                1110

Leu Pro  Ser Lys Ala Gly Ile  Trp Arg Val Glu Cys  Leu Ile Gly
    1115                1120                1125

Glu His  Leu His Ala Gly Met  Ser Thr Leu Phe Leu  Val Tyr Ser
    1130                1135                1140

Asn Lys  Cys Gln Thr Pro Leu  Gly Met Ala Ser Gly  His Ile Arg
    1145                1150                1155

Asp Phe  Gln Ile Thr Ala Ser  Gly Gln Tyr Gly Gln  Trp Ala Pro
    1160                1165                1170

Lys Leu  Ala Arg Leu His Tyr  Ser Gly Ser Ile Asn  Ala Trp Ser
    1175                1180                1185

Thr Lys  Glu Pro Phe Ser Trp  Ile Lys Val Asp Leu  Leu Ala Pro
    1190                1195                1200

Met Ile  Ile His Gly Ile Lys  Thr Gln Gly Ala Arg  Gln Lys Phe
    1205                1210                1215

Ser Ser  Leu Tyr Ile Ser Gln  Phe Ile Ile Met Tyr  Ser Leu Asp
    1220                1225                1230
```

```
Gly Lys  Lys Trp Gln Thr Tyr  Arg Gly Asn Ser Thr  Gly Thr Leu
    1235                 1240                 1245

Met Val  Phe Phe Gly Asn Val  Asp Ser Ser Gly Ile  Lys His Asn
    1250                 1255                 1260

Ile Phe  Asn Pro Pro Ile Ile  Ala Arg Tyr Ile Arg  Leu His Pro
    1265                 1270                 1275

Thr His  Tyr Ser Ile Arg Ser  Thr Leu Arg Met Glu  Leu Met Gly
    1280                 1285                 1290

Cys Asp  Leu Asn Ser Cys Ser  Met Pro Leu Gly Met  Glu Ser Lys
    1295                 1300                 1305

Ala Ile  Ser Asp Ala Gln Ile  Thr Ala Ser Ser Tyr  Phe Thr Asn
    1310                 1315                 1320

Met Phe  Ala Thr Trp Ser Pro  Ser Lys Ala Arg Leu  His Leu Gln
    1325                 1330                 1335

Gly Arg  Ser Asn Ala Trp Arg  Pro Gln Val Asn Asn  Pro Lys Glu
    1340                 1345                 1350

Trp Leu  Gln Val Asp Phe Gln  Lys Thr Met Lys Val  Thr Gly Val
    1355                 1360                 1365

Thr Thr  Gln Gly Val Lys Ser  Leu Leu Thr Ser Met  Tyr Val Lys
    1370                 1375                 1380

Glu Phe  Leu Ile Ser Ser Ser  Gln Asp Gly His Gln  Trp Thr Leu
    1385                 1390                 1395

Phe Phe  Gln Asn Gly Lys Val  Lys Val Phe Gln Gly  Asn Gln Asp
    1400                 1405                 1410

Ser Phe  Thr Pro Val Val Asn  Ser Leu Asp Pro Pro  Leu Leu Thr
    1415                 1420                 1425

Arg Tyr  Leu Arg Ile His Pro  Gln Ser Trp Val His  Gln Ile Ala
    1430                 1435                 1440

Leu Arg  Met Glu Val Leu Gly  Cys Glu Ala Gln Asp  Leu Tyr Asp
    1445                 1450                 1455

Lys Thr  His Thr Cys Pro Pro  Cys Pro Ala Pro Glu  Leu Leu Gly
    1460                 1465                 1470

Gly Pro  Ser Val Phe Leu Phe  Pro Pro Lys Pro Lys  Asp Thr Leu
    1475                 1480                 1485

Met Ile  Ser Arg Thr Pro Glu  Val Thr Cys Val Val  Val Asp Val
    1490                 1495                 1500

Ser His  Glu Asp Pro Glu Val  Lys Phe Asn Trp Tyr  Val Asp Gly
    1505                 1510                 1515

Val Glu  Val His Asn Ala Lys  Thr Lys Pro Arg Glu  Glu Gln Tyr
    1520                 1525                 1530

Asn Ser  Thr Tyr Arg Val Val  Ser Val Leu Thr Val  Leu His Gln
    1535                 1540                 1545

Asp Trp  Leu Asn Gly Lys Glu  Tyr Lys Cys Lys Val  Ser Asn Lys
    1550                 1555                 1560

Ala Leu  Pro Ala Pro Ile Glu  Lys Thr Ile Ser Lys  Ala Lys Gly
    1565                 1570                 1575

Gln Pro  Arg Glu Pro Gln Val  Tyr Thr Leu Pro Pro  Ser Arg Asp
    1580                 1585                 1590

Glu Leu  Thr Lys Asn Gln Val  Ser Leu Thr Cys Leu  Val Lys Gly
    1595                 1600                 1605

Phe Tyr  Pro Ser Asp Ile Ala  Val Glu Trp Glu Ser  Asn Gly Gln
    1610                 1615                 1620
```

```
Pro Glu  Asn Asn Tyr Lys Thr  Thr Pro Pro Val Leu  Asp Ser Asp
    1625                 1630                 1635

Gly Ser  Phe Phe Leu Tyr Ser  Lys Leu Thr Val Asp  Lys Ser Arg
    1640                 1645                 1650

Trp Gln  Gln Gly Asn Val Phe  Ser Cys Ser Val Met  His Glu Ala
    1655                 1660                 1665

Leu His  Asn His Tyr Thr Gln  Lys Ser Leu Ser Leu  Ser Pro Gly
    1670                 1675                 1680

Lys


<210> SEQ ID NO 9
<211> LENGTH: 32
<212> TYPE: PRT
<213> ORGANISM: Artificial Sequence
<220> FEATURE:
<223> OTHER INFORMATION: CTP peptide 1

<400> SEQUENCE: 9

Asp Pro Arg Phe Gln Asp Ser Ser Ser Ser Lys Ala Pro Pro Pro Ser
1               5                   10                  15

Leu Pro Ser Pro Ser Arg Leu Pro Gly Pro Ser Asp Thr Pro Ile Leu
            20                  25                  30


<210> SEQ ID NO 10
<211> LENGTH: 28
<212> TYPE: PRT
<213> ORGANISM: Artificial Sequence
<220> FEATURE:
<223> OTHER INFORMATION: CTP peptide 2

<400> SEQUENCE: 10

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
            20                  25


<210> SEQ ID NO 11
<211> LENGTH: 20
<212> TYPE: PRT
<213> ORGANISM: Artificial Sequence
<220> FEATURE:
<223> OTHER INFORMATION: PAS peptide 1

<400> SEQUENCE: 11

Ala Ser Pro Ala Ala Pro Ala Pro Ala Ser Pro Ala Ala Pro Ala Pro
1               5                   10                  15

Ser Ala Pro Ala
            20


<210> SEQ ID NO 12
<211> LENGTH: 20
<212> TYPE: PRT
<213> ORGANISM: Artificial Sequence
<220> FEATURE:
<223> OTHER INFORMATION: PAS peptide 2

<400> SEQUENCE: 12

Ala Ala Pro Ala Ser Pro Ala Pro Ala Ala Pro Ser Ala Pro Ala Pro
1               5                   10                  15

Ala Ala Pro Ser
            20
```

<210> SEQ ID NO 13
<211> LENGTH: 20
<212> TYPE: PRT
<213> ORGANISM: Artificial Sequence
<220> FEATURE:
<223> OTHER INFORMATION: PAS peptide 3

<400> SEQUENCE: 13

```
Ala Pro Ser Ser Pro Ser Pro Ser Ala Pro Ser Ser Pro Ser Pro Ala
1               5                   10                  15

Ser Pro Ser Ser
            20
```

<210> SEQ ID NO 14
<211> LENGTH: 19
<212> TYPE: PRT
<213> ORGANISM: Artificial Sequence
<220> FEATURE:
<223> OTHER INFORMATION: PAS peptide 4

<400> SEQUENCE: 14

```
Ala Pro Ser Ser Pro Ser Pro Ser Ala Pro Ser Ser Pro Ser Pro Ala
1               5                   10                  15

Ser Pro Ser
```

<210> SEQ ID NO 15
<211> LENGTH: 20
<212> TYPE: PRT
<213> ORGANISM: Artificial Sequence
<220> FEATURE:
<223> OTHER INFORMATION: PAS peptide 5

<400> SEQUENCE: 15

```
Ser Ser Pro Ser Ala Pro Ser Pro Ser Ser Pro Ala Ser Pro Ser Pro
1               5                   10                  15

Ser Ser Pro Ala
            20
```

<210> SEQ ID NO 16
<211> LENGTH: 24
<212> TYPE: PRT
<213> ORGANISM: Artificial Sequence
<220> FEATURE:
<223> OTHER INFORMATION: PAS peptide 6

<400> SEQUENCE: 16

```
Ala Ala Ser Pro Ala Ala Pro Ser Ala Pro Pro Ala Ala Ala Ser Pro
1               5                   10                  15

Ala Ala Pro Ser Ala Pro Pro Ala
            20
```

<210> SEQ ID NO 17
<211> LENGTH: 20
<212> TYPE: PRT
<213> ORGANISM: Artificial Sequence
<220> FEATURE:
<223> OTHER INFORMATION: PAS peptide 7

<400> SEQUENCE: 17

```
Ala Ser Ala Ala Ala Pro Ala Ala Ala Ser Ala Ala Ala Ser Ala Pro
1               5                   10                  15

Ser Ala Ala Ala
            20
```

<210> SEQ ID NO 18
<211> LENGTH: 4
<212> TYPE: PRT
<213> ORGANISM: Artificial Sequence
<220> FEATURE:
<223> OTHER INFORMATION: amino acids 233-236 of human IgG1

<400> SEQUENCE: 18

Glu Leu Leu Gly
1

<210> SEQ ID NO 19
<211> LENGTH: 11
<212> TYPE: PRT
<213> ORGANISM: Artificial Sequence
<220> FEATURE:
<223> OTHER INFORMATION: Ig peptide 1

<400> SEQUENCE: 19

Pro Lys Asn Ser Ser Met Ile Ser Asn Thr Pro
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Ig peptide 2

<400> SEQUENCE: 20

His Gln Ser Leu Gly Thr Gln
1               5

<210> SEQ ID NO 21
<211> LENGTH: 8
<212> TYPE: PRT
<213> ORGANISM: Artificial Sequence
<220> FEATURE:
<223> OTHER INFORMATION: Ig peptide 3

<400> SEQUENCE: 21

His Gln Asn Leu Ser Asp Gly Lys
1               5

<210> SEQ ID NO 22
<211> LENGTH: 8
<212> TYPE: PRT
<213> ORGANISM: Artificial Sequence
<220> FEATURE:
<223> OTHER INFORMATION: Ig peptide 4

<400> SEQUENCE: 22

His Gln Asn Ile Ser Asp Gly Lys
1               5

<210> SEQ ID NO 23
<211> LENGTH: 8
<212> TYPE: PRT
<213> ORGANISM: Artificial Sequence
<220> FEATURE:
<223> OTHER INFORMATION: Ig peptide 5

<400> SEQUENCE: 23

Val Ile Ser Ser His Leu Gly Gln
1               5

<210> SEQ ID NO 24

```
<211> LENGTH: 20
<212> TYPE: DNA
<213> ORGANISM: Artificial Sequence
<220> FEATURE:
<223> OTHER INFORMATION: pBUD-BDDF8 BamH1-2565F

<400> SEQUENCE: 24

gcttgaggat ccagagttcc                                              20


<210> SEQ ID NO 25
<211> LENGTH: 35
<212> TYPE: DNA
<213> ORGANISM: Artificial Sequence
<220> FEATURE:
<223> OTHER INFORMATION: BDDF8-R1645A/R1648A-R

<400> SEQUENCE: 25

cgagttattt ccgcctgatg ggctttcaag actgg                             35


<210> SEQ ID NO 26
<211> LENGTH: 35
<212> TYPE: DNA
<213> ORGANISM: Artificial Sequence
<220> FEATURE:
<223> OTHER INFORMATION: BDDF8-R1645A/R1648A-F

<400> SEQUENCE: 26

ccagtcttga aagcccatca ggcggaaata actcg                             35


<210> SEQ ID NO 27
<211> LENGTH: 22
<212> TYPE: DNA
<213> ORGANISM: Artificial Sequence
<220> FEATURE:
<223> OTHER INFORMATION: pBUD-BDDF8 Kpn21-4245R

<400> SEQUENCE: 27

tgattgatcc ggaataatga ag                                           22


<210> SEQ ID NO 28
<211> LENGTH: 11
<212> TYPE: PRT
<213> ORGANISM: Artificial Sequence
<220> FEATURE:
<223> OTHER INFORMATION: albumin binding peptide

<400> SEQUENCE: 28

Asp Ile Cys Leu Pro Arg Trp Gly Cys Leu Trp
                5                   10
```

CELL LINE EXPRESSING SINGLE CHAIN FACTOR VIII POLYPEPTIDES AND USES THEREOF

REFERENCE TO A SEQUENCE LISTING SUBMITTED ELECTRONICALLY

The content of the electronically submitted sequence listing (Name: 2159_3950001_SequenceListing.txt; Size: 85,467 bytes; and Date of Creation: Jan. 2, 2015) is herein incorporated by reference in its entirety.

FIELD OF THE INVENTION

The present invention relates generally to the field of therapeutics for hemostatic disorders.

BACKGROUND ART

Hemophilia A is an X-linked bleeding disorder caused by mutations and/or deletions in the factor VIII (FVIII) gene resulting in a deficiency of FVIII activity (Peyvandi, F. et al. *Haemophilia* 12:82-89 (2006). The disease is characterized by spontaneous hemorrhage and excessive bleeding after trauma. Over time, the repeated bleeding into muscles and joints, which often begins in early childhood, results in hemophilic arthropathy and irreversible joint damage. This damage is progressive and can lead to severely limited mobility of joints, muscle atrophy and chronic pain (Rodriguez-Merchan, E. C., *Semin. Thromb. Hemost.* 29:87-96 (2003), which is herein incorporated by reference in its entirety).

The human factor VIII gene was isolated and expressed in mammalian cells (Toole, J. J., et al., *Nature* 312:342-347 (1984); Gitschier, J., et al., *Nature* 312:326-330 (1984); Wood, W. I., et al., *Nature* 312:330-337 (1984); Vehar, G. A., et al., *Nature* 312:337-342 (1984); WO 87/04187; WO 88/08035; WO 88/03558; U.S. Pat. No. 4,757,006), each of which is incorporated herein by reference in its entirety, and the amino acid sequence was deduced from cDNA. Capon et al., U.S. Pat. No. 4,965,199, incorporated herein by reference in its entirety, discloses a recombinant DNA method for producing factor VIII in mammalian host cells and purification of human factor VIII. Human factor VIII expression in CHO (Chinese hamster ovary) cells and BHK (baby hamster kidney cells) has been reported. Human factor VIII has been modified to delete part or all of the B domain (U.S. Pat. Nos. 4,994,371 and 4,868,112; Toole J J, et al., Proc. Natl. Acad. Sci. USA. 1986; 83: 5939-5942; and Sandberg H, et al., Seminars in Hematology 2001; 38(2 Suppl 4): 4-12, each of which is incorporated herein by reference in its entirety), and replacement of the human factor VIII B domain with the human factor V B domain has been performed (U.S. Pat. No. 5,004,803, incorporated herein by reference in its entirety). The cDNA sequence encoding human factor VIII and predicted amino acid sequence are shown in SEQ ID NOs:1 and 2, respectively, of US Application Publ. No. 2005/0100990, incorporated herein by reference in its entirety.

A number of functional factor VIII molecules, including B-domain deletions, are disclosed in the following U.S. Pat. No. 6,316,226 and U.S. Pat. No. 6,346,513, both assigned to Baxter; U.S. Pat. No. 7,041,635 assigned to In2Gen; U.S. Pat. No. 5,789,203, U.S. Pat. No. 6,060,447, U.S. Pat. No. 5,595,886, and U.S. Pat. No. 6,228,620 assigned to Chiron; U.S. Pat. No. 5,972,885 and U.S. Pat. No. 6,048,720 assigned to Biovitrum, U.S. Pat. No. 5,543,502 and U.S. Pat. No. 5,610,278 assigned to Novo Nordisk; U.S. Pat. No. 5,171,844 assigned to Immuno Ag; U.S. Pat. No. 5,112,950 assigned to Transgene S.A.; U.S. Pat. No. 4,868,112 assigned to Genetics Institute, each of which is incorporated herein by reference in its entirety.

Treatment of hemophilia A is by replacement therapy targeting restoration of FVIII activity to 1 to 5% of normal levels to prevent spontaneous bleeding (Mannucci, P. M., et al., *N. Engl. J. Med.* 344:1773-1779 (2001), which is herein incorporated by reference in its entirety). There are plasma-derived and recombinant FVIII products available to treat bleeding episodes on-demand or to prevent bleeding episodes from occurring by treating prophylactically. Based on the short half-life of these products, however, e.g., 8-12 hours, treatment regimens require the administration of frequent intravenous injections. Such frequent administration is painful and inconvenient.

Reduced mortality, prevention of joint damage, and improved quality of life have been important achievements due to the development of plasma-derived and recombinant FVIII. Prolonged protection from bleeding would represent another key advancement in the treatment of hemophilia A patients. However, to date, no products that allow for prolonged hemostatic protection have been developed. Therefore, there remains a need for improved methods of treating hemophilia due to factor VIII deficiency that are more tolerable, longer lasting, and more effective than current therapies.

BRIEF SUMMARY OF THE INVENTION

Certain aspects of the application are directed to an isolated cell line comprising a recombinant vector encoding a single chain FVIII polypeptide.

In certain embodiments, the cell line further comprises an antisense polynucleotide specific for a FVIII polypeptide processing enzyme.

In some embodiments, the cell line is a mammalian cell line. In one embodiment, the mammalian cell line is selected from the group consisting of HEK293 cells, CHO cells, BHK cells, and HeLa cells.

In some embodiments, the single chain FVIII polypeptide of the application comprises one or more amino acid substitutions in the processing domain which inhibits cleavage by a FVIII processing enzyme. In one embodiment, the one or more amino acid substitutions correspond to R1645A or R1648A of full-length Factor VIII or both. In some embodiments, the single chain FVIII polypeptide comprises one or more intact intracellular processing sites. In some embodiments, the FVIII processing enzyme is selected from the group consisting of PACE/furin, PC5, and PC7. In some embodiments, the single chain FVIII polypeptide comprises a full or partial deletion of the B domain.

In certain embodiments, a single chain FVIII polypeptide of the invention comprises: Formula I: (A1)-(A2)-[B]-(A3)-(C1)-(C2); wherein, a) A1 is an A1 domain of FVIII; b) A2 is an A2 domain of FVIII; c) [B] is a B domain of FVIII, a fragment thereof, or is deleted; d) A3 is an A3 domain of FVIII; e) C1 is a C1 domain of FVIII; and f) C2 is a C2 domain of FVIII; and wherein the single chain FVIII polypeptide exhibits procoagulation activity. In one embodiment, the A1 domain and the A3 domain are connected by a metal ion mediated interaction, e.g., a metal-ion mediate noncovalent bond.

In certain embodiments, the single chain FVIII polypeptide comprises a sequence at least 90% or 95% identical to a Factor VIII amino acid sequence comprising SEQ ID NO: 8.

In some embodiments, the single chain FVIII polypeptide further comprises a heterologous moiety. In some embodiments, the heterologous moiety is a half-life extending moiety. In another embodiment, the half-life extending moiety is an immunoglobulin constant region or a portion thereof, albumin, albumin binding polypeptide, PAS, the C-terminal peptide (CTP) of the β subunit of human chorionic gonadotropin, polyethylene glycol (PEG), hydroxyethyl starch (HES), albumin-binding small molecules, or combinations thereof. In one embodiment, the immunoglobulin constant region or a portion thereof is an Fc region.

Another aspect of the application is directed to a composition comprising the cell line or the single chain FVIII polypeptide of the application and a pharmaceutically acceptable carrier.

Another aspect of the application is directed to a method for producing a single chain FVIII polypeptide comprising culturing the cell line of the application under conditions sufficient for production of said single chain FVIII polypeptide.

Another aspect of the application is directed to a method for producing a cell line that produces a single chain FVIII polypeptide comprising the steps of: (a) contacting a host cell with a polynucleotide comprising a nucleotide sequence encoding the single chain FVIII polypeptide of the application; (b) isolating a cell line producing the single chain FVIII polypeptide. In another embodiment, the method for producing a cell line further comprises (c) propagating the cell line to produce the single chain FVIII polypeptide. In some embodiments, the host cell is a mammalian cell. In one embodiment, the mammalian cell line is selected from the group consisting of HEK293 cells, CHO cells, BHK cells, and HeLa cells.

Another aspect of the application is directed to a polynucleotide encoding a single chain FVIII polypeptide of the application.

Another aspect of the application is directed to a vector comprising a polynucleotide of the application.

Another aspect of the application is directed to a composition comprising a single chain FVIII polypeptide, a polynucleotide, or the vector of the application and a pharmaceutically acceptable carrier.

Another aspect of the application is directed to a method of preventing, treating, ameliorating, or managing a clotting disease or condition in a patient in need thereof by administering an effective amount of the pharmaceutical composition of the application.

Another aspect of the application is directed to a method for diagnosing or imaging a clotting disease or condition in a patient with the composition of the application.

BRIEF DESCRIPTION OF THE DRAWINGS/FIGURES

FIG. 1. Schematic representation of full length Factor VIII proteolytic processing. Initial translated FVIII protein is cleaved intracellularly after Arg 1313 and Arg 1648. The resulting heterodimer is primarily a 200 kDa heavy chain (A1-A2-B) and 80 kDa light chain (A3-C1-C2). Heterogeneity of processing varies the heavy chain from 200 to 90 kDa. The heavy and light chains remain noncovalently associated through the A1 and A3 domains in a metal-ion dependent manner.

Figure 2:
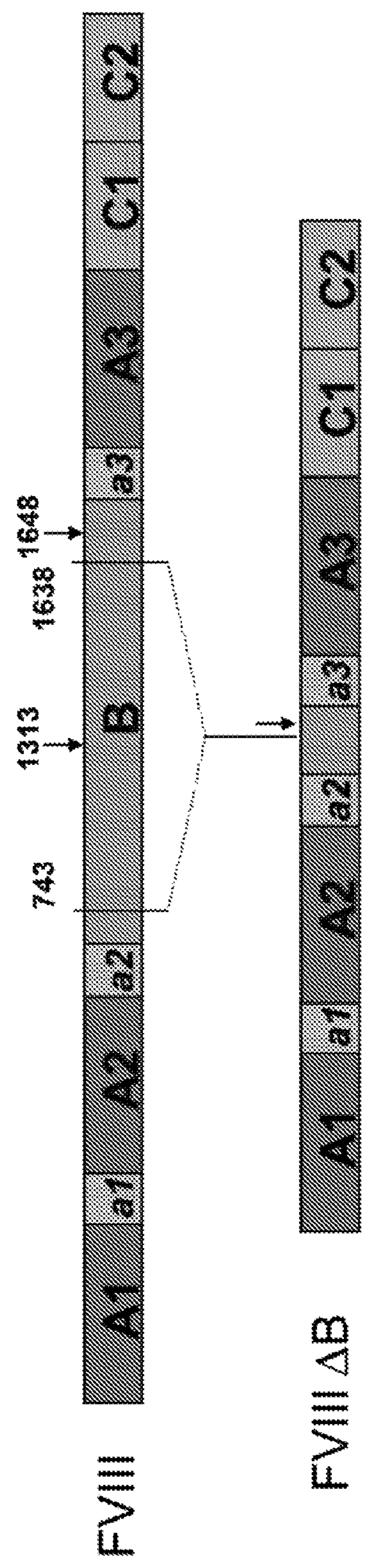

FIG. 2. Schematic representation of a B Domain Deleted (BDD) Factor VIII construct. Fusion of S743 to Q1638 removes 38% of FVIII, and retains only 14 aa of the B domain. Removal of B domain results in fully active FVIII molecule. This BDD preserves intracellular processing site R754 (R1648 of full length sequence), and can produce a heterodimer of 90 kDa HC with 80 kDa LC.

Figure 3:
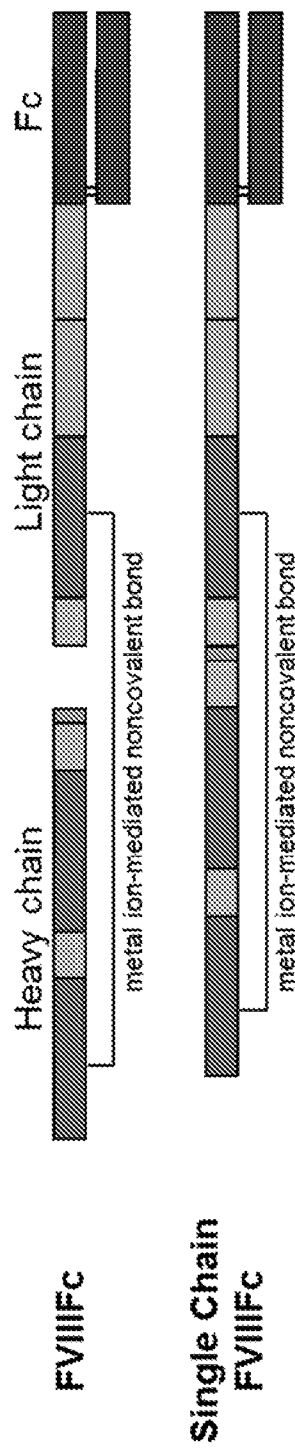

FIG. 3. Schematic representation of processed rFVIIIFc compared to single chain rFVIIIFc.

Figure 4:
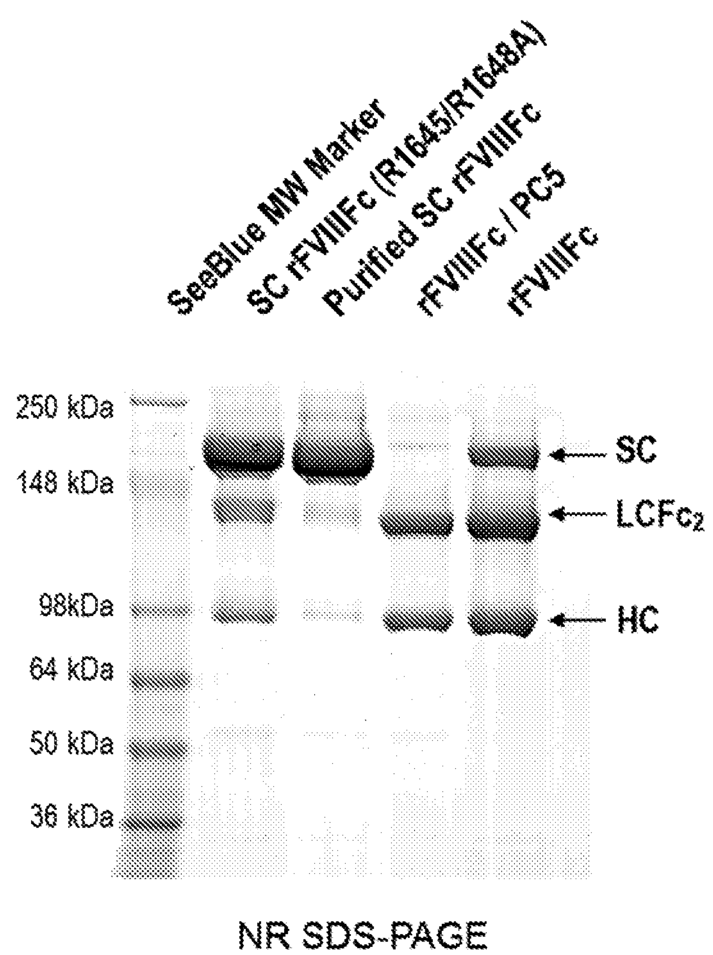

FIG. 4. Nonreduced (NR) SDS-PAGE gel visualized with Sypro Ruby staining showing recombinant single chain FVIIIFc (R1645A/R1648A) produced from 1E11 cell line (lane 2), wild type rFVIIIFc containing 75% processed and 25% single chain FVIIIFc produced from 3C4 clone 22 cell line (lane 5), single chain rFVIIIFc purified from the mixture in lane 5 (lane 3), and fully processed rFVIIIFc produced from the 3C4 clone 22 cell line cotransfected with PC5 (lane 4). The Single Chain (SC), Light Chain $Fc_2$ ($LCFc_2$), and Heavy Chain (HC) bands are labeled. Lane 1 contains SeeBlue molecular weight markers (Invitrogen).

DETAILED DESCRIPTION OF THE INVENTION

The present invention provides cell lines for producing single chain FVIII polypeptides, e.g., chimeric single chain FVIII polypeptides, methods of producing single chain FVIII polypeptides, single chain FVIII polypeptides, and methods of treating Hemophilia A with a single chain Factor VIII polypeptide.

In order to help define this invention, the following terms and definitions are provided.

It is to be noted that the teem "a" or "an" entity refers to one or more of that entity. For example, "an isolated cell" is understood to represent one or more isolated cells. As such, the terms "a" (or "an"), "one or more," and "at least one" can be used interchangeably herein.

"About," as used herein for a range, modifies both ends of the range. Thus, "about 10-20" means "about 10 to about 20."

"Culture," "to culture" and "culturing," as used herein, means to incubate cells under in vitro conditions that allow for cell growth or division or to maintain cells in a living state. "Cultured cells," as used herein, means cells that are propagated in vitro. In certain embodiments, mammalian cell culture is used for expressing exogenous DNA to produce a functional single chain FVIII polypeptides disclosed in this application.

As used herein, "host cell" includes an individual cell or cell culture, which can be or has been a recipient of a vector, e.g., an expression vector, of the invention. Host cells include progeny of a single host cell, and the progeny can not necessarily be completely identical (in morphology or in total DNA complement) to the original parent cell due to natural, accidental, or deliberate mutation and/or change. A host cell includes cells transfected or infected with a vector comprising a polynucleotide encoding, e.g., a single chain Factor VIII polypeptide of the invention.

As used herein, "purified" or "isolated" molecule refers to biological molecules that are removed from their natural environment and are isolated or separated from other components with which they are naturally associated.

"Polypeptide," "peptide" and "protein" are used interchangeably and refer to a polymeric compound comprised of covalently linked amino acid residues.

"Polynucleotide" and "nucleic acid" are used interchangeably and refer to a polymeric compound comprised of covalently linked nucleotide residues.

Polynucleotides can be DNA, cDNA, RNA, single stranded, or double stranded, vectors, plasmids, phage, or viruses.

"Variant," as used herein, refers to a polynucleotide or polypeptide differing from the original polynucleotide or polypeptide, but retaining essential properties thereof, e.g., factor VIII coagulant activity or Fc (FcRn binding) activity. Generally, variants are overall closely similar, and, in many regions, identical to the original polynucleotide or polypeptide. Variants include, e.g., polypeptide and polynucleotide fragments, deletions, insertions, substitutions and modified versions of original polypeptides.

"Factor VIII," as used herein, means a functional factor VIII polypeptide in its normal role in coagulation, unless otherwise specified. Thus, the term Factor VIII includes variant polypeptides that are functional. Similarly, single chain FVIII polypeptides include functional variants thereof. Factor VIII proteins can be the human, porcine, canine, and murine factor VIII proteins. As described in the Background Art section, the full length polypeptide and polynucleotide sequences are known, as are many functional fragments, mutants and modified versions. Examples of human factor VIII sequences, e.g., BDD, chimeric, and single chain sequences, are shown as subsequences in Table 2 (SEQ ID NOs:2, 6, or 8). Factor VIII polypeptides include, e.g., full-length factor VIII, full-length factor VIII minus Met at the N-terminus, mature factor VIII (minus the signal sequence), mature factor VIII with an additional Met at the N-terminus, and/or factor VIII with a full or partial deletion of the B domain. Factor VIII variants include B domain deletions, whether partial or full deletions.

As used herein, the term "processing site" or "intracellular processing site" refers to a type of enzymatic cleavage site in a polypeptide which is the target for enzymes that function after translation of the polypeptide. In one embodiment, such enzymes function during transport from the Golgi lumen to the trans-Golgi compartment. Intracellular processing enzymes cleave polypeptides prior to secretion of the protein from the cell. Examples of such processing sites include, e.g., those targeted by the PACE/furin (where PACE is an acronym for Paired basic Amino acid Cleaving Enzyme) family of endopeptidases. These enzymes are localized to the Golgi membrane and cleave proteins on the carboxyterminal side of the sequence motif Arg-[any residue]-(Lys or Arg)-Arg. As used herein the "furin" family of enzymes includes, e.g., PCSK1 (also known as PC1/Pc3), PCSK2 (also known as PC2), PCSK3 (also known as furin or PACE), PCSK4 (also known as PC4), PCSK5 (also known as PC5 or PC6), PCSK6 (also known as PACE4), or PCSK7 (also known as PC7/LPC, PC8, or SPC7). Other processing sites are known in the art. In constructs that include more than one processing or cleavage site, it will be understood that such sites can be the same or different.

"Processed Factor VIII," as used herein means Factor VIII that has been cleaved at an intracellular processing site, e.g., Arginine 1648 (for full-length Factor VIII) or Arginine 754 (for SQ B-domain deleted Factor VIII). Due to the cleavage at the intracellular processing site, processed Factor VIII comprises two polypeptide chains, the first chain being a heavy chain and the second chain being a light chain. A schematic representation of Factor VIII proteolytic processing is shown in FIG. 1. For example, the processed Factor VIII-Fc fusion protein (i.e., Heavy chain and Light chain fused to Fc) run at approximately 90 kDa and 130 kDa on a non-reducing SDS-PAGE, respectively, and 90 kDa and 105 kDa on a reducing SDS-PAGE, respectively.

"Single chain Factor VIII," "SC Factor VIII," or "SCFVIII" as used herein means Factor VIII that has not been cleaved at an intracellular processing site, e.g., at the Arginine site (residue 1648 for full-length Factor VIII (i.e., residue 1667 of SEQ ID NO: 6) or residue 754 for B-domain deleted Factor VIII (i.e., residue 773 of SEQ ID NO: 2). A schematic representation of processed rFVIIIFc compared to single chain rFVIIIFc is shown in FIG. 3.

"Chimeric polypeptide," as used herein, means a polypeptide that includes within it at least two polypeptides (or subsequences or peptides) from different sources. Chimeric polypeptides can include, e.g., two, three, four, five, six, seven, or more polypeptides from different sources, such as different genes, different cDNAs, or different animal or other species. Chimeric polypeptides can include, e.g., one or more linkers joining the different subsequences. Thus, the subsequences can be joined directly or they can be joined indirectly, via linkers, or both, within a single chimeric polypeptide. Chimeric polypeptides can include, e.g., additional peptides such as signal sequences and sequences such as 6His and FLAG that aid in protein purification or detection. In addition, Chimeric polypeptides can have amino acid or peptide additions to the N- and/or C-termini.

"Long-acting Factor VIII" is a Factor VIII having an increased half-life (also referred to herein as t½, t½ beta, elimination half-life and HL) over a reference Factor VIII. In some embodiments, the long-action Factor VIII is a chimeric single chain Factor VIII polypeptide. The increased half-life of a long-acting Factor VIII can be due to fusion to one or more non-Factor VIII moieties such as, e.g., an immunoglobulin constant region or a portion thereof (e.g., Fc), albumin, albumin binding polypeptide, PAS, the C-terminal peptide (CTP) of the β subunit of human chorionic gonadotropin, polyethylene glycol (PEG), hydroxyethyl starch (HES), albumin-binding small molecules, a vWF fragment, XTEN, or any combination thereof. The increased half-life can be due to one or more modification, such as, e.g., pegylation. Exemplary long-acting Factor VIII polypeptides include, e.g., chimeric single chain Factor VIII polypeptides comprising Fc, chimeric single chain Factor VIII polypeptides comprising XTEN, and chimeric single Factor VIII polypeptides comprising albumin. Additional exemplary long-acting Factor VIII polypeptides include, e.g., pegylated single chain Factor VIII.

The "reference" polypeptide, in the case of a long-acting chimeric Factor VIII polypeptide, is a polypeptide consisting essentially of the Factor VIII portion of the chimeric polypeptide, e.g., the same Factor VIII portion without the immunoglobulin constant region or a portion thereof (e.g., an Fc) portion, without the XTEN portion, without the albumin portion, without the albumin binding polypeptide portion, without the PAS portion, without the C-terminal peptide (CTP) of the β subunit of human chorionic gonadotropin portion, without the polyethylene glycol (PEG) portion, without the hydroxyethyl starch (HES) portion, without the albumin-binding small molecules portion, without the XTEN portion, or any combination thereof. Likewise, the reference polypeptide in the case of a modified Factor VIII is the same Factor VIII without the modification, e.g., a Factor VIII without the pegylation.

A "B domain" of Factor VIII, as used herein, is the same as the B domain known in the art that is defined by internal amino acid sequence identity and sites of proteolytic cleavage by thrombin, e.g., residues Ser741-Arg1648 of full length human factor VIII. The other human factor VIII domains are defined by the following amino acid residues: A1, residues Ala1-Arg372; A2, residues Ser373-Arg740; A3, residues Ser1690-Ile2032; C1, residues Arg2033-Asn2172; C2, residues Ser2173-Tyr2332. The A3-C1-C2 sequence includes residues Ser1690-Tyr2332. The remaining sequence, residues Glu1649-Arg1689, is usually referred to as the factor VIII light chain activation peptide. The locations of the boundaries for all of the domains, including the B domains, for porcine, mouse and canine factor VIII are also known in the art. A schematic representation of BBD rFVIIIFc is shown in FIG. 2.

"Subject," as used herein means a human individual. Subject can be a patient who is currently suffering from a bleeding disorder or is expected to be in need of such a treatment.

"Administering," as used herein, means to give a pharmaceutically acceptable Factor VIII polypeptide of the invention, e.g., a single chain Factor VIII polypeptide, to a subject via a pharmaceutically acceptable route. Routes of administration can be intravenous, e.g., intravenous injection and intravenous infusion. Additional routes of administration include, e.g., subcutaneous, intramuscular, oral, nasal, and pulmonary administration. Chimeric polypeptides and hybrid proteins can be administered as part of a pharmaceutical composition comprising at least one excipient.

"Prophylactic treatment," as used herein, means administering a Factor VIII polypeptide, e.g., a single chain Factor VIII polypeptide, in multiple doses to a subject over a course of time to increase the level of Factor FVIII activity in a subject's plasma. The increased level can be sufficient to decrease the incidence of spontaneous bleeding or to prevent bleeding, e.g., in the event of an unforeseen injury. During prophylactic treatment, the plasma protein level in the subject cannot fall below the baseline level for that subject, or below the level of Factor VIII that characterizes severe hemophilia (<1 IU/dl [1%]).

"Therapeutic dose," as used herein, means a dose that achieves a therapeutic goal, as described herein. The calculation of the required dosage of Factor VIII of the invention, e.g., single chain Factor VIII, is based upon the empirical finding that, on average, 1 IU of factor VIII per kg body weight raises the plasma factor VIII activity by approximately 2 IU/dL. The required dosage is determined using the following formula:

Required units=body weight (kg)×desired factor VIII rise (IU/dL or % of normal)×0.5 (IU/kg per IU/dL).

Cell Lines

Certain aspects of the invention are directed to an isolated cell line for producing a single chain Factor VIII polypeptide. In one embodiment, the single chain Factor VIII polypeptide, e.g., a chimeric single chain polypeptide, is produced by a recombinant cell line comprising a construct for expression of the single chain polypeptide. In another embodiment, the cell line is a mammalian cell line.

In particular, common mammalian cells used for production of recombinant proteins, such as Human embryonic kidney (HEK) cell lines (e.g., HEK293), Chinese hamster ovary (CHO) cell lines, Baby hamster kidney (BHK) cell line, COS cell lines, Madin Darby canine kidney (MDCK) cell line, or HeLa cell line are of interest. Expression vectors for such cells ordinarily include (if necessary) (an) origin(s) of replication, a promoter located in front of the gene to be expressed, along with any necessary ribosome binding sites, RNA splice sites, polyadenylation site, and transcriptional terminator sequences.

In one aspect, the cell line of the invention comprises a recombinant vector encoding a single chain Factor VIII disclosed herein. In one embodiment, the single chain Factor VIII of the invention contains no intracellular processing sites due to mutation/substitution or deletion. In another embodiment, the single chain Factor VIII of the invention comprises a substitution or mutation at an amino acid position corresponding to Arginine 1645, a substitution or mutation at an amino acid position corresponding to Arginine 1648, or a substitution or mutation at amino acid positions corresponding to Arginine 1645 and Arginine 1648 in full-length Factor VIII. In other embodiments, the amino acid substituted at the amino acid position corresponding to Arginine 1645 is a different amino acid from the amino acid substituted at the amino acid position corresponding to Arginine 1648. In other embodiments, the single chain Factor VIII of the invention further comprises a substitution or mutation at an amino acid corresponding to Glutamic Acid 720, comprises a substitution or mutation at an amino acid corresponding to Aspartic Acid 721, comprises a substitution or mutation at an amino acid corresponding to Tyrosine 729, comprises a substitution or mutation at an amino acid corresponding to Leucine 730, comprises a substitution or mutation at an amino acid corresponding to Serine 1657, comprises a substitution or mutation at an amino acid corresponding to Aspartic Acid 1658, or any combination thereof. In certain embodiments, the substitution or mutation is an amino acid other than its native amino acid residue. For example, the substitution or mutation at Arginine 1645 and/or 1648 can be an amino acid other than arginine, e.g., isoleucine, leucine, lysine, methionine, phenylalanine, threonine, tryptophan, valine, alanine, asparagine, aspartic acid, cysteine, glutamic acid, glutamine, glycine, proline, selenocysteine, serine, tyrosine, histidine, ornithine, pyrrolysine, or taurine. In another example, the substitution or mutation at Glutamic Acid 720 can be an amino acid other than glutamic acid, e.g., arginine, isoleucine, leucine, lysine, methionine, phenylalanine, threonine, tryptophan, valine, alanine, asparagine, aspartic acid, cysteine, glutamine, glycine, proline, selenocysteine, serine, tyrosine, histidine, ornithine, pyrrolysine, or taurine. In other examples, the substitution or mutation at Tyrosine 729 can be an amino acid other than tyrosine, e.g., arginine, isoleucine, leucine, lysine, methionine, phenylalanine, threonine, tryptophan, valine, alanine, asparagine, aspartic acid, cysteine, glutamic acid, glutamine, glycine, proline, selenocysteine, serine, histidine, ornithine, pyrrolysine, or taurine. In yet other examples, the substitution or mutation at Aspartic Acid 1658 can be an amino acid other than Aspartic Acid, e.g., arginine, isoleucine, leucine, lysine, methionine, phenylalanine, threonine, tryptophan, valine, alanine, asparagine, cysteine, glutamic acid, glutamine, glycine, proline, selenocysteine, serine, tyrosine, histidine, ornithine, pyrrolysine, or taurine. In one embodiment, the single chain Factor VIII comprises amino acid substitutions corresponding to R1645A and/or R1648A of full-length Factor VIII. In another embodiment, the single chain FVIII further comprises one or more substitutions or mutations, e.g., E720, D721, Y729, L730, S1657, and/or D1658. The substitution or mutation at R1645, R1648, E720, D721, Y729, L730, S1657, D1658, or any combination thereof can be effective at preventing or reducing cleavage at the corresponding internal processing domain. In another embodiment, the single chain FVIII comprises a deletion that eliminates one or more of the internal processing sites, e.g., 81645, R1648, E720, D721, Y729, L730, 51657, D1658, or any combination thereof.

Cells producing single chain Factor VIII polypeptides having FVIII activity are provided herein. In certain embodiments, the stability of the single chain Factor VIII polypeptide having FVIII activity is increased compared to a processed FVIII polypeptide. A single chain Factor VIII polypeptide having FVIII activity produced by the cells of the invention include deletion mutant proteins of FVIII in which a substantial part of the central region or "B domain" is deleted. In certain embodiments, plasmid constructs comprised of DNA sequences encoding single chain Factor VIII poly peptides having FVIII activity are used to transform a host cell. The transformed host cell is then grown to express the single chain FVIII gene. The host cell can be either an eukaryotic or a prokaryotic cell. Stable cell lines for producing single chain FVIII polypeptide can be expanded and used for production of a single chain FVIII polypeptide.

In other embodiments, a cell line of the invention further comprises a nucleotide sequence comprising an antisense nucleotide. In one embodiment, the antisense nucleotide is specific for a FVIII polypeptide processing enzyme. Antisense technology can be used to control gene expression through antisense DNA or RNA, or through triple-helix formation. Antisense techniques are discussed, for example, in Okano, J. Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1300 (1991). The methods are based on binding of a polynucleotide to a complementary DNA or RNA. In certain embodiments, the antisense nucleotide is specific for a FVIII polypeptide processing enzyme selected from a furin family enzyme, e.g., PCSK1 (also known as PC1/Pc3), PCSK2 (also known as PC2), PCSK3 (also known as furin or PACE), PCSK4 (also known as PC4), PCSK5 (also known as PC5 or PC6), PCSK6 (also known as PACE4), or PCSK7 (also known as PC7/LPC, PC8, or SPC7).

In some embodiments, the cell line of the present invention produces a combination of processed Factor VIII and single chain Factor VIII, wherein at least about 90% of the Factor VIII is single chain Factor VIII and about 10% of the Factor VIII is processed Factor VIII; wherein at least about 95% of the Factor VIII is single chain Factor VIII and about 5% of the Factor VIII is processed Factor VIII; wherein about 99% of the Factor VIII is single chain Factor VIII and about 1% of the Factor VIII is processed Factor VIII; or wherein about 100% of the Factor VIII is single chain Factor VIII.

In some embodiments, the single chain FVIII polypeptide is secreted from the cells and harvested from cell culture media. In another embodiment, the single chain FVIII polypeptide is isolated from cell lysates.

In some embodiments, the isolated cell line for producing a single chain FVIII polypeptide of the invention is referred to as "1E11."

Single Chain FVIII Polypeptide

Certain aspects of the invention are directed to a single chain FVIII polypeptide. In one embodiment, the single chain FVIII polypeptide is produced by a recombinant cell line of the application.

Single chain FVIII molecules have been disclosed, e.g., in Donath et al., Biochem J. 312(Pt 1):49-55 (1995); Pipe and Kaufman, PNAS 94(22):11851-6 (1997); and Scallan et al., Blood 102(10):3919-26 (2003), each of which are hereby incorporated by reference in its entirety.

In certain embodiments, the A1 and the A3 domains of the single chain FVIII polypeptide are connected by a metal ion mediated interaction, e.g., wherein metal ions stabilize A1 and A3 structures that mediate the interchain interactions, e.g., via a metal-ion mediated noncovalent bond. The metal ion mediated interaction between the A1 and the A3 domains can be any metal known in the art. For example, the metals useful for the invention can be a divalent metal ion. The metals that can be used to associate the A1 and the A3 domains include, but are not limited to, $Ca^{2+}$, $Mn^{2+}$, or $Cu^{2+}$. Fatouros et al. *Intern. J. Pharm.* 155(1): 121-131 (1997); Wakabayashi et al., *JBC.* 279(13): 12677-12684 (2004).

In some embodiments, the B domain of the single chain Factor VIII is deleted ("B domain deleted factor VIII" or "BDD FVIII"). An example of a BDD FVIII is REFACTO® (recombinant BDD FVIII), which has the same sequence as the Factor VIII portion of the sequence in Table 2A(i) (amino acids 20 to 1457 of SEQ ID NO:2). In one embodiment, the BDD FVIII is a BDD single chain FVIII polypeptide. In another embodiment, the B domain deleted Factor VIII contains an intact intracellular processing site, e.g. Arginine at residue 754 of B domain deleted Factor VIII, which corresponds to Arginine residue 773 of SEQ ID NO; 2, or residue 1648 of full-length Factor VIII, which corresponds to Arginine residue 1667 of SEQ ID NO: 6, but FVIII containing an intact intracellular processing site is not processed by a processing enzyme. The sequence residue numbers used herein without referring to any SEQ ID Numbers correspond to the Factor VIII sequence without the signal peptide sequence (19 amino acids) unless otherwise indicated. For example, S743/Q1638 of full-length Factor VIII corresponds to S762/Q1657 of SEQ ID NO: 6 due to the 19 amino acid signal peptide sequence. In other embodiments, the B domain deleted FVIII comprises a substitution or mutation at an amino acid position corresponding to Arginine 1645, a substitution or mutation at an amino acid position corresponding to Arginine 1648, or a substitution or mutation at amino acid positions corresponding to Arginine 1645 and Arginine 1648 in full-length Factor VIII. In some embodiments, the amino acid substituted at the amino acid position corresponding to Arginine 1645 is a different amino acid from the amino acid substituted at the amino acid position corresponding to Arginine 1648. In certain embodiments, the substitution or mutation is an amino acid other than its native amino Kid residue. For example, the substitution or mutation at Arginine 1645 and/or 1648 can be an amino acid other than arginine, e.g., isoleucine, leucine, lysine, methionine, phenylalanine, threonine, tryptophan, valine, alanine, asparagine, aspartic acid, cysteine, glutamic acid, glutamine, glycine, proline, selenocysteine, serine, tyrosine, histidine, ornithine, pyrrolysine, or taurine. In another example, the substitution or mutation at Glutamic Acid 720 can be an amino acid other than glutamic acid, e.g., arginine, isoleucine, leucine, lysine, methionine, phenylalanine, threonine, tryptophan, valine, alanine, asparagine, aspartic acid, cysteine, glutamine, glycine, proline, selenocysteine, serine, tyrosine, histidine, ornithine, pyrrolysine, or taurine. In other examples, the substitution or mutation at Tyrosine 729 can be an amino acid other than tyrosine, e.g., arginine, isoleucine, leucine, lysine, methionine, phenylalanine, threonine, tryptophan, valine, alanine, asparagine, aspartic acid, cysteine, glutamic acid, glutamine, glycine, proline, selenocysteine, serine, histidine, ornithine, pyrrolysine, or taurine. In yet other examples, the substitution or mutation at Aspartic Acid 1658 can be an amino acid other than Aspartic Acid, e.g., arginine, isoleucine, leucine, lysine, methionine, phenylalanine, threonine, tryptophan, valine, alanine, asparagine, cysteine, glutamic acid, glutamine, glycine, proline, selenocysteine, serine, tyrosine, histidine, ornithine, pyrrolysine, or taurine. In certain examples, the substitution or mutation at Arginine 1645 and 1648 is alanine. In certain embodiments, the BDD FVIII is a chimeric BDD single chain FVIII polypeptide comprising amino acid substitutions corresponding to R1645A, R1648A or both. In another embodiment, one or more further processing sites comprise a substitution or mutation, e.g., E720, Y729, and/or D1658. The substitution or mutation at R1645, R1648, E720, Y729, D1658, or any combination thereof can be effective at preventing or reducing cleavage at the corresponding internal processing domain.

A "B domain deleted factor VIII" or "BDD FVIII" can have the full or partial deletions disclosed in U.S. Pat. Nos. 6,316,226, 6,346,513, 7,041,635, 5,789,203, 6,060,447, 5,595,886, 6,228,620, 5,972,885, 6,048,720, 5,543,502, 5,610,278, 5,171,844, 5,112,950, 4,868,112, and 6,458,563, each of which is incorporated herein by reference in its entirety. In some embodiments, a BDD FVIII sequence of the present invention comprises any one of the deletions disclosed at col. 4, line 4 to col. 5, line 28 and examples 1-5 of U.S. Pat. No. 6,316,226 (also in U.S. Pat. No. 6,346,513). In some embodiments, a BDD FVIII of the present invention has a deletion disclosed at col. 2, lines 26-51 and examples 5-8 of U.S. Pat. No. 5,789,203 (also U.S. Pat. No. 6,060,447, U.S. Pat. No. 5,595,886, and U.S. Pat. No. 6,228,620). In some embodiments, a BDD FVIII has a deletion described in col. 1, lines 25 to col. 2, line 40 of U.S. Pat. No. 5,972,885; col. 6, lines 1-22 and example 1 of U.S. Pat. No. 6,048,720; col. 2, lines 17-46 of U.S. Pat. No. 5,543,502; col. 4, line 22 to col. 5, line 36 of U.S. Pat. No. 5,171,844; col. 2, lines 55-68, FIG. 2, and example 1 of U.S. Pat. No. 5,112,950; col. 2, line 2 to col. 19, line 21 and table 2 of U.S. Pat. No. 4,868,112; col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563. In some embodiments, a BDD FVIII has a deletion of most of the B domain, but still contains amino-terminal sequences of the B domain that are essential for in vivo proteolytic processing of the primary translation product into two polypeptide chains (i.e., intracellular processing site), as disclosed in WO 91/09122, which is incorporated herein by reference in its entirety. In some embodiments, a BDD FVIII is constructed with a deletion of amino acids 747-1638, i.e., virtually a complete deletion of the B domain. Hoeben R. C., et al. *J. Biol. Chem.* 265 (13): 7318-7323 (1990), incorporated herein by reference in its entirety. A BDD FVIII can also contain a deletion of amino acids 771-1666 or amino acids 868-1562 of factor VIII. Meulien P., et al. *Protein Eng.* 2(4):301-6 (1988), incorporated herein by reference in its entirety. Additional B domain deletions that are part of the invention include, e.g., deletion of amino acids 982 through 1562 or 760 through 1639 (Toole et al., *Proc. Natl. Acad. Sci. U.S.A.* 83:5939-5942 (1986)), 797 through 1562 (Eaton et al., *Biochemistry* 25:8343-8347 (1986)), 741 through 1646 (Kaufman (PCT published application No. WO 87/04187)), 747-1560 (Sarver et al., DNA 6:553-564 (1987)), 741 through 1648 (Pasek (PCT application No. 88/00831)), 816 through 1598 or 741 through 1689 (Lagner (Behring Inst. Mitt. (1988) No 82:16-25, EP 295597)), each of which is incorporated herein by reference in its entirety. In other embodiments, BDD FVIII includes a FVIII polypeptide containing fragments of the B-domain, that retain one or more N-linked glycosylation sites, e.g., residues 757, 784, 828, 900, 963, or optionally 943, which correspond to the amino acid sequence of the full-length FVIII sequence. Examples of the B-domain fragments include 226 amino acids or 163 amino acids of the B-domain as disclosed in Miao, H. Z., et al., *Blood* 103(a): 3412-3419 (2004), Kasuda, A., et al., *J. Thromb. Haemost.* 6: 1352-1359 (2008), and Pipe, S. W., et al., *J. Thromb. Haemost.* 9: 2235-2242 (2011) (i.e., the first 226 amino acids or 163 amino acids of the B domain are retained). In still other embodiments, BDD FVIII further comprises a point mutation at residue 309 (from Phe to Ser) to improve expression of the BDD FVIII protein. See Miao, H. Z., et al., Blood 103(a): 3412-3419 (2004). In still other embodiments, the BDD FVIII includes a FVIII polypeptide containing a portion of the B-domain, but not containing one or more furin cleavage sites (e.g., Arg1313 and Arg 1648). See Pipe, S. W., et al., *J. Thromb. Haemost.* 9: 2235-2242 (2011). Each of the foregoing deletions can be made in any Factor VIII sequence, e.g., a single chain Factor VIII sequence.

In one embodiment, the BDD FVIII is a single chain FVIII polypeptide comprising a metal ion mediated interaction connecting (or associating) a A1-A2-[partial or fully deleted B region] and a A3-C1-C2 region of the single chain Factor VIII polypeptide. In another embodiment, the B domain deleted single chain Factor VIII is the Factor VIII portion in a chimeric polypeptide. The single chain Factor VIII can comprise a substitution or mutation at one or more intracellular processing sites described herein.

Variant polypeptides can comprise, or alternatively consist of, an amino acid sequence which is at least 70%, 80%, 85%, 90%, 95%, 96%, 97%, 98%, 99% identical to, for example, the polypeptide sequence shown in SEQ ID NOS: 2, 4, 6, or 8 (the FVIII portion, the Fc portion, individually or together), and/or polypeptide fragments of any of these polypeptides (e.g., those fragments described herein).

A single chain Factor VIII (or Factor VIII portion of a chimeric polypeptide) can be at least about 70%, 80%, 85%, 90%, 95%, 96%, 97%, 98%, or 99% identical to a single chain Factor VIII amino acid sequence shown in Table 2 with or without a signal sequence (SEQ ID NO:8), wherein said Factor VIII portion has Factor VIII activity. A single chain FVIII can be 100% identical to the native FVIII sequence (either full-length mature FVIII or BDD FVIII) except one or more substitutions or mutations at the intracellular processing sites. A single chain Factor VIII (or Factor VIII portion of a chimeric polypeptide) can be identical to a single chain Factor VIII amino acid sequence shown in Table 2 with or without a signal sequence (SEQ ID NO:8).

A single chain Factor VIII (or Factor VIII portion of a chimeric polypeptide) can be at least about 70%, 80%, 85%, 90%, 95%, 96%, 97%, 98%, 99%, or 100% identical to the single chain Factor VIII amino acid sequence shown in Table 2 with or without a signal sequence (SEQ ID NO:8), wherein said Factor VIII portion has Factor VIII activity. A single Factor VIII (or Factor VIII portion of a chimeric polypeptide) can be identical to the Factor VIII amino acid sequence shown in Table 2 with or without a signal sequence (SEQ ID NO:8).

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence can include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence can be inserted, deleted, (indels) or substituted with another amino acid. These alterations of the reference sequence can occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 70%, 80%, 85%, 90%, 95%, 96%, 97%, 98% or 99% identical to, for instance, the amino acid sequences of SEQ ID NO:2, 6 or 8 (the factor VIII portion, the portion, individually or together) or 4, or a known factor VIII or Fc polypeptide sequence, can be determined conventionally using known computer programs. In one embodiment, a method for determining the best overall match between a query sequence (reference or original sequence) and a subject sequence, also refereed to as a global sequence alignment, can be determined using the FASTDB computer program based on the algorithm of Brutlag et al., Comp. App. Biosci. 6:237-245(1990), incorporated herein by reference in its entirety. In a sequence alignment the query and subject sequences are either both nucleotide sequences or both amino acid sequences. The result of said global sequence alignment is in percent identity. In another embodiment, parameters used in a FASTDB amino acid alignment are: Matrix=PAM 0, k-tuple=2, Mismatch Penalty=1, Joining Penalty=20, Randomization Group Length=0, Cutoff Score=1. Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to be made for the purposes of the present invention.

As stated above, polypeptide variants include, e.g., modified polypeptides. Modifications include, e.g., acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, (GPI anchor for nation, hydroxylation, iodination, methylation, myristoylation, oxidation, pegylation (Mei et al., *Blood* 116:270-79 (2010), which is incorporated herein by reference in its entirety), proteolytic processing, phosphorylation, prenylation, racemization, selenoylation, sulfation, transfer-RNA mediated addition of amino acids to proteins such as arginylation, and ubiquitination. In some embodiments, single chain Factor VIII is modified, e.g., pegylated, at any convenient location. In some embodiments, single chain Factor VIII is pegylated at a surface exposed amino acid of Factor VIII, e.g., a surface exposed cysteine, which can be an engineered cysteine. Id. In some embodiments, modified single chain Factor VIII, e.g., pegylated Factor VIII, is a long-acting Factor VIII.

In some embodiments, the single chain FVIII polypeptide is a chimeric polypeptide comprising a single chain Factor VIII portion and a non-Factor VIII portion. Exemplary non-Factor VIII portions include, e.g., Fc, XTEN, a von Willebrand Factor fragment, or albumin. Exemplary chimeric polypeptides of the invention include, e.g., chimeric single chain Factor VIII-Fc polypeptides, chimeric single chain Factor VIII-XTEN polypeptides, and chimeric single chain Factor VIII-albumin polypeptides.

In some embodiments, the single chain FVIII is fused to a heterologous moiety, e.g., a heterologous polypeptide or fragment thereof, e.g., a half-life extending moiety.

In some embodiments, the heterologous moiety is a half-life extending moiety. In certain embodiments, the half-life extending moiety is an immunoglobulin constant region or a portion thereof, albumin, albumin binding polypeptide, PAS, the C-terminal peptide (CTP) of the β subunit of human chorionic gonadotropin, polyethylene glycol (PEG), hydroxyethyl starch (HES), albumin-binding small molecules, XTEN, or any combination thereof. In certain embodiments, the immunoglobulin constant region or portion thereof is Fc.

In some embodiments, a chimeric polypeptide comprising a Factor VIII portion has an increased half-life (t½) over a polypeptide consisting of the same Factor VIII portion without the non Factor VIII portion. A chimeric Factor VIII polypeptide with an increased t½ can be referred to herein as a long-acting Factor VIII. Long-acting chimeric Factor VIII polypeptides include, e.g., single chain Factor VIII fused to Fc, singe chain Factor VIII fused to XTEN, and single chain Factor VIII fused to albumin.

Exemplary chimeric single chain Factor VIII-Fc polypeptides include, e.g., SEQ ID NO:8 (Table 2), with or without their signal sequences.

The chimeric polypeptide can comprise a sequence at least about 70%, 80%, 85%, 90%, 95%, 96%, 97%, 98%, 99%, or 100% identical to the single chain Factor VIII and Fc amino acid sequence shown in Table 2 with or without the signal sequence (SEQ ID NO:8), wherein the sequence has Factor VIII activity. The Factor VIII activity can be measured by activated Partial Thromboplastin Time (aPPT) assay, chromogenic assay, or other known methods. The chimeric polypeptide can comprise a sequence identical to the single chain Factor VIII and Fc amino acid sequence shown in Table 2 with or without the signal sequence (SEQ ID NO:8).

As discussed above, exemplary chimeric polypeptides include single chain Factor VIII fused to one or more XTEN polypeptides. Schellenburger et al., *Nat. Biotech.* 27:1186-90 (2009), which is incorporated herein by reference in its entirety. The XTEN polypeptide of the chimeric polypeptide can be fused to either the N-terminal end of the SCFVIII or to the C-terminal end of the SCFVIII. XTEN polypeptides include, e.g., those disclosed in WO 2009/023270, WO 2010/091122, WO 2007/103515, US 2010/0189682, and US 2009/0092582, each of which is incorporated herein by reference in its entirety.

As discussed above, exemplary chimeric polypeptides also include single chain Factor VIII fused to one or more albumin polypeptides, albumin binding polypeptides, or albumin-binding small molecules. In one embodiment, the albumin is human albumin. Albumin, albumin binding polypeptides, or albumin-binding small molecules can be fused to either the N-terminal end or the C-terminal end of SCFVIII or inserted between two amino acids adjacent to each Other in SCFVIII. Examples of albumin, e.g., fragments thereof, that can be used in the present invention are known. e.g., U.S. Pat. No. 7,592,010; U.S. Pat. No. 6,686,179; and Schulte, *Thrombosis Res.* 124 Suppl. 2:S6-S8 (2009), each of which is incorporated herein by reference in its entirety.

The albumin binding polypeptides can comprise, without limitation, bacterial albumin-binding domains, albumin-binding peptides, or albumin-binding antibody fragments that can bind to albumin. Domain 3 from streptococcal protein G, as disclosed by Kraulis et al., *FEBS Lett.* 378: 190-194 (1996) and Linhult et al., *Protein Sci.* 11:206-213 (2002) is an example of a bacterial albumin-binding domain. Examples of albumin-binding peptides include a series of peptides having the core sequence DICLPRWGCLW (SEQ ID NO: 28). See, e.g., Dennis et al., *J. Biol. Chem.* 2002, 277: 35035-35043 (2002). Examples of albumin-binding antibody fragments are disclosed in Muller and Kontermann, *Curr. Opin. Mol. Ther.* 9:319-326 (2007); Rooverset et al., *Cancer Immunol. Immunother.* 56:303-317 (2007), and Holt et al., *Prot. Eng. Design. Sci.,* 21:283-288 (2008), which are incorporated herein by reference in their entireties.

In certain aspects, a chimeric FVIII polypeptide of the invention comprises at least one attachment site for a non-polypeptide small molecule, variant, or derivative that can bind to albumin thereof. An example of such albumin binding moieties is 2-(3-maleimidopropanamido)-6-(4-(4-iodophenyl)butanamido)hexanoate ("Albu" tag) as disclosed by Trusselet et al., *Bioconjugate Chem.* 20:2286-2292 (2009).

As discussed above, exemplary chimeric polypeptides also include SC Factor VIII fused to at least one C-terminal peptide (CTP) of the β subunit of human chorionic gonadotropin or fragment, variant, or derivative thereof. The CTP can be fused to Factor VIII either the N-terminal end of SCFVIII or to the C-terminal end of SCFVIII or inserted between two amino acids adjacent to each other in SCFVIII. One or more CTP peptides fused to or inserted into a chimeric FVIII protein is known to increase the in vivo half-life of that protein. See, e.g., U.S. Pat. No. 5,712,122, incorporated by reference herein in its entirety. Exemplary C peptides include DPRFQDSSSSKAPPPSLPSPSRLPGPSDTPIL (SEQ ID NO:9) or SSSSKAPPPSLPSPSRLPGPSDTPILPQ. (SEQ ID NO:10). See, e.g., U.S. Patent Application Publication No. US 2009/0087411 A1, incorporated by reference.

As discussed above, exemplary chimeric polypeptides also include Factor VIII fused to at least one PAS sequence or fragment, variant, or derivative thereof. The PAS sequence can be fused to either the N-terminal end of SCFVIII or to the C-terminal end of SCFVIII or inserted between two amino acids adjacent to each other in FVIII. A PAS peptide or PAS sequence, as used herein, means an amino acid sequence comprising mainly alanine and serine residues or comprising mainly alanine, serine, and proline residues, the amino acid sequence forming random coil conformation under physiological conditions. Accordingly, the PAS sequence is a building block, an amino acid polymer, or a sequence cassette comprising, consisting essentially of, or consisting of alanine, serine, and proline which can be used as a part of the heterologous moiety in the chimeric protein. An amino acid polymer also can form random coil conformation when residues other than alanine, serine, and proline are added as a minor constituent in the PAS sequence. By "minor constituent" is meant that amino acids other than alanine, serine, and proline can be added in the PAS sequence to a certain degree, e.g., up to about 12%, i.e., about 12 of 100 amino acids of the PAS sequence, up to about 10%, up to about 9%, up to about 8%, about 6%, about 5%, about 4%, about 3%, i.e. about 2%, or about 1%, of the amino acids. The amino acids different from alanine, serine and proline can be selected from the group consisting of Arg, Asn, Asp, Cys, Gin, Glu, Gly, His, Ile, Leu, Lys, Met, Phe, Thr, Trp, Tyr, and Val. Under physiological conditions, a PAS peptide forms a random coil conformation and thereby can mediate an increased in vivo and/or in vitro stability to a chimeric protein of the invention, and has procoagulant activity.

Non-limiting examples of the PAS peptides include ASPAAPAPASPAAPAPSAPA (SEQ ID NO: 11), AAPASPAPAAPSAPAPAAPS (SEQ ID NO: 12), APSSPSPSAPSSPSPASPSS (SEQ ID NO: 13), APSSPSPSAPSSPSPASPS (SEQ ID NO: 14), SSPSAPSPSSPASPSPSSPA (SEQ ID NO: 15), AASPAAPSAPPAAASPAAPSAPPA (SEQ ID NO: 16), ASAAAPAAASAAASAPSAAA (SEQ ID NO: 17) or any variants, derivatives, fragments, or combinations thereof. Additional examples of PAS sequences are known from, e.g., US Pat. Publ. No. 2010/0292130 A1 and PCT Appl. Publ. No. WO 2008/155134 A1. European issued patent EP2173890.

As discussed above, exemplary chimeric polypeptides also include Factor VIII fused to at least one transferrin peptide or fragment, variant, or derivative thereof. At least one transferrin peptide can be fused to either the N-terminal end of SCFVIII or to the C-terminal end of SCFVIII or inserted between two amino acids adjacent to each other in SCFVIII. Any transferrin can be fused to or inserted into a chimeric FVIII protein of the invention. As an example, wild-type human Tf (Tf) is a 679 amino acid protein, of approximately 75 KDa (not accounting for glycosylation), with two main domains, N (about 330 amino acids) and C (about 340 amino acids), which appear to originate from a gene duplication. See GenBank accession numbers NM001063, XM002793, M12530, XM039845, XM 039847 and S95936 (www.ncbi.nlm.nih.gov), all of which are herein incorporated by reference in their entirety.

Transferrin transports iron through transferrin receptor (TfR)-mediated endocytosis. After the iron is released into an endosomal compartment and Tf-TfR complex is recycled to cell surface, the Tf is released back extracellular space for next cycle of iron transporting. Tf possesses a long half-life that is in excess of 14-17 days (Li et al., *Trends Pharmacol. Sci.* 23:206-209 (2002)). Transferrin fusion proteins have been studied for half-life extension, targeted deliver for cancer therapies, oral delivery and sustained activation of proinsulin (Brandsma et al., *Biotechnol. Adv.,* 29: 230-238 (2011); Bai et al., *Proc. Natl. Acad. Sci. USA* 102:7292-7296 (2005); Kim et al., *J. Pharmacol. Exp. Ther.,* 334:682-692 (2010); Wang et al., *J. Controlled Release* 155:386-392 (2011)).

As discussed above, exemplary chimeric polypeptides also include SC Factor VIII fused to at least one polyethylene glycol (PEG) moieties.

PEGylated SCFVIII can refer to a conjugate formed between SCFVIII and at least one polyethylene glycol (PEG) molecule. PEG is commercially available in a large variety of molecular weights and average molecular weight ranges. Typical examples of PEG average molecular weight ranges include, but are not limited to, about 200, about 300, about 400, about 600, about 1000, about 1300-1600, about 1450, about 2000, about 3000, about 3000-3750, about 3350, about 3000-7000, about 3500-4500, about 5000-7000, about 7000-9000, about 8000, about 10000, about 8500-11500, about 16000-24000, about 35000, about 40000, about 60000, and about 80000 daltons. These average molecular weights are provided merely as examples and are not meant to be limiting in any way.

A recombinant SCFVIII protein of the invention can be PEGylated to include mono- or poly-(e.g., 2-4) PEG moieties. PEGylation can be carried out by any of the PEGylation reactions known in the art. Methods for preparing a PEGylated protein product will generally include (i) reacting a polypeptide with polyethylene glycol (such as a reactive ester or aldehyde derivative of PEG) under conditions whereby the peptide of the invention becomes attached to one or more PEG groups; and (ii) obtaining the reaction product(s). In general, the optimal reaction conditions for the reactions will be determined case by case based on known parameters and the desired result.

There are a number of PEG attachment methods available to those skilled in the art, for example Malik F et al., *Exp. Hematol.* 20:1028-35 (1992); Francis, *Focus on Growth Factors* 3(2):4-10 (1992); European Pat. Pub. Nos. EP0401384, EP0154316, and EP0401384; and International Pat. Appl. Pub. Nos. WO92/16221 and WO95/34326. As a non-limiting example, FVIII variants can contain cysteine substitutions in one or more insertion sites in FVIII, and the cysteines can be further conjugated to PEG polymer. See Mei et al., *Blood* 116:270-279 (2010) and U.S. Pat. No. 7,632,921, which are incorporated herein by reference in their entireties.

As discussed above, exemplary chimeric polypeptides also include SC Factor VIII fused to at least one hydroxyethyl starch (HES) polymer. HES is a derivative of naturally occurring amylopectin and is degraded by alpha-amylase in the body. HES exhibits advantageous biological properties and is used as a blood volume replacement agent and in hemodilution therapy in the clinics. See, e.g., Sommermeyer et al., *Krankenhauspharmazie* 8:271-278 (1987); and Weidler et al., *Arzneim.-Forschung/Drug Res.* 41: 494-498 (1991).

HES is mainly characterized by the molecular weight distribution and the degree of substitution. HES has a mean molecular weight (weight mean) of from 1 to 300 kD, from 2 to 200kD, from 3 to 100 kD, or from 4 to 70kD. Hydroxyethyl starch can further exhibit a molar degree of substitution of from 0.1 to 3, from 0.1 to 2, from 0.1 to 0.9, or from 0.1 to 0.8, and a ratio between C2:C6 substitution in the range of from 2 to 20 with respect to the hydroxyethyl groups. HES with a mean molecular weight of about 130 kD is VOLUVEN® from Fresenius. VOLUVEN® is an artificial colloid, employed, e.g., for volume replacement used in the therapeutic indication for therapy and prophylaxis of hypovolaemia. There are a number of HES attachment methods available to those skilled in the art, e.g., the same PEG attachment methods described above.

As discussed above, exemplary chimeric polypeptides include single chain Factor VIII fused to an immunoglobulin constant region or a portion thereof.

An immunoglobulin constant region is comprised of domains denoted CH (constant heavy) domains (CH1, CH2, etc.). Depending on the isotype, (i.e. IgG, IgM, IgA IgD, or IgE), the constant region can be comprised of three or four CH domains. Some isotypes (e.g., IgG) constant regions also contain a hinge region. See Janeway et al. 2001, Immunobiology, Garland Publishing, N.Y., N.Y.

An immunoglobulin constant region or a portion thereof for producing the chimeric protein of the present invention can be obtained from a number of different sources. In some embodiments, an immunoglobulin constant region or a portion thereof is derived from a human immunoglobulin. It is understood, however, that the immunoglobulin constant region or a portion thereof can be derived from an immunoglobulin of another mammalian species, including for example, a rodent (e.g. a mouse, rat, rabbit, guinea pig) or non-human primate (e.g. chimpanzee, macaque) species. Moreover, the immunoglobulin constant region or a portion thereof can be derived from any immunoglobulin class, including Igm, IgG, IgD, IgA and IgE, and any immunoglobulin isotype, including IgG1, IgG2, IgG3 and IgG4. In one embodiment, the human isotype IgG1 is used.

A variety of the immunoglobulin constant region gene sequences (e.g., human constant region gene sequences) are available in the form of publicly accessible deposits. Constant region domains sequence can be selected having a particular effector function (or lacking a particular effector function) or with a particular modification to reduce immunogenicity. Many sequences of antibodies and antibody-encoding genes have been published and suitable Ig constant region sequences (e.g., hinge, CH2, and/or CH3 sequences, or portions thereof) can be derived from these sequences using art recognized techniques. The genetic material obtained using any of the foregoing methods can then be altered or synthesized to obtain polypeptides of the present invention. It will further be appreciated that the scope of this invention encompasses alleles, variants and mutations of constant region DNA sequences.

The sequences of the immunoglobulin constant region or a portion thereof can be cloned, e.g., using the polymerase chain reaction and primers which are selected to amplify the domain of interest. To clone a sequence of the immunoglobulin constant region or a portion thereof from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, Calif. (1990); Ho et al. 1989. Gene 77:51; Horton et al. 1993. Methods Enzymol. 217:270). PCR can be initiated by consensus constant region primers or by more specific primers based on the published heavy and light chain DNA and amino acid sequences. As discussed above, PCR also can be used to isolate DNA clones encoding the antibody light and heavy chains. In this case the libraries can be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al. 1994. J. Immunol. Methods 173:33); antibody leader sequences (Larrick et al. 1989 Biochem. Biophys. Res. Commun. 160:1250). The cloning of antibody sequences is further described in Newman et al., U.S. Pat. No. 5,658,570, filed Jan. 25, 1995, which is incorporated by reference herein.

An immunoglobulin constant region used herein can include all domains and the hinge region or portions thereof. In one embodiment, the immunoglobulin constant region or a portion thereof comprises CH2 domain, CH3 domain, and a hinge region, i.e., an Fc region or an FcRn binding partner.

As used herein, the term "Fc region" or "Fc" is defined as the portion of a polypeptide which corresponds to the Fc region of native immunoglobulin, i.e., as formed by the dimeric association of the respective Fc domains of its two heavy chains. A native Fc region forms a homodimer with another Fc region. In contrast, the term "genetically-fused Fc region" or "single-chain Fc region" (sac region), as used herein, refers to a synthetic dimeric Fc region comprised of Fc domains genetically linked within a single polypeptide chain (i.e., encoded in a single contiguous genetic sequence).

In one embodiment, the "Fc region" refers to the portion of a single immunoglobulin heavy chain beginning in the hinge region just upstream of the papain cleavage site (i.e., residue 216 in IgG, taking the first residue of heavy chain constant region to be 114) and ending at the C-terminus of the antibody. Accordingly, a complete Fc domain comprises at least a hinge domain, a CH2 domain, and a CH3 domain.

The Fc region of an immunoglobulin constant region, depending on the immunoglobulin isotype can include the CH2, CH3, and CH4 domains, as well as the hinge region. Chimeric proteins comprising an Fc region of an immunoglobulin bestow several desirable properties on a chimeric protein including increased stability, increased serum half-life (see Capon et al., 1989, Nature 337:525) as well as binding to Fc receptors such as the neonatal Fc receptor (FcRn) (U.S. Pat. Nos. 6,086,875, 6,485,726, 6,030,613; WO 03/077834; US2003-0235536A1), which are incorporated herein by reference in their entireties.

An immunoglobulin constant region or a portion thereof can be an FcRn binding partner. FcRn is active in adult epithelial tissues and expressed in the lumen of the intestines, pulmonary airways, nasal surfaces, vaginal surfaces, colon and rectal surfaces (U.S. Pat. No. 6,485,726). An FcRn binding partner is a portion of an immunoglobulin that binds to FcRn.

The FcRn receptor has been isolated from several mammalian species including humans. The sequences of the human FcRn, monkey FcRn, rat FcRn, and mouse FcRn are known (Story et al. 1994, J. Exp. Med. 180:2377). The FcRn receptor binds IgG (but not other immunoglobulin classes such as IgA, IgM, IgD, and IgE) at relatively low pH, actively transports the IgG transcellularly in a luminal to serosal direction, and then releases the IgG at relatively higher pH found in the interstitial fluids. It is expressed in adult epithelial tissue (U.S. Pat. Nos. 6,485,726, 6,030,613, 6,086,875; WO 03/077834; US2003-0235536A1) including lung and intestinal epithelium (Israel et al. 1997, Immunology 92:69) renal proximal tubular epithelium (Kobayashi et al. 2002, Am. J. Physiol. Renal Physiol. 282:F358) as well as nasal epithelium, vaginal surfaces, and biliary tree surfaces.

FcRn binding partners useful in the present invention encompass molecules that can be specifically bound by the FcRn receptor including whole IgG, the Fc fragment of IgG, and other fragments that include the complete binding region of the FcRn receptor. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The FcRn binding partners include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, Sequences of Proteins of Immunological Interest, U.S. Department of Public Health, Bethesda, Md.

Fc regions or FcRn binding partners bound to FcRn can be effectively shuttled across epithelial barriers by FcRn, thus providing a non-invasive means to systemically administer a desired therapeutic molecule. Additionally, fusion proteins comprising an Fc region or an FcRn binding partner are endocytosed by cells expressing the FcRn. But instead of being marked for degradation, these fusion proteins are recycled out into circulation again, thus increasing the in vivo half-life of these proteins. In certain embodiments, the portions of immunoglobulin constant regions are an Fc region or an FcRn binding partner that typically associates, via disulfide bonds and other non-specific interactions, with another Fc region or another FcRn binding partner to form dimers and higher order multimers.

Two FcRn receptors can bind a single Fc molecule. Crystallographic data suggest that each FcRn molecule binds a single polypeptide of the Fc homodimer. In one embodiment, linking the FcRn binding partner, e.g., an Fc fragment of an IgG, to a SCFVIII polypeptide provides a means of delivering the SCFVIII polypeptide orally, buccally, sublingually, rectally, vaginally, as an aerosol administered nasally or via a pulmonary route, or via an ocular route. In another embodiment, the chimeric protein can be administered invasively, e.g., subcutaneously, intravenously.

An FcRn binding partner region is a molecule or a portion thereof that can be specifically bound by the FcRn receptor with consequent active transport by the FcRn receptor of the Fc region. "Specifically bound" refers to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant $K_A$ is higher than $10^6$ M−1, or higher than $10^8$ M−1. If necessary, non-specific binding can be reduced without substantially affecting specific binding by varying the binding conditions. The appropriate binding conditions such as concentration of the molecules, ionic strength of the solution, temperature, time allowed for binding, concentration of a blocking agent (e.g. serum albumin, milk casein), etc., can be optimized by a skilled artisan using routine techniques.

In certain embodiments, a chimeric protein of the invention comprises one or more truncated Fc regions that are nonetheless sufficient to confer Fc receptor (FcR) binding properties to the Fc region. For example, the portion of an Fc region that binds to FcRn (i.e., the FcRn binding portion) comprises from about amino acids 282-438 of IgG1, (EU numbering) with the primary contact sites being amino acids 248, 250-257, 272, 285, 288, 290-291, 308-311, and 314 of the CH2 domain and amino acid residues 385-387, 428, and 433-436 of the CH3 domain. Thus, an Fc region of the invention can comprise or consist of an FcRn binding portion. FcRn binding portions can be derived from heavy chains of any isotype, including IgG1, IgG2, IgG3 and IgG4. In one embodiment, an FcRn binding portion from an antibody of the human isotype IgG1 is used. In another embodiment, an FcRn binding portion from an antibody of the human isotype IgG4 is used.

In another embodiment, the "Fc region" includes an amino acid sequence of an Fc domain or derived from an Fc domain. In certain embodiments, an Fc region comprises at least one of: a hinge (e.g., upper, middle, and/or lower hinge region) domain (about amino acids 216-230 of an antibody Fc region according to EU numbering), a CH2 domain (about amino acids 231-340 of an antibody Fc region according to EU numbering), a CH3 domain (about amino acids 341-438 of an antibody Fc region according to EU numbering), a CH4 domain, or a variant, portion, or fragment thereof. In other embodiments, an Fc region comprises a complete Fc domain (i.e., a hinge domain, a CH2 domain, and a CH3 domain). In some embodiments, an Fc region comprises, consists essentially of, or consists of a hinge domain (or a portion thereof) fused to a CH3 domain (or a portion thereof), a hinge domain (or a portion thereof) fused to a CH2 domain (or a portion thereof), a CH2 domain (or a portion thereof) fused to a CH3 domain (or a portion thereof), a CH2 domain (or a portion thereof) fused to both a hinge domain (or a portion thereof) and a CH3 domain (or a portion thereof). In still other embodiments, an Fc region lacks at least a portion of a CH2 domain (e.g., all or part of a CH2 domain). In a particular embodiment, an Fc region comprises or consists of amino acids corresponding to EU numbers 221 to 447.

In certain embodiments, the Fc variant confers a change in at least one effector function imparted by an Fc region comprising said wild-type Fc domain (e.g., an improvement or reduction in the ability of the Fc region to bind to Fc receptors (e.g. FcγRI, FcγRII, or FcγRIII) or complement proteins (e.g. C1q), or to trigger antibody-dependent cytotoxicity (ADCC), phagocytosis, or complement-dependent cytotoxicity (CDCC)). In other embodiments, the Fc variant provides an engineered cysteine residue.

The Fc regions of the invention can employ art-recognized Fc variants which are known to impart a change (e.g., an enhancement or reduction) in effector function and/or FcR or FcRn binding. Specifically, a binding molecule of the invention can include, for example, a change (e.g., a substitution) at one or more of the amino acid positions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; US Patent Publication Nos. US2007/0231329, US2007/0231329, US2007/0237765, US2007/0237766, US2007/0237767, US2007/0243188, US20070248603, US20070286859, US20080057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; 7,404,956, and 7,317,091, each of which is incorporated by reference herein. In one embodiment, the specific change (e.g., the specific substitution of one or more amino acids disclosed in the art) can be made at one or more of the disclosed amino acid positions. In another embodiment, a different change at one or more of the disclosed amino acid positions (e.g., the different substitution of one or more amino acid position disclosed in the art) can be made.

The Fc region or FcRn binding partner of IgG can be modified according to well recognized procedures such as site directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example, the following single amino acid residues in human IgG1 Fc (Fc γ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, P331A, E333A, K334A, T335A, S337A, K338A, K340A, Q342A, R344A, E345A, Q347A, R355A, E356A, M358A, T359A, K360A, N361A, Q362A, Y373A, S375A, D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, Where for example P238A represents wild type proline substituted by alanine at position number 238. As an example, a specific embodiment incorporates the N297A mutation, removing a highly conserved N-glycosylation site. In addition to alanine other amino acids can be substituted for the wild type amino acids at the positions specified above. Mutations can be introduced singly into Fc giving rise to more than one hundred Fc regions distinct from the native Fc. Additionally, combinations of two, three, or more of these individual mutations can be introduced together, giving rise to hundreds more Fc regions. Moreover, one of the Fc region of a construct of the invention can be mutated and the other Fc region of the construct not mutated at all, or they both can be mutated but with different mutations.

Certain of the above mutations can confer new functionality upon the Fc region or FcRn binding partner. For example, one embodiment incorporates N297A, removing a highly conserved N-glycosylation site. The effect of this mutation is to reduce immunogenicity, thereby enhancing circulating half-life of the Fc region, and to render the Fc region incapable of binding to FcγRI, FcγRIIA, FcγRIIB, and FcγRIIIA, without compromising affinity for FcRn (Routledge et al. 1995, Transplantation 60:847; Friend et al. 1999, Transplantation 68:1632; Shields et al. 1995, J. Biol. Chem. 276:6591). As a further example of new functionality arising from mutations described above, affinity for FcRn can be increased beyond that of wild type in some instances. This increased affinity can reflect an increased "on" rate, a decreased "off" rate or both. Examples of mutations believed to impart an increased affinity for FcRn include, but not limited to, T256A, T307A, E380A, and N434A (Shields et al. 2001, J. Biol. Chem. 276:6591).

Additionally, at least three human Fc gamma receptors appear to recognize a binding site on IgG within the lower hinge region, generally amino acids 234-237. Therefore, another example of new functionality and potential decreased immunogenicity can arise from mutations of this region, as for example by replacing amino acids 233-236 of human IgG1 "ELLG" (SEQ ID NO:18) to the corresponding sequence from IgG2 "PVA" (with one amino acid deletion). It has been shown that FcγRI, FcγRII, and FcγRIII, which mediate various effector functions will not bind to IgG1 when such mutations have been introduced. Ward and Ghetie 1995, Therapeutic Immunology 2:77 and Armour et al. 1999, Eur. J. Immunol. 29:2613.

In one embodiment, the immunoglobulin constant region or a portion thereof, e.g., an Fc region, is a polypeptide including the sequence PKNSSMISNTP (SEQ ID NO: 19) and optionally further including a sequence selected from HQSLGTQ (SEQ ID NO: 20), HQNLSDGK (SEQ ID NO: 21), HQNISDGK (SEQ ID NO: 22), or VISSHLGQ (SEQ ID NO: 23) (U.S. Pat. No. 5,739,277).

In certain embodiments, the immunoglobulin constant region or a portion thereof is hemi-glycosylated. For example, the chimeric protein comprising two Fc regions or FcRn binding partners can contain a first, glycosylated, Fc region (e.g., a glycosylated CH2 region) or FcRn binding partner and a second, aglycosylated, Fc region (e.g., an aglycosylated CH2 region) or FcRn binding partner. In one embodiment, a linker can be interposed between the glycosylated and aglycosylated Fc regions. In another embodiment, the Fc region or FcRn binding partner is fully glycosylated, i.e., all of the Fc regions are glycosylated. In other embodiments, the Fc region can be aglycosylated, i.e., none of the Fc moieties are glycosylated.

In certain embodiments, a chimeric protein of the invention comprises an amino acid substitution to an immunoglobulin constant region or a portion thereof (e.g., Fc variants), which alters the antigen-independent effector functions of the Ig constant region, in particular the circulating half-life of the protein.

Such proteins exhibit either increased or decreased binding to FcRn when compared to proteins lacking these substitutions and, therefore, have an increased or decreased half-life in serum, respectively. Fc variants with improved affinity for FcRn are anticipated to have longer serum half-lives, and such molecules have useful applications in methods of treating mammals where long half-life of the administered polypeptide is desired, e.g., to treat a chronic disease or disorder (see, e.g, U.S. Pat. Nos. 7,348,004, 7,404,956, and 7,862,820). In contrast, Fc variants with decreased FcRn binding affinity are expected to have shorter half-lives, and such molecules are also useful, for example, for administration to a mammal where a shortened circulation time can be advantageous, e.g. for in vivo diagnostic imaging or in situations where the starting polypeptide has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity can be desired include those applications in which localization the brain, kidney, and/or liver is desired. In one exemplary embodiment, the chimeric protein of the invention exhibit reduced transport across the epithelium of kidney glomeruli from the vasculature. In another embodiment, the chimeric protein of the invention exhibit reduced transport across the blood brain barrier (BBB) from the brain, into the vascular space. In one embodiment, a protein with altered FcRn binding comprises at least one Fc region or FcRn binding partner (e.g., one or two Fc regions or FcRn binding partners) having one or more amino acid substitutions within the "FcRn binding loop" of an Ig constant region. The FcRn binding loop is comprised of amino acid residues 280-299 (according to EU numbering) of a wild-type, full-length, Fc region. In other embodiments, an Ig constant region or a portion thereof in a chimeric protein of the invention having altered FcRn binding affinity comprises at least one Fc region or FcRn binding partner having one or more amino acid substitutions within the 15 Å FcRn "contact zone." As used herein, the term 15 Å FcRn "contact zone" includes residues at the following positions of a wild-type, fall-length Fc moiety: 243-261, 275-280, 282-293, 302-319, 336-348, 367, 369, 372-389, 391, 393, 408, 424, and 425-440 (EU numbering). In other embodiments, a Ig constant region or a portion thereof of the invention having altered FcRn binding affinity comprises at least one Fc region or FcRn binding partner having one or more amino acid substitutions at an amino acid position corresponding to any one of the following EU positions: 256, 277-281, 283-288, 303-309, 313, 338, 342, 376, 381, 384, 385, 387, 434 (e.g., N434A or N434K), and 438. Exemplary amino acid substitutions which altered FcRn binding activity are disclosed in International PCT Publication No. WO05/047327 which is incorporated by reference herein.

An Fc region or FcRn binding partner used in the invention can also comprise an art recognized amino acid substitution which alters the glycosylation of the chimeric protein. For example, the Fc region or FcRn binding partner of the chimeric protein linked to a SCFVIII protein can comprise an Fc region having a mutation leading to reduced glycosylation (e.g., N or O-linked glycosylation) or can comprise an altered glycoform of the wild-type Fc moiety (e.g., a low fucose or fucose-free glycan).

In one embodiment, a single chain chimeric protein of the invention can comprise a genetically fused Fc region (i.e., scFc region) having two or more of its constituent Ig constant region or a portion thereof independently selected from the Ig constant region or a portion thereof described herein. In one embodiment, the Fc regions of a dimeric Fc region are the same. In another embodiment, at least two of the Fc regions are different. For example, the Fc regions or FcRn binding partners of the proteins of the invention comprise the same number of amino acid residues or they can differ in length by one or more amino acid residues (e.g, by about 5 amino acid residues 1, 2, 3, 4, or 5 amino acid residues), about 10 residues, about 15 residues, about 20 residues, about 30 residues, about 40 residues, or about 50 residues). In yet other embodiments, the Fc regions or FcRn binding partners of the protein of the invention can differ in sequence at one or more amino acid positions. For example, at least two of the Fc regions or Fan binding partners can differ at about 5 amino acid positions (e.g., 1, 2, 3, 4, or 5 amino acid positions), about 10 positions, about 15 positions, about 20 positions, about 30 positions, about 40 positions, or about 50 positions.

The Fc (or Fc portion of a chimeric polypeptide) can be at least about 70%, 80%, 85%, 90%, 95%, 96%, 97%, 98%, 99%, or 100% identical to the Fc amino acid sequence shown in Table 2 (amino acids 1458 to 1684 of SEQ ID NO:2, amino acids 2352 to 2578 of SEQ ID NO:6, or amino acids 1450 to 1684 of SEQ ID NO:8). The Fc (or Fc portion of a chimeric polypeptide) can be identical to the Fc amino acid sequence shown in Table 2 (amino acids 1458 to 1684 of SEQ ID NO:2, amino acids 2352 to 2578 of SEQ ID NO:6, or amino acids 1450 to 1684 of SEQ ID NO:8).

In certain embodiments, the single chain Factor VIII-Fc fusion protein can be identified by size, e.g., the single chain Factor VIII-Fc can run at approximately 220 kDa on a non reducing SDS-PAGE and at approximately 195 kDa on a reducing SDS-PAGE.

Therefore, single chain Factor VIII in the chimeric polypeptide used herein comprises a single chain. The Factor VIII portion, i.e., the single chain Factor VIII, in the chimeric polypeptide used herein has Factor VIII activity. Factor VIII activity can be measured by any known methods in the art. For example, one of those methods can be a chromogenic assay. The chromogenic assay mechanism is based on the principles of the blood coagulation cascade, where activated Factor VIII accelerates the conversion of Factor X into Factor Xa in the presence of activated Factor IX, phospholipids and calcium ions. The Factor Xa activity is assessed by hydrolysis of a p-nitroanilide (pNA) substrate specific to Factor Xa. The initial rate of release of p-nitroaniline measured at 405 nM is directly proportional to the Factor Xa activity and thus to the Factor VIII activity in the sample. The chromogenic assay is recommended by the Factor VIII and Factor IX Subcommittee of the Scientific and Standardization Committee (SSC) of the International Society on Thrombosis and Hemostatsis (ISTH). Since 1994, the chromogenic assay has also been the reference method of the European Pharmacopoeia for the assignment of FVIII concentrate potency. Thus, in one embodiment, the chimeric polypeptide comprising single chain Factor VIII has Factor VIII activity comparable to a chimeric polypeptide comprising processed Factor VIII (e.g., a chimeric polypeptide consisting essentially of or consisting of two Fc portions and processed Factor VIII, wherein said processed Factor VIII is fused to one of the two Fc portions), when the Factor VIII activity is measured in vitro by a chromogenic assay.

In another embodiment, the chimeric polypeptide comprising single chain Factor VIII of this invention has a Factor Xa generation rate comparable to a chimeric polypeptide comprising processed Factor VIII (e.g., a chimeric polypeptide consisting essentially of or consisting of two Fc portions and processed Factor VIII, wherein the processed Factor VIII is fused to one Fc of the two Fc portions).

In order to activate Factor X to Factor Xa, activated Factor IX (Factor IXa) hydrolyses one arginine-isoleucine bond in Factor X to form Factor Xa in the presence of $Ca^{2+}$, membrane phospholipids, and a Factor VIII cofactor. Therefore, the interaction of Factor VIII with Factor IX is critical in coagulation pathway. In certain embodiments, the chimeric polypeptide comprising single chain factor VIII can interact with Factor IXa at a rate comparable to a chimeric polypeptide comprising processed Factor VIII (e.g., a chimeric polypeptide consisting essentially of or consisting of two Fc portions and processed Factor VIII, wherein the processed Factor VIII is fused to one Fc of the two Fc portions).

In addition, Factor VIII is bound to von Willebrand Factor while inactive in circulation. Factor VIII degrades rapidly when not bound to vWF and is released from vWF by the action of thrombin. In some embodiments, the chimeric polypeptide comprising single chain Factor VIII binds to von Willebrand Factor at a level comparable to a chimeric polypeptide comprising processed Factor VIII (e.g., a chimeric polypeptide consisting essentially of or consisting of two Fc portions and processed Factor VIII, wherein the processed Factor VIII is fused to one Fc of the two Fc portions).

Factor VIII can be inactivated by activated protein C in the presence of calcium and phospholipids. Activated protein C cleaves Factor VIII heavy chain after Arginine 336 in the A1 domain, which disrupts a Factor X substrate interaction site, and cleaves after Arginine 562 in the A2 domain, which enhances the dissociation of the A2 domain as well as disrupts an interaction site with the Factor IXa. This cleavage also bisects the A2 domain (43 kDa) and generates A2-N (18 kDa) and A2-C (25 kDa) domains. Thus, activated protein C can catalyze multiple cleavage sites in the heavy chain. In one embodiment, the chimeric polypeptide comprising single chain Factor VIII is inactivated by activated Protein C at a level comparable to a chimeric polypeptide comprising processed Factor VIII (e.g., a chimeric polypeptide consisting essentially of or consisting of two Fc portions and processed Factor VIII, wherein the processed Factor VIII is fused to one Fc of the two Fc portions).

In other embodiments, the chimeric polypeptide comprising single chain Factor VIII has Factor VIII activity in vivo comparable to a chimeric polypeptide comprising processed Factor VIII (e.g., a chimeric polypeptide consisting essentially of or consisting of two Fc portions and processed Factor VIII, wherein the processed Factor VIII is fused to one Fc of the two Fc portions). In a particular embodiment, the chimeric polypeptide comprising single chain Factor VIII is capable of protecting a HemA mouse at a level comparable to a chimeric polypeptide comprising processed Factor VIII (e.g., a chimeric polypeptide consisting essentially of or consisting of two Fc portions and processed Factor VIII, wherein said processed Factor VII is fused to one Fc of the two Fc portions) in a HemA mouse tail vein transection model.

In some embodiments, the chimeric single chain Factor VIII having Factor VIII activity has increased expression, solubility, stability and/or circulating time, or decreased immunogenicity compared to a processed Factor VIII polypeptide. In certain embodiments, the chimeric single chain Factor VIII having Factor VIII activity is more stable compared to a processed Factor VIII polypeptide.

The term "comparable" or "compared" as used herein means a compared rate or level resulted from using the chimeric polypeptide is equal to, substantially equal to, or similar to the reference rate or level. The term "similar" as used herein means a compared rate or level has a difference of no more than 10% or no more than 15% from the reference rate or level (e.g., FXa generation rate by a chimeric polypeptide consisting essentially of or consisting of two Fc portions and processed Factor VIII, wherein the processed Factor VIII is fused to one Fc of the two Fc portions). The term “substantially equal” means a compared rate or level has a difference of no more than 0.01%, 0.5% or 1% from the reference rate or level.

In another embodiment, the singe chain FVIII is a hybrid polypeptide. “Hybrid” polypeptides and proteins, as used herein, means a combination of a chimeric polypeptide with a second polypeptide. The chimeric polypeptide and the second polypeptide in a hybrid can be associated with each other via protein-protein interactions, such as charge-charge or hydrophobic interactions. The chimeric polypeptide and the second polypeptide in a hybrid can be associated with each other via disulfide or other covalent bond(s). Hybrids are described in WO 2004/101740 and WO 2006/074199, each of which is incorporated herein by reference in its entirety. See also U.S. Pat. Nos. 7,404,956 and 7,348,004, each of which is incorporated herein by reference in its entirety. The second polypeptide can be a second copy of the same chimeric polypeptide or it can be a non-identical chimeric polypeptide. In one embodiment, the second polypeptide is a polypeptide comprising an Fc. In another embodiment, the chimeric polypeptide is a chimeric single chain Factor VIII-Fc polypeptide and the second polypeptide consists essentially of Fc.

The second polypeptide in a hybrid can comprise or consist essentially of a sequence at least about 70%, 80%, 85%, 90%, 95%, 96%, 97%, 98%, 99%, or 100% identical to the amino acid sequence shown in Table 2A(ii) without a signal sequence (amino acids 21 to 247 of SEQ ID NO:4) or at least 90% or 95% identical to the amino acid sequence shown in Table 2A(ii) with a signal sequence (amino acids 1 to 247 of SEQ ID NO-:4). The second polypeptide can comprise or consist essentially of a sequence identical to the amino acid sequence shown in Table 2A(ii) without a signal sequence (amino acids 21 to 247 of SEQ ID NO:4) or identical to the amino acid sequence shown in Table 2A(ii) with a signal sequence (amino acids 1 to 247 of SEQ ID NO:4).

Polynucleotides

Polynucleotides include, e.g., those in Table 1, which encode the polypeptides of Table 2 (see Table 1). Polynucleotides also include, e.g., fragments of the polynucleotides of Table 1, e.g., those that encode fragments of the polypeptides of Table 2, such as the Factor VIII, Fc, signal sequence, 6His and other fragments of the polypeptides of Table 2.

In another aspect, the invention provides an isolated nucleic acid molecule comprising a polynucleotide which hybridizes under stringent hybridization conditions to a portion of a polynucleotide in a nucleic acid molecule of the invention described herein, a polynucleotide encoding a single chain FVIII of the invention. Hybridizing polynucleotides are useful as probes and primers. Portions of a polynucleotide which hybridize to the single chain FVIII polypeptide encoding sequence, which can be precisely specified by 5' and 3' base positions or by size in nucleotide bases or precisely excluded in the same manner. Similarly, portions of a polynucleotide, which hybridize to the single chain FVIII polypeptide, which can be used as probes and primers as well. Preferred hybridizing polynucleotides of the present invention are those that, when labeled and used in a hybridization assay known in the art (e.g. Southern and Northern blot analysis), display the greatest signal strength regardless of other heterologous sequences present in equimolar amounts.

In certain embodiments, the polynucleotides of the invention, e.g., polynucleotides encoding single chain FVIII polypeptides, can include variants. Variants of the invention can include those produced by nucleotide substitutions, deletions, or additions. The substitutions, deletions, or additions can involve one or more nucleotides. Alterations in the amino acid sequence can produce conservative or non-conservative amino acid substitutions, deletions or additions. Among these included are silent substitutions, additions and deletions, which do not alter the properties and activities of the polypeptides of the present invention or portions thereof. Also included in this regard are conservative substitutions.

Variant polynucleotides can comprise, or alternatively consist of, a nucleotide sequence which is at least about 85%, 90%, 95%, 96%, 97%, 98% or 99% identical to, for example, the nucleotide coding sequence in SEQ ID NO:1, 3, 5, or 7 (the factor VIII portion, the Fc portion, individually or together) or the complementary strand thereto, the nucleotide coding sequence of known mutant and recombinant factor VIII or Fc such as those disclosed in the publications and patents cited herein or the complementary strand thereto, a nucleotide sequence encoding the polypeptide of SEQ ID NO:2, 4, 6, or 8 (the factor VIII portion, the Fc portion, individually or together), and/or polynucleotide fragments of any of these nucleic acid molecules (e.g., those fragments described herein). Polynucleotides which hybridize to these nucleic acid molecules under stringent hybridization conditions or lower stringency conditions are also included as variants, as are polypeptides encoded by these polynucleotides as long as they are functional.

A great many functional factor VIII variants are known, as is discussed above and below. In addition, hundreds of nonfunctional mutations in factor VIII have been identified in hemophilia patients, and it has been determined that the effect of these mutations on factor VIII function is due more to where they lie within the 3-dimensional structure of factor VIII than on the nature of the substitution (Cutler et al., *Hum. Mutat.* 19:274-8 (2002)), incorporated herein by reference in its entirety. In addition, comparisons between factor VIII from humans and other species have identified conserved residues that are likely to be required for function (Cameron et al., Thromb. Haemost. 79:317-22 (1998); U.S. Pat. No. 6,251,632), incorporated herein by reference in its entirety.

By a nucleic acid having a nucleotide sequence at least, for example, 95% “identical” to a reference nucleotide sequence, it is intended that the nucleotide sequence of the nucleic acid is identical to the reference sequence except that the nucleotide sequence can include up to five point mutations per each 100 nucleotides of the reference nucleotide sequence. In other words, to obtain a nucleic acid having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. The query sequence can be, for example, the entire sequence shown in SEQ ID NO:1 or 3, the ORF (open reading frame), or any fragment specified as described herein.

As a practical matter, whether any particular nucleic acid molecule or polypeptide is at least 85%, 90%, 95%, 96%, 97%, 98% or 99% identical to a nucleotide sequence or polypeptide of the present invention can be determined conventionally using known computer programs. In one embodiment, a method for determining the best overall match between a query sequence (reference or original sequence) and a subject sequence, also referred to as a global sequence alignment, can be determined using the FASTDB computer program based on the algorithm of Brutlag et al.,

*Comp. App. Biosci.* 6:237-245 (1990), which is herein incorporated by reference in its entirety In a sequence alignment the query and subject sequences are both DNA sequences. An RNA sequence can be compared by converting U's to T's. The result of said global sequence alignment is in percent identity. In another embodiment, parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to be made for the purposes of the present invention.

The polynucleotide variants can contain alterations in the coding regions, non-coding regions, or both. In one embodiment, the polynucleotide variants contain alterations which produce silent substitutions, additions, or deletions, but do not alter the properties or activities of the encoded polypeptide. In another embodiment, nucleotide variants are produced by silent substitutions due to the degeneracy of the genetic code. In other embodiments, variants in which 5-10, 1-5, or 1-2 amino acids are substituted, deleted, or added in any combination. Polynucleotide variants can be produced for a variety of reasons, e.g., to optimize codon expression for a particular host (change codons in the human mRNA to others, e.g., a bacterial host such as *E. coli*).

Naturally occurring variants are called "allelic variants," and refer to one of several alternate forms of a gene occupying a given locus on a chromosome of an organism (Genes II, Lewin, B., ed., John Wiley & Sons, New York (1985)). These allelic variants can vary at either the polynucleotide and/or polypeptide level and are included in the present invention. Alternatively, non-naturally occurring variants can be produced by mutagenesis techniques or by direct synthesis.

Using known methods of protein engineering and recombinant DNA technology, variants can be generated to improve or alter the characteristics of the polypeptides. For instance, one or more amino acids can be deleted from the N-terminus or C-terminus of the secreted protein without substantial loss of biological function. Ron et al., *J. Biol. Chem.* 268: 2984-2988 (1993), incorporated herein by reference in its entirety, reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein. (Dobeli et al., *J. Biotechnology* 7:199-216 (1988), incorporated herein by reference in its entirety.)

Moreover, ample evidence demonstrates that variants often retain a biological activity similar to that of the naturally occurring protein. For example, Gayle and coworkers (*J. Biol. Chem* 268:22105-22111 (1993), incorporated herein by reference in its entirety) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See Abstract.) In fact, only 23 unique amino acid sequences, out of more than 3,500 nucleotide sequences examined, produced a protein that significantly differed in activity from wild-type.

Vectors

The invention allows for the use of sequences in expression vectors, as well as to transfect host cells and cell lines of the invention, e.g., prokaryotic or eukaryotic cells. The invention also allows for purification of the polypeptides expressed from the expression vector. The expression vector can contain various Molecular tags for easy purification. In some embodiments, a subsequently obtained expression construct can be transformed into any host cell of choice. Cell lysates from the transformed host cell can be isolated by established methods well known in the field.

As used herein, "vector", "polynucleotide vector", "construct" and "polynucleotide construct" are used interchangeably herein. A polynucleotide vector of the invention can be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-associated virus (AAV)), DNA encapsulated in liposomes, DNA complexed with polylysine, complexed with synthetic polycationic molecules, complexed with compounds such as polyethylene glycol (PEG) to immunologically "mask" the molecule and/or increase half-life, or conjugated to a non-viral protein. In certain embodiments, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

For use in mammalian cells, the regulatory functions on the expression vectors can be provided by viral material. For example, commonly used promoters are derived from elongation factor-1 (EF-1), Simian Virus 40 (SV40) and Cytomegalovirus (CMV). Furthermore, it is also possible, and often desirable, to utilize promoter or regulatory sequences normally associated with the desired gene sequence, provided such regulatory sequences are compatible with the host cell systems.

Vectors can be engineered to encode selectable markers or reporters that provide for the selection or identification of cells that have incorporated the vector. Expression of selectable markers or reporters allows identification and/or selection of host cells that incorporate and express other coding regions contained on the vector. The term "selectable marker" refers to an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include, e.g., genes providing resistance to zeocin, ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like. Examples of reporters known and used in the art include, e.g., luciferase (Luc), green fluorescent protein (GFP), chloramphenicol acetyltransferase (CAT), -galactosidase (LacZ), -glucuronidase (Gus), and the like. Selectable markers can also be considered to be reporters.

The term "reporter gene" refers to a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like. Selectable marker genes can also be considered reporter genes.

"Promoter and "promoter sequence" are used interchangeably and refer to a DNA sequence capable of controlling the expression of a coding sequence or functional RNA. In general, a coding sequence is located 3' to a promoter sequence. Promoters can be derived in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, DNA fragments of different lengths can have identical promoter activity.

The promoter sequence is typically bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

The term "expression vector" refers to a vehicle designed to enable the expression of an inserted polynucleotide sequence following insertion into a host cell. The inserted polynucleotide sequence is placed in operable association with regulatory regions as described above.

Vectors can be introduced into host cells by methods well known in the art, e.g., transfection, electroporation, microinjection, transduction, cell fusion, DEAE dextran, calcium phosphate precipitation, lipofection (lysosome fusion), use of a gene gun, or a DNA vector transporter.

Compositions

In certain aspects of the invention are directed to a composition comprising a cell line, a single chain FVIII polypeptide, a polynucleotide, or a vector of the invention. In certain embodiments, the composition of the present invention comprises a combination of processed Factor VIII (e.g., a rFVIIIFc) and single chain Factor VIII (e.g., a SC rFVIIIFc), wherein at least about 80% of the Factor VIII is a single chain Factor VIII and about 20% of the Factor VIII is a processed Factor VIII; wherein at least about 85% of the Factor VIII is a single chain Factor VIII and about 15% of the Factor VIII is a processed Factor VIII; wherein at least about 90% of the Factor VIII is a single chain Factor VIII and about 10% of the Factor VIII is a processed Factor VIII; wherein at least about 95% of the Factor VIII is a single chain Factor VIII and about 5% of the Factor VIII is a processed Factor VIII; wherein at least about 96% of the Factor VIII is a single chain Factor VIII and about 4% of the Factor VIII is a processed Factor VIII; wherein at least about 97% of the Factor VIII is a single chain Factor VIII and about 3% of the Factor VIII is a processed Factor VIII; wherein at least about 98% of the Factor VIII is a single chain Factor VIII and about 2% of the Factor VIII is a processed Factor VIII; wherein about 99% of the Factor VIII is a single chain Factor VIII and about 1% of the Factor VIII is a processed Factor VIII; or wherein about 100% of the Factor VIII is single chain Factor VIII.

In certain embodiments, the composition comprising a single chain FVIII of the present invention has Factor VIII activity comparable, better than or similar to a composition comprising processed Factor VIII, e.g., when the Factor VIII activity is measured in vitro by a chromogenic assay.

In other embodiments, the composition comprising a single chain FVIII of the invention has a Factor Xa generation rate comparable to a composition comprising processed Factor VIII. In still other embodiments, the composition comprising single chain factor VIII can interact with Factor IXa at a rate comparable to a composition comprising processed Factor. In further embodiments, the single chain Factor VIII of the present composition is inactivated by activated Protein C at a level comparable to a processed Factor VIII composition. In a particular embodiment, the composition comprising a single chain Factor VIII of the invention has Factor VIII activity in vivo comparable to a composition comprising processed Factor VIII. In some embodiments, the composition comprising a single chain Factor VIII of the invention is capable of protecting HemA mouse at a level comparable to a composition comprising processed Factor VIII in HemA mouse tail vein transection model.

In certain embodiments, the composition of the invention further comprises a pharmaceutically acceptable carrier.

The pharmaceutical compositions comprising at least about 90%, 91%, 91%, 93%, 94%, 95%, 96%, 97%, 98%, or 99% of single chain Factor VIII can be formulated for any appropriate manner of administration, including, for example, topical (e.g., transdermal or ocular), oral, buccal, nasal, vaginal, rectal or parenteral administration.

The term parenteral as used herein includes subcutaneous, intradermal, intravascular (e.g., intravenous), intramuscular, spinal, intracranial, intrathecal, intraocular, periocular, intraorbital, intrasynovial and intraperitoneal injection, as well as any similar injection or infusion technique. The composition can also be for example a suspension, emulsion, sustained release formulation, cream, gel or powder. The composition can be formulated as a suppository, with traditional binders and carriers such as triglycerides.

In one example, the pharmaceutical formulation is a liquid formulation, e.g., a buffered, isotonic, aqueous solution. In another example, the pharmaceutical composition has a pH that is physiologic, or close to physiologic. In other examples, the aqueous formulation has a physiologic or close to physiologic osmolarity and salinity. It can contain sodium chloride and/or sodium acetate. In some examples, the composition of the present invention is lyophilized.

Methods of Producing Cell Lines

Certain aspects of the invention are directed to methods for producing a cell line that produces a single chain FVIII polypeptide comprising the steps of: (a) contacting a host cell with a polynucleotide comprising a nucleotide sequence encoding the single chain FVIII polypeptide of the invention; and (b) isolating a cell line producing the single chain F VIII polypeptide. In certain embodiments, the method further comprises (c) propagating the cell line to produce the single chain FVIII polypeptide. In some embodiments, the host cell further comprises a selectable marker gene, e.g., a gene providing resistance to zeocin, ampicillin, streptomycin, gentamycin, kanamycin, hygromycin, bialaphos herbicide, or sulfonamide. In certain embodiments, the selectable marker gene provides resistance to zeocin. In one embodiment, the cell line producing the single chain FVIII polypeptide is resistant to zeocin.

In certain embodiments, the host cell is a eukaryotic cell. In some embodiments, the eukaryotic cell is a mammalian cell. A mammalian cell is any cell derived from a mammal. Mammalian cells specifically include, but are not limited to, mammalian cell lines. In one embodiment, the mammalian cell is a human cell. In another embodiment, the mammalian cell is a HEK 293 cell, which is a human embryonic kidney cell line. HEK 293 cells are available as CRL-1533 from American Type Culture Collection, Manassas, Va., and as 293-H cells, Catalog No. 11631-017 or 293-F cells, Catalog No. 11625-019 from Invitrogen (Carlsbad, Calif.). In some embodiments, the mammalian cell is a PER.C6® cell, which is a human cell line derived from retina. PER.C6® cells are available from Crucell (Leiden, The Netherlands). In other embodiments, the mammalian cell is a Chinese hamster ovary (CHO) cell. CHO cells are available from American Type Culture Collection, Manassas, Va. (e.g., CHO-K1; CCL-61). In still other embodiments, the mammalian cell is a baby hamster kidney (BHK) cell. BHK cells are available from American Type Culture Collection, Manassas, Va. (e.g., CRL-1632). In some embodiments, the mammalian cell is a HKB 11 cell, which is a hybrid cell line of a HEK293 cell and a human B cell line. Mei et al., Mol. Biotechnol. 34(2): 165-78 (2006).

In general, the present invention employs, unless otherwise indicated, conventional techniques of chemistry, biophysics, molecular biology, recombinant DNA technology, immunology (especially, e.g., antibody technology), and standard techniques in electrophoresis. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., CS.H.L. Press, Pub. (1999); and Current Protocols in Molecular Biology, eds. Ausubel et al., John Wiley & Sons (1992).

Methods of Use

The present invention further provides a method for treating a bleeding condition in a human subject using a composition of the invention. An exemplary method comprises administering to the subject in need thereof a therapeutically effective amount of a pharmaceutical composition/formulation comprising a chimeric polypeptide having Factor VIII activity, wherein the chimeric polypeptide comprises a Factor VIII portion, which is a single chain Factor VIII, and a second portion.

The bleeding condition can be caused by a blood coagulation disorder. A blood coagulation disorder can also be referred to as a coagulopathy. In one example, the blood coagulation disorder, which can be treated with a pharmaceutical composition of the current disclosure, is hemophilia or von Willebrand disease (vWD). In another example, the blood coagulation disorder, which can be treated with a pharmaceutical composition of the present disclosure is hemophilia A.

In some embodiments, the type of bleeding associated with the bleeding condition is selected from hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath.

In other embodiments, the subject suffering from bleeding condition is in need of treatment for surgery, including, e.g., surgical prophylaxis or pert-operative management. In one example, the surgery is selected from minor surgery and major surgery. Exemplary surgical procedures include tooth extraction, tonsillectomy, inguinal herniotomy, synovectomy, craniotomy, osteosynthesis, trauma surgery, intracranial surgery, intra-abdominal surgery, intrathoracic surgery, joint replacement surgery (e.g., total knee replacement, hip replacement, and the like), heart surgery, and caesarean section.

In another example, the subject is concomitantly treated with FIX. Because the compounds of the invention are capable of activating FIXa, they could be used to pre-activate the FIXa polypeptide before administration of the FIXa to the subject.

The methods of the invention can be practiced on a subject in need of prophylactic treatment or on-demand treatment.

In one embodiment, the prophylaxis regimen is "tailored" to the individual patient, for example, by determining data for each patient and administering Factor VIII of the invention, a single chain Factor VIII polypeptide, at a dosing interval that maintains a trough level of 1-3% FVIII activity. Adjustments can be made when a subject experiences unacceptable bleeding episodes defined as ≥2 spontaneous bleeding episodes over a rolling two-month period. In this case, adjustment will target trough levels of 3-5%. In another embodiment, prophylactic treatment results in prevention and control of bleeding, sustained control of bleeding, sustained protection from bleeding, and/or sustained benefit. Prophylaxis, e.g., sustained protection can be demonstrated by an increased AUC to last measured time point (AUC-LAST) and reduced clearance, resulting in increased terminal t½ compared to short acting FVIII. Prophylaxis can be demonstrated by better Cmax, better Tmax, and/or greater mean residence time versus short-acting FVIII. In some embodiments, prophylaxis results in no spontaneous bleeding episodes within about 24, 36, 48, 72, or 96 hours (e.g., 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 96, 87, 88, 89, 90, 91, 92, 93, 94, 95, or 96 hours), after injection (e.g., the last injection). In certain embodiments, prophylaxis results in greater than 30% (e.g., greater than 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 96, 87, 88, 89, or 90%, for example, greater than 50%), mean reduction in annualized bleeding episodes with once weekly dosing.

Having now described the present invention in detail, the same will be more clearly understood by reference to the following examples, which are included herewith for purposes of illustration only and are not intended to be limiting of the invention. All patents and publications referred to herein are expressly incorporated by reference.

EXAMPLES

Example 1

Cloning, Expression and Purification of Single Chain FVIII-Fc (SC rFVIIIFc)

A plasmid was constructed for expressing recombinant Factor VIII Fc (rFVIIIFc) as a single polypeptide chain. The SC rFVIIIFc construct was designed to be a B-domain deleted FVIII possessing a mutated Turin consensus cleavage site in the connecting sequence between the heavy and light chain sequences (Plantier et al., "B-domain deleted factor FVIII is aggregated and degraded through proteasomal and lysosomal pathways." Thromb Haemostasis, 93(5):824 (2005)). The mutated putative cleavage site was used to create a single chain FVIII that did not separate into the heavy and light chains. Specifically, R1645 and R1648 (corresponding to the full-length FVIII sequence) were substituted to alanine. The mutations were created by overlapping PCR using the following primers:

```
pBUD-BDDF8 BamHI-2565F:
                                    (SEQ ID NO: 24)
5'-GCT TGA GGA TCC AGA GTT CC-3',

BDDF8-R1645A/R164A-R:
                                    (SEQ ID NO: 25)
5'-CGA GTT ATT TCC GCC TGA TGG GCT TTC AAG ACT
GG-3',

BDDF8-R1645A/R1648A-F:
                                    (SEQ ID NO: 26)
5'-CCA GTC TTG AAA GCC CAT CAG GCG GAA ATA ACT
CG-3',
and

pBUD-BDDF8 Kpn21-4245R:
                                    (SEQ ID NO: 27)
5'-TGA TTG ATC CGG AAT AAT GAA G-3'.
```

The template used for the PCR reaction was pBUD/BDD-FVIIIFc/Fc (pBudCE4.1, Invitrogen). The final PCR product was cloned and the sequence confirmed the desired construct having SC BDD FVIIIFc R1645A/R1648A (SEQ ID NO:7). The plasmid was designated pSYN-FV111-014.

HEK293 cells ($1\times10^6$ cells/well of a 6-well plate) were transfected with pSYN-FVIII-014, using Lipofectamine 2000 in OptiMEM medium. After 3 days, cells were plated at 2500 cell/well in 5×96 well plates, and Zeocin was added to a final concentration of 200 μg/mL. Cell lines that survived were transferred to 24-well plates and the concentration of zeocin was reduced to 100 μg/mL. Cell lines expressing the single chain rFVIIIFc were transferred to T25 cm2 flasks. Expression of secreted SC rFVIIIFc was confirmed by protein A pull-downs followed by Western Blot using an anti-Fc antibody. Cells expressing the SC rFVIIIFc were further expanded to T75 cm2 flasks and then to suspension culture containing 50 μg/mL Zeocin. Two cell lines (1E11 and 5G2) were selected for further expansion as both adherent and suspension cultures based on expression of the SC rFVIIIFc by Western Blot analysis at the 24-well stage and were selected in medium containing 50 μg/mL Zeocin. Of the surviving cell lines, the final line that had optimal viability and production levels was "1E11."

Example 2

Biochemical Characterization of Cell Line Expressing rFVIIIFc and rFVIIIFc Activity The 1E11 stable cell line expressing BDD single chain rFVIIIFc was identified as disclosed in Example 1 and expanded for production. Cells were grown in serum-free suspension culture, and rFVIIIFc protein was purified from clarified harvest media using a three-column purification process, including a FVIII-specific affinity purification step (McCue J T, et al., *J Chromatogr A.* 2009; 1216: 7824-30), followed by a combination of anion exchange columns and a hydrophobic interaction column. FIG. 4 shows a Sypro-Ruby stain on Nonreduced (NR) SDS-PAGE gel showing purified single chain FVIII produced from 1E11 cell line (lane 2).

TABLE 1

Polynucleotide Sequences

A. B-Domain Deleted FVIIIFc (i) B-Domain Deleted FVIIIFc Chain DNA Sequence (FVIII signal peptide underlined, Fc region in bold) (SEQ ID NO: 1, which encodes SEQ ID NO: 2)

661 A TGCAAATAGA GCTCTCCACC TGCTTCTTTC
721 TGTGCCTTTT GCGATTCTGC TTTAGTGCCA CCAGAAGATA CTACCTGGGT GCAGTGGAAC
781 TGTCATGGGA CTATATGCAA AGTGATCTCG GTGAGCTGCC TGTGGACGCA AGATTTCCTC
841 CTAGAGTGCC AAAATCTTTT CCATTCAACA CCTCAGTCGT GTACAAAAAG ACTCTGTTTG
901 TAGAATTCAC GGATCACCTT TTCAACATCG CTAAGCCAAG GCCACCCTGG ATGGGTCTGC
961 TAGGTCCTAC CATCCAGGCT GAGGTTTATG ATACAGTGGT CATTACACTT AAGAACATGG
1021 CTTCCCATCC TGTCAGTCTT CATGCTGTTG GTGTATCCTA CTGGAAAGCT TCTGAGGGAG
1081 CTGAATATGA TGATCAGACC AGTCAAAGGG AGAAAGAAGA TGATAAAGTC TTCCCTGGTG
1141 GAAGCCATAC ATATGTCTGG CAGGTCCTGA AAGAGAATGG TCCAATGGCC TCTGACCCAC
1201 TGTGCCTTAC CTACTCATAT CTTTCTCATG TGGACCTGGT AAAAGACTTG AATTCAGGCC
1261 TCATTGGAGC CCTACTAGTA TGTAGAGAAG GGAGTCTGGC CAAGGAAAAG ACACAGACCT
1321 TGCACAAATT TATACTACTT TTTGCTGTAT TTGATGAAGG GAAAAGTTGG CACTCAGAAA
1381 CAAAGAACTC CTTGATGCAG GATAGGGATG CTGCATCTGC TCGGGCCTGG CCTAAAATGC
1441 ACACAGTCAA TGGTTATGTA AACAGGTCTC TGCCAGGTCT GATTGGATGC CACAGGAAAT
1501 CAGTCTATTG GCATGTGATT GGAATGGGCA CCACTCCTGA AGTGCACTCA ATATTCCTCG
1561 AAGGTCACAC ATTTCTTGTG AGGAACCATC GCCAGGCGTC CTTGGAAATC TCGCCAATAA
1621 CTTTCCTTAC TGCTCAAACA CTCTTGATGG ACCTTGGACA GTTTCTACTG TTTTGTCATA
1681 TCTCTTCCCA CCAACATGAT GGCATGGAAG CTTATGTCAA AGTAGACAGC TGTCCAGAGG
1741 AACCCCAACT ACGAATGAAA AATAATGAAG AAGCGGAAGA CTATGATGAT GATCTTACTG
1801 ATTCTGAAAT GGATGTGGTC AGGTTTGATG ATGACAACTC TCCTTCCTTT ATCCAAATTC
1861 GCTCAGTTGC CAAGAAGCAT CCTAAAACTT GGGTACATTA CATTGCTGCT GAAGAGGAGG
1921 ACTGGGACTA TGCTCCCTTA GTCCTCGCCC CCGATGACAG AAGTTATAAA AGTCAATATT
1981 TGAACAATGG CCCTCAGCGG ATTGGTAGGA AGTACAAAAA AGTCCGATTT ATGGCATACA
2041 CAGATGAAAC CTTTAAGACT CGTGAAGCTA TTCAGCATGA ATCAGGAATC TTGGGACCTT
2101 TACTTTATGG GGAAGTTGGA GACACACTGT TGATTATATT TAAGAATCAA GCAAGCAGAC
2161 CATATAACAT CTACCCTCAC GGAATCACTG ATGTCCGTCC TTTGTATTCA AGGAGATTAC
2221 CAAAAGGTGT AAAACATTTG AAGGATTTTC CAATTCTGCC AGGAGAAATA TTCAAATATA
2281 AATGGACAGT GACTGTAGAA GATGGGCCAA CTAAATCAGA TCCTCGGTGC CTGACCCGCT
2341 ATTACTCTAG TTTCGTTAAT ATGGAGAGAG ATCTAGCTTC AGGACTCATT GGCCCTCTCC
2401 TCATCTGCTA CAAAGAATCT GTAGATCAAA GAGGAAACCA GATAATGTCA GACAAGAGGA
2461 ATGTCATCCT GTTTTCTGTA TTTGATGAGA ACCGAAGCTG GTACCTCACA GAGAATATAC
2521 AACGCTTTCT CCCCAATCCA GCTGGAGTGC AGCTTGAGGA TCCAGAGTTC CAAGCCTCCA
2581 ACATCATGCA CAGCATCAAT GGCTATGTTT TTGATAGTTT GCAGTTGTCA GTTTGTTTGC
2641 ATGAGGTGGC ATACTGGTAC ATTCTAAGCA TTGGAGCACA GACTGACTTC CTTTCTGTCT
2701 TCTTCTCTGG ATATACCTTC AAACACAAAA TGGTCTATGA AGACACACTC ACCCTATTCC
2761 CATTCTCAGG AGAAACTGTC TTCATGTCGA TGGAAAACCC AGGTCTATGG ATTCTGGGGT
2821 GCCACAACTC AGACTTTCGG AACAGAGGCA TGACCGCCTT ACTGAAGGTT TCTAGTTGTG
2881 ACAAGAACAC TGGTGATTAT TACGAGGACA GTTATGAAGA TATTTCAGCA TACTTGCTGA
2941 GTAAAAACAA TGCCATTGAA CCAAGAAGCT TCTCTCAAAA CCCACCAGTC TTGAAACGCC
3001 ATCAACGGGA AATAACTCGT ACTACTCTTC AGTCAGATCA AGAGGAAATT GACTATGATG
3061 ATACCATATC AGTTGAAATG AAGAAGGAAG ATTTTGACAT TTATGATGAG GATGAAAATC
3121 AGAGCCCCCG CAGCTTTCAA AAGAAAACAC GACACTATTT TATTGCTGCA GTGGAGAGGC
3181 TCTGGGATTA TGGGATGAGT AGCTCCCCAC ATGTTCTAAG AAACAGGGCT CAGAGTGGCA
3241 GTGTCCCTCA GTTCAAGAAA GTTGTTTTCC AGGAATTTAC TGATGGCTCC TTTACTCAGC
3301 CCTTATACCG TGGAGAACTA AATGAACATT TGGGACTCCT GGGGCCATAT ATAAGAGCAG
3361 AAGTTGAAGA TAATATCATG GTAACTTTCA GAAATCAGGC CTCTCGTCCC TATTCCTTCT
3421 ATTCTAGCCT TATTTCTTAT GAGGAAGATC AGAGGCAAGG AGCAGAACCT AGAAAAAACT
3481 TTGTCAAGCC TAATGAAACC AAAACTTACT TTTGGAAAGT GCAACATCAT ATGGCACCCA
3541 CTAAAGATGA GTTTGACTGC AAAGCCTGGG CTTATTTCTC TGATGTTGAC CTGGAAAAAG
3601 ATGTGCACTC AGGCCTGATT GGACCCCTTC TGGTCTGCCA CACTAACACA CTGAACCCTG
3661 CTCATGGGAG ACAAGTGACA GTACAGGAAT TTGCTCTGTT TTTCACCATC TTTGATGAGA
3721 CCAAAAGCTG GTACTTCACT GAAAATATGG AAAGAAACTG CAGGGCTCCC TGCAATATCC
3781 AGATGGAAGA TCCCACTTTT AAAGAGAATT ATCGCTTCCA TGCAATCAAT GGCTACATAA
3841 TGGATACACT ACCTGGCTTA GTAATGGCTC AGGATCAAAG GATTCGATGG TATCTGCTCA
3901 GCATGGGCAG CAATGAAAAC ATCCATTCTA TTCATTTCAG TGGACATGTG TTCACTGTAC
3961 GAAAAAAAGA GGAGTATAAA ATGGCACTGT ACAATCTCTA TCCAGGTGTT TTTGAGACAG
4021 TGGAAATGTT ACCATCCAAA GCTGGAATTT GGCGGGTGGA ATGCCTTATT GGCGAGCATC
4081 TACATGCTGG GATGAGCACA CTTTTTCTGG TGTACAGCAA TAAGTGTCAG ACTCCCCTGG
4141 GAATGGCTTC TGGACACATT AGAGATTTTC AGATTACAGC TTCAGGACAA TATGGACAGT
4201 GGGCCCCAAA GCTGGCCAGA CTTCATTATT CCGGATCAAT CAATGCCTGG AGCACCAAGG
4261 AGCCCTTTTC TTGGATCAAG GTGGATCTGT TGGCACCAAT GATTATTCAC GGCATCAAGA
4321 CCCAGGGTGC CCGTCAGAAG TTCTCCAGCC TCTACATCTC TCAGTTTATC ATCATGTATA
4381 GTCTTGATGG GAAGAAGTGG CAGACTTATC GAGGAAATTC CACTGGAACC TTAATGGTCT
4441 TCTTTGGCAA TGTGGATTCA TCTGGGATAA AACACAATAT TTTTAACCCT CCAATTATTG
4501 CTCGATACAT CCGTTTGCAC CCAACTCATT ATAGCATTCG CAGCACTCTT CGCATGGAGT
4561 TGATGGGCTG TGATTTAAAT AGTTGCAGCA TGCCATTGGG AATGGAGAGT AAAGCAATAT
4621 CAGATGCACA GATTACTGCT TCATCCTACT TTACCAATAT GTTTGCCACC TGGTCTCCTT
4681 CAAAAGCTCG ACTTCACCTC CAAGGGAGGA GTAATGCCTG GAGACCTCAG GTGAATAATC
4741 CAAAAGAGTG GCTGCAAGTG GACTTCCAGA AGACAATGAA AGTCACAGGA GTAACTACTC
4801 AGGGAGTAAA ATCTCTGCTT ACCAGCATGT ATGTGAAGGA GTTCCTCATC TCCAGCAGTC
4861 AAGATGGCCA TCAGTGGACT CTCTTTTTTC AGAATGGCAA AGTAAAGGTT TTTCAGGGAA
4921 ATCAAGACTC CTTCACACCT GTGGTGAACT CTCTAGACCC ACCGTTACTG ACTCGCTACC
4981 TTCGAATTCA CCCCCAGAGT TGGGTGCACC AGATTGCCCT GAGGATGGAG GTTCTGGGCT
5041 GCGAGGCACA GGACCTCTAC GACAAAACTC ACACATGCCC ACCGTGCCCA GCTCCAGAAC
5101 TCCTGGGCGG ACCGTCAGTC TTCCTCTTCC CCCCAAAACC CAAGGACACC CTCATGATCT

TABLE 1-continued

Polynucleotide Sequences

5161 CCCGGACCCC TGAGGTCACA TGCGTGGTGG TGGACGTGAG CCACGAAGAC CCTGAGGTCA
5221 AGTTCAACTG GTACGTGGAC GGCGTGGAGG TGCATAATGC CAAGACAAAG CCGCGGGAGG
5281 AGCAGTACAA CAGCACGTAC CGTGTGGTCA GCGTCCTCAC CGTCCTGCAC CAGGACTGGC
5341 TGAATGGCAA GGAGTACAAG TGCAAGGTCT CCAACAAAGC CCTCCCAGCC CCCATCGAGA
5401 AAACCATCTC CAAAGCCAAA GGGCAGCCCC GAGAACCACA GGTGTACACC CTGCCCCCAT
5461 CCCGGGATGA GCTGACCAAG AACCAGGTCA GCCTGACCTG CCTGGTCAAA GGCTTCTATC
5521 CCAGCGACAT CGCCGTGGAG TGGGAGAGCA ATGGGCAGCC GGAGAACAAC TACAAGACCA
5581 CGCCTCCCGT GTTGGACTCC GACGGCTCCT TCTTCCTCTA CAGCAAGCTC ACCGTGGACA
5641 AGAGCAGGTG GCAGCAGGGG AACGTCTTCT CATGCTCCGT GATGCATGAG GCTCTGCACA
5701 ACCACTACAC GCAGAAGAGC CTCTCCCTGT CTCCGGGTAA A

(ii) Fc DNA sequence (mouse Igκ signal peptide underlined) (SEQ ID NO: 3, which encodes SEQ ID NO: 4)

7981 ATGGA GACAGACACA
8041 CTCCTGCTAT GGGTACTGCT GCTCTGGGTT CCAGGTTCCA CTGGTGACAA AACTCACACA
8101 TGCCCACCGT GCCCAGCACC TGAACTCCTG GGAGGACCGT CAGTCTTCCT CTTCCCCCCA
8161 AAACCCAAGG ACACCCTCAT GATCTCCCGG ACCCCTGAGG TCACATGCGT GGTGGTGGAC
8221 GTGAGCCACG AAGACCCTGA GGTCAAGTTC AACTGGTACG TGGACGGCGT GGAGGTGCAT
8281 AATGCCAAGA CAAAGCCGCG GGAGGAGCAG TACAACAGCA CGTACCGTGT GGTCAGCGTC
8341 CTCACCGTCC TGCACCAGGA CTGGCTGAAT GGCAAGGAGT ACAAGTGCAA GGTCTCCAAC
8401 AAAGCCCTCC CAGCCCCCAT CGAGAAAACC ATCTCCAAAG CCAAAGGGCA GCCCCGAGAA
8461 CCACAGGTGT ACACCCTGCC CCCATCCCGC GATGAGCTGA CCAAGAACCA GGTCAGCCTG
8521 ACCTGCCTGG TCAAAGGCTT CTATCCCAGC GACATCGCCG TGGAGTGGGA GAGCAATGGG
8581 CAGCCGGAGA ACAACTACAA GACCACGCCT CCCGTGTTGG ACTCCGACGG CTCCTTCTTC
8641 CTCTACAGCA AGCTCACCGT GGACAAGAGC AGGTGGCAGC AGGGGAACGT CTTCTCATGC
8701 TCCGTGATGC ATGAGGCTCT GCACAACCAC TACACGCAGA AGAGCCTCTC CCTGTCTCCG
8761 GGTAAA

B. Full Length FVIIIFc (i) Full Length FVIIIFc DNA Sequence (FVIII signal made underlined, Fc region in bold) (SEQ ID NO: 5, which encodes SEQ ID NO: 6)

661 ATG CAAATAGAGC TCTCCACCTG
721 CTTCTTTCTG TGCCTTTTGC GATTCTGCTT TAGTGCCACC AGAAGATACT ACCTGGGTGC
781 AGTGGAACTG TCATGGGACT ATATGCAAAG TGATCTCGGT GAGCTGCCTG TGGACGCAAG
841 ATTTCCTCCT AGAGTGCCAA AATCTTTTCC ATTCAACACC TCAGTCGTGT ACAAAAAGAC
901 TCTGTTTGTA GAATTCACGG ATCACCTTTT CAACATCGCT AAGCCAAGGC CACCCTGGAT
961 GGGTCTGCTA GGTCCTACCA TCCAGGCTGA GGTTTATGAT ACAGTGGTCA TTACACTTAA
1021 GAACATGGCT TCCCATCCTG TCAGTCTTCA TGCTGTTGGT GTATCCTACT GGAAAGCTTC
1081 TGAGGGAGCT GAATATGATG ATCAGACCAG TCAAAGGGAG AAAGAAGATG ATAAAGTCTT
1141 CCCTGGTGGA AGCCATACAT ATGTCTGGCA GGTCCTGAAA GAGAATGGTC CAATGGCCTC
1201 TGACCCACTG TGCCTTACCT ACTCATATCT TTCTCATGTG GACCTGGTAA AAGACTTGAA
1261 TTCAGGCCTC ATTGGAGCCC TACTAGTATG TAGAGAAGGG AGTCTGGCCA AGGAAAAGAC
1321 ACAGACCTTG CACAAATTTA TACTACTTTT TGCTGTATTT GATGAAGGGA AAAGTTGGCA
1381 CTCAGAAACA AAGAACTCCT TGATGCAGGA TAGGGATGCT GCATCTGCTC GGGCCTGGCC
1441 TAAAATGCAC ACAGTCAATG GTTATGTAAA CAGGTCTCTG CCAGGTCTGA TTGGATGCCA
1501 CAGGAAATCA GTCTATTGGC ATGTGATTGG AATGGGCACC ACTCCTGAAG TGCACTCAAT
1561 ATTCCTCGAA GGTCACACAT TTCTTGTGAG GAACCATCGC CAGGCGTCCT TGGAAATCTC
1621 GCCAATAACT TTCCTTACTG CTCAAACACT CTTGATGGAC CTTGGACAGT TTCTACTGTT
1681 TTGTCATATC TCTTCCCACC AACATGATGG CATGGAAGCT TATGTCAAAG TAGACAGCTG
1741 TCCAGAGGAA CCCCAACTAC GAATGAAAAA TAATGAAGAA GCGGAAGACT ATGATGATGA
1801 TCTTACTGAT TCTGAAATGG ATGTGGTCAG GTTTGATGAT GACAACTCTC CTTCCTTTAT
1861 CCAAATTCGC TCAGTTGCCA AGAAGCATCC TAAAACTTGG GTACATTACA TTGCTGCTGA
1921 AGAGGAGGAC TGGGACTATG CTCCCTTAGT CCTCGCCCCC GATGACAGAA GTTATAAAAG
1981 TCAATATTTG AACAATGGCC CTCAGCGGAT TGGTAGGAAG TACAAAAAAG TCCGATTTAT
2041 GGCATACACA GATGAAACCT TTAAGACTCG TGAAGCTATT CAGCATGAAT CAGGAATCTT
2101 GGGACCTTTA CTTTATGGGG AAGTTGGAGA CACACTGTTG ATTATATTTA AGAATCAAGC
2161 AAGCAGACCA TATAACATCT ACCCTCACGG AATCACTGAT GTCCGTCCTT TGTATTCAAG
2221 GAGATTACCA AAAGGTGTAA AACATTTGAA GGATTTTCCA ATTCTGCCAG GAGAAATATT
2281 CAAATATAAA TGGACAGTGA CTGTAGAAGA TGGGCCAACT AAATCAGATC CTCGGTGCCT
2341 GACCCGCTAT TACTCTAGTT TCGTTAATAT GGAGAGAGAT CTAGCTTCAG GACTCATTGG
2401 CCCTCTCCTC ATCTGCTACA AAGAATCTGT AGATCAAAGA GGAAACCAGA TAATGTCAGA
2461 CAAGAGGAAT GTCATCCTGT TTTCTGTATT TGATGAGAAC CGAAGCTGGT ACCTCACAGA
2521 GAATATACAA CGCTTTCTCC CCAATCCAGC TGGAGTGCAG CTTGAGGATC CAGAGTTCCA
2581 AGCCTCCAAC ATCATGCACA GCATCAATGG CTATGTTTTT GATAGTTTGC AGTTGTCAGT
2641 TTGTTTGCAT GAGGTGGCAT ACTGGTACAT TCTAAGCATT GGAGCACAGA CTGACTTCCT
2701 TTCTGTCTTC TTCTCTGGAT ATACCTTCAA ACACAAAATG GTCTATGAAG ACACACTCAC
2761 CCTATTCCCA TTCTCAGGAG AAACTGTCTT CATGTCGATG GAAAACCCAG GTCTATGGAT
2821 TCTGGGGTGC CACAACTCAG ACTTTCGGAA CAGAGGCATG ACCGCCTTAC TGAAGGTTTC
2881 TAGTTGTGAC AAGAACACTG GTGATTATTA CGAGGACAGT TATGAAGATA TTTCAGCATA
2941 CTTGCTGAGT AAAAACAATG CCATTGAACC AAGAAGCTTC TCCCAGAATT CAAGACACCC
3001 TAGCACTAGG CAAAAGCAAT TTAATGCCAC CACAATTCCA GAAAATGACA TAGAGAAGAC
3061 TGACCCTTGG TTTGCACACA GAACACCTAT GCCTAAAATA CAAAATGTCT CCTCTAGTGA
3121 TTTGTTGATG CTCTTGCGAC AGAGTCCTAC TCCACATGGG CTATCCTTAT CTGATCTCCA
3181 AGAAGCCAAA TATGAGACTT TTTCTGATGA TCCATCACCT GGAGCAATAG ACAGTAATAA
3241 CAGCCTGTCT GAAATGACAC ACTTCAGGCC ACAGCTCCAT CACAGTGGGG ACATGGTATT
3301 TACCCCTGAG TCAGGCCTCC AATTAAGATT AAATGAGAAA CTGGGGACAA CTGCAGCAAC
3361 AGAGTTGAAG AAACTTGATT TCAAAGTTTC TAGTACATCA AATAATCTGA TTTCAACAAT
3421 TCCATCAGAC AATTTGGCAG CAGGTACTGA TAATACAAGT TCCTTAGGAC CCCCAAGTAT

TABLE 1-continued

| Polynucleotide Sequences |
|---|
| 3481 GCCAGTTCAT TATGATAGTC AATTAGATAC CACTCTATTT GGCAAAAAGT CATCTCCCCT |
| 3541 TACTGAGTCT GGTGGACCTC TGAGCTTGAG TGAAGAAAAT AATGATTCAA AGTTGTTAGA |
| 3601 ATCAGGTTTA ATGAATAGCC AAGAAAGTTC ATGGGGAAAA AATGTATCGT CAACAGAGAG |
| 3661 TGGTAGGTTA TTTAAAGGGA AAAGAGCTCA TGGACCTGCT TTGTTGACTA AAGATAATGC |
| 3721 CTTATTCAAA GTTAGCATCT CTTTGTTAAA GACAAACAAA ACTTCCAATA ATTCAGCAAC |
| 3781 TAATAGAAAG ACTCACATTG ATGGCCCATC ATTATTAATT GAGAATAGTC CATCAGTCTG |
| 3841 GCAAAATATA TTAGAAAGTG ACACTGAGTT TTAGAAAGTG ACACCTTTGA TTCATGACAG |
| 3901 AATGCTTATG GACAAAAATG CTACAGCTTT GAGGCTAAAT CATATGTCAA ATAAAACTAC |
| 3961 TTCATCAAAA AACATGGAAA TGGTCCAACA GAAAAAAGAG GGCCCCATTC CACCAGATGC |
| 4021 ACAAAATCCA GATATGTCGT TCTTTAAGAT GCTATTCTTG CCAGAATCAG CAAGGTGGAT |
| 4081 ACAAAGGACT CATGGAAAGA ACTCTCTGAA CTCTGGGCAA GGCCCCAGTC CAAAGCAATT |
| 4141 AGTATCCTTA GGACCAGAAA AATCTGTGGA AGGTCAGAAT TTCTTGTCTG AGAAAAACAA |
| 4201 AGTGGTAGTA GGAAAGGGTG AATTTACAAA GGACGTAGGA CTCAAAGAGA TGGTTTTTCC |
| 4261 AAGCAGCAGA AACCTATTTC TTACTAACTT GGATAATTTA CATGAAAATA ATACACACAA |
| 4321 TCAAGAAAAA AAAATTCAGG AAGAAATAGA AAAGAAGGAA ACATTAATCC AAGAGAATGT |
| 4381 AGTTTTGCCT CAGATACATA CAGTGACTGG CACTAAGAAT TTCATGAAGA ACCTTTTCTT |
| 4441 ACTGAGCACT ACACAAAATG TAGAAGGTTC ATATGACGGG GCATATGCTC CAGTACTTCA |
| 4501 AGATTTTAGG TCATTAAATG ATTCAACAAA TAGAACAAAG AAACACACAG CTCATTTCTC |
| 4561 AAAAAAAGGG GAGGAAGAAA ACTTGGAAGG CTTGGGAAAT CAAACCAAGC AAATTGTAGA |
| 4621 GAAATATGCA TGCACCACAA GGATATCTCC TAATACAAGC CAGCAGAATT TTGTCACGCA |
| 4681 ACGTAGTAAG AGAGCTTTGA AACAATTCAG ACTCCCACTA GAAGAAACAG AACTTGAAAA |
| 4741 AAGGATAATT GTGGATGACA CCTCAACCCA GTGGTCCAAA AACATGAAA0 ATTTGACCCC |
| 4801 GAGCACCCTC ACACAGATAG ACTACAATGA GAAGGAGAAA GGGGCCATTA CTCAGTCTCC |
| 4861 CTTATCAGAT TGCCTTACGA GGAGTCATAG CATCCCTCAA GCAAATAGAT CTCCATTACC |
| 4921 CATTGCAAAG GTATCATCAT TTCCATCTAT TAGACCTATA TATCTGACCA GGGTCCTATT |
| 4981 CCAAGACAAC TCTTCTCATC TTCCAGCAGC ATCTTATAGA AAGAAAGATT CTGGGGTCCA |
| 5041 AGAAAGCAGT CATTTCTTAC AAGGAGCCAA AAAAAATAAC CTTTCTTTAG CCATTCTAAC |
| 5101 CTTGGAGATG ACTGGTGATC AAAGAGAGGT TGGCTCCCTG GGGACAAGTG CCACAAATTC |
| 5161 AGTCACATAC AAGAAAGTTG AGAACACTGT TCTCCCGAAA CCAGACTTGC CCAAAACATC |
| 5221 TGGCAAAGTT GAATTGCTTC CAAAAGTTCA CATTTATCAG AAGGACCTAT TCCCTACGGA |
| 5281 AACTAGCAAT GGGTCTCCTG GCCATCTGGA TCTCGTGGAA GGGAGCCTTC TTCAGGGAAC |
| 5341 AGAGGGAGCG ATTAAGTGGA ATGAAGCAAA CAGACCTGGA AAAGTTCCCT TTCTGAGAGT |
| 5401 AGCAACAGAA AGCTCTGCAA AGACTCCCTC CAAGCTATTG GATCCTCTTG CTTGGGATAA |
| 5461 CCACTATGGT ACTCAGATAC CAAAAGAAGA GTGGAAATCC CAAGAGAAGT CACCAGAAAA |
| 5521 AACAGCTTTT AAGAAAAAGG ATACCATTTT GICCCTGAAC GCTTGTGAAA GCAATCATGC |
| 5581 AATAGCAGCA ATAAATGAGG GACAAAATAA GCCCGAAATA GAAGTCACCT GGGCAAAGCA |
| 5641 AGGTAGGACT GAAAGGCTGT GCTCTCAAAA CCCACCAGTC TTGAAACGCC ATCAACGGGA |
| 5701 AATAACTCGT ACTACTCTTC AGTCAGATCA AGAGGAAATT GACTATGATG ATACCATATC |
| 5/61 AGTTGAAATG AAGAAGGAAG ATTTTGACAT TTATGATGAG GATGAAAATC AGAGCCCCCG |
| 5821 CAGCTTTCAA AAGAAAACAC GACACTATTT TATTGCTGCA GTGGAGAGGC TCTGGGATTA |
| 5881 TGGGATGAGT AGCTCCCCAC ATGTTCTAAG AAACAGGGCT CAGAGTGGCA GTGTCCCTCA |
| 5941 GTTCAAGAAA GTTGTTTTCC AGGAATTTAC TGATGGCTCC TTTACTCAGC CCTTATACCG |
| 6001 TGGAGAACTA AATGAACATT TGGGACTCCT GGGGCCATAT ATAAGAGCAG AAGTTGAAGA |
| 6061 TAATATCATG GTAACTTTCA GAAATCAGGC CTCTCGTCCC TATTCCTTCT ATTCTAGCCT |
| 6121 TATTTCTTAT GAGGAAGATC AGAGGCAAGG AGCAGAACCT AGAAAAAACT TTGTCAAGCC |
| 6181 TAATGAAACC AAAACTTACT TTTGGAAAGT GCAACATCAT ATGGCACCCA CTAAAGATGA |
| 6241 GTTTGACTGC AAAGCCTGGG CTTATTTCTC TGATGTTGAC CTGGAAAAAG ATGTGCACTC |
| 6301 AGGCCTGATT GGACCCCTTC TGGTCTGCCA CACTAACACA CTGAACCCTG CTCATGGGAG |
| 6361 ACAAGTGACA GTACAGGAAT TTGCTCTGTT TTTCACCATC TTTGATGAGA CCAAAAGCTG |
| 6421 GTACTTCACT GAAAATATGG AAAGAAACTG CAGGGCTCCC TGCAATATCC AGATGGAAGA |
| 6481 TCCCACTTTT AAAGAGAATT ATCGCTTCCA TGCAATCAAT GGCTACATAA TGGATACACT |
| 6541 ACCTGGCTTA GTAATGGCTC AGGATCAAAG GATTCGATGG TATCTGCTCA GCATGGGCAG |
| 6601 CAATGAAAAC ATCCATTCTA TTCATTTCAG TGGACATGTG TTCACTGTAC GAAAAAAAGA |
| 6661 GGAGTATAAA ATGGCACTGT ACAATCTCTA TCCAGGTGTT TTTGAGACAG TGGAAATGTT |
| 6721 ACCATCCAAA GCTGGAATTT GGCGGGTGGA ATGCCTTATT GGCGAGCATC TACATGCTGG |
| 6781 GATGAGCACA CTTTTTCTGG TGTACAGCAA TAAGTGTCAG ACTCCCCTGG GAATGGCTTC |
| 6841 TGGACACATT AGAGATTTTC AGATTACAGC TTCAGGACAA TATGGACAGT GGGCCCCAAA |
| 6901 GCTGGCCAGA CTTCATTATT CCGGATCAAT CAATGCCTGG AGCACCAAGG AGCCCTTTTC |
| 6961 TTGGATCAAG GTGGATCTGT TGGCACCAAT GATTATTCAC GGCATCAAGA CCCAGGGTGC |
| 7021 CCGTCAGAAG TTCTCCAGCC TCTACATCTC TCAGTTTATC ATCATGTATA GTCTTGATGG |
| 7081 GAAGAAGTGG CAGACTTATC GAGGAAATTC CACTGGAACC TTAATGGTCT TCTTTGGCAA |
| 7141 TGTGGATTCA TCTGGGATAA AACACAATAT TTTTAACCCT CCAATTATTG CTCGATACAT |
| 7201 CCGTTTGCAC CCAACTCATT ATAGCATTCG CAGCACTCTT CGCATGGAGT TGATGGGCTG |
| 7261 TGATTTAAAT AGTTGCAGCA TGCCATTGGG AATGGAGAGT AAAGCAATAT CAGATGCACA |
| 7321 GATTACTGCT TCATCCTACT TTACCAATAT GTTTGCCACC TGGTCTCCTT CAAAAGCTCG |
| 7381 ACTTCACCTC CAAGGGAGGA GTAATGCCTG GAGACCTCAG GTGAATAATC CAAAAGAGTG |
| 7441 GCTGCAAGTG GACTTCCAGA AGACAATGAA AGTCACAGGA GTAACTACTC AGGGAGTAAA |
| 7501 ATCTCTGCTT ACCAGCATGT ATGTGAAGGA GTTCCTCATC TCCAGCAGTC AAGATGGCCA |
| 7561 TCAGTGGACT CTCTTTTTTC AGAATGGCAA AGTAAAGGTT TTTCAGGGAA ATCAAGACTC |
| 7621 CTTCACACCT GTGGTGAACT CTCTAGACCC ACCGTTACTG ACTCGCTACC TTCGAATTCA |
| 7681 CCCCCAGAGT TGGGTGCACC AGATTGCCCT GAGGATGGAG GTTCTGGGCT GCGAGGCACA |
| 7741 GGACCTCTAC **GACAAAACTC ACACATGCCC ACCGTGCCCA GCTCCAGAAC TCCTGGGCGG** |
| 7801 **ACCGTCAGTC TTCCTCTTCC CCCCAAAACC CAAGGACACC CTCATGATCT CCCGGACCCC** |
| 7861 **TGAGGTCACA TGCGTGGTGG TGGACGTGAG CCACGAAGAC CCTGAGGTCA AGTTCAACTG** |
| 7921 **GTACGTGGAC GGCGTGGAGG TGCATAATGC CAAGACAAAG CCGCGGGAGG AGCAGTACAA** |
| 7981 **CAGCACGTAC CGTGTGGTCA GCGTCCTCAC CGTCCTGCAC CAGGACTGGC TGAATGGCAA** |
| 8041 **GGAGTACAAG TGCAAGGTCT CCAACAAAGC CCTCCCAGCC CCCATCGAGA AAACCATCTC** |
| 8101 **CAAAGCCAAA GGGCAGCCCC GAGAACCACA GGTGTACACC CTGCCCCCAT CCCGGGATGA** |

TABLE 1-continued

Polynucleotide Sequences

8161 GCTGACCAAG AACCAGGTCA GCCTGACCTG CCTGGTCAAA GGCTTCTATC CCAGCGACAT
8221 CGCCGTGGAG TGGGAGAGCA ATGGGCAGCC GGAGAACAAC TACAAGACCA CGCCTCCCGT
8281 GTTGGACTCC GACGGCTCCT TCTTCCTCTA CAGCAAGCTC ACCGTGGACA AGAGCAGGTG
8341 GCAGCAGGGG AACGTCTTCT CATGCTCCGT GATGCATGAG GCTCTGCACA ACCACTACAC
8401 GCAGAAGAGC CTCTCCCTGT CTCCGGGTAA A

(ii) Fc (same sequence as A (ii) (SEQ ID NO: 3))]
C. Single Chain BDD rFVIIIFc Polynucleotide
(i) Single Chain (SC) B-Domain Deleted rFVIIIFc Chain DNA sequence (FVIII signal peptide underlined, R1645A/R1648A bold and underlined, Fc region in bold).

1 ATGCAAATAG AGCTCTCCAC CTGCTTCTTT CTGTGCCTTT TGCGATTCTG CTTTAGTGCC
61 ACCAGAAGAT ACTACCTGGG TGCAGTGGAA CTGTCATGGG ACTATATGCA AAGTGATCTC
121 GGTGAGCTGC CTGTGGACGC AAGATTTCCT CCTAGAGTGC CAAAATCTTT TCCATTCAAC
181 ACCTCAGTCG TGTACAAAAA GACTCTGTTT GTAGAATTCA CGGATCACCT TTTCAACATC
241 GCTAAGCCAA GGCCACCCTG GATGGGTCTG CTAGGTCCTA CCATCCAGGC TGAGGTTTAT
301 GATACAGTGG TCATTACACT TAAGAACATG GCTTCCCATC CTGTCAGTCT TCATGCTGTT
361 GGTGTATCCT ACTGGAAAGC TTCTGAGGGA GCTGAATATG ATGATCAGAC CAGTCAAAGG
421 GAGAAAGAAG ATGATAAAGT CTTCCCTGGT GGAAGCCATA CATATGTCTG GCAGGTCCTG
481 AAAGAGAATG GTCCAATGGC CTCTGACCCA CTGTGCCTTA CCTACTCATA TCTTTCTCAT
541 GTGGACCTGG TAAAAGACTT GAATTCAGGC CTCATTGGAG CCCTACTAGT ATGTAGAGAA
601 GGGAGTCTGG CCAAGGAAAA GACACAGACC TTGCACAAAT TTATACTACT TTTTGCTGTA
661 TTTGATGAAG GGAAAAGTTG GCACTCAGAA ACAAAGAACT CCTTGATGCA GGATAGGGAT
721 GCTGCATCTG CTCGGGCCTG GCCTAAAATG CACACAGTCA ATGGTTATGT AAACAGGTCT
781 CTGCCAGGTC TGATTGGATG CCACAGGAAA TCAGTCTATT GGCATGTGAT TGGAATGGGC
841 ACCACTCCTG AAGTGCACTC AATATTCCTC GAAGGTCACA CATTTCTTGT GAGGAACCAT
901 CGCCAGGCGT CCTTGGAAAT CTCGCCAATA ACTTTCCTTA CTGCTCAAAC ACTCTTGATG
961 GACCTTGGAC AGTTTCTACT GTTTTGTCAT ATCTCTTCCC ACCAACATGA TGGCATGGAA
1021 GCTTATGTCA AAGTAGACAG CTGTCCAGAG GAACCCCAAC TACGAATGAA AAATAATGAA
1081 GAAGCGGAAG ACTATGATGA TGATCTTACT GATTCTGAAA TGGATGTGGT CAGGTTTGAT
1141 GATGACAACT CTCCTTCCTT TATCCAAATT CGCTCAGTTG CCAAGAAGCA TCCTAAAACT
1201 TGGGTACATT ACATTGCTGC TGAAGAGGAG GACTGGGACT ATGCTCCCTT AGTCCTCGCC
1261 CCCGATGACA GAAGTTATAA AAGTCAATAT TTGAACAATG GCCCTCAGCG GATTGGTAGG
1321 AAGTACAAAA AAGTCCGATT TATGGCATAC ACAGATGAAA CCTTTAAGAC TCGTGAAGCT
1381 ATTCAGCATG AATCAGGAAT CTTGGGACCT TTACTTTATG GGGAAGTTGG AGACACACTG
1441 TTGATTATAT TTAAGAATCA AGCAAGCAGA CCATATAACA TCTACCCTCA CGGAATCACT
1501 GATGTCCGTC CTTTGTATTC AAGGAGATTA CCAAAAGGTG TAAAACATTT GAAGGATTTT
1561 CCAATTCTGC CAGGAGAAAT ATTCAAATAT AAATGGACAG TGACTGTAGA AGATGGGCCA
1521 ACTAAATCAG ATCCTCGGTG CCTGACCCGC TATTACTCTA GTTTCGTTAA TATGGAGAGA
1681 GATCTAGCTT CAGGACTCAT TGGCCCTCTC CTCATCTGCT ACAAAGAATC TGTAGATCAA
1741 AGAGGAAACC AGATAATGTC AGACAAGAGG AATGTCATCC TGTTTTCTGT ATTTGATGAG
1801 AACCGAAGCT GGTACCTCAC AGAGAATATA CAACGCTTTC TCCCCAATCC AGCTGGAGTG
1961 CAGCTTGAGG ATCCAGAGTT CCAAGCCTCC AACATCATGC ACAGCATCAA TGGCTATGTT
1521 TTTGATACTT TGCAOTTGTC AGTTTGTTTG CATGAGGTGG CATACTGGTA CATTCTAAGC
1981 ATTGGAGCAC AGACTGACTT CCTTTCTGTC TTCTTCTCTG GATATACCTT CAAACACAAA
2041 ATGGTCTATG AAGACACACT CACCCTATTC CCATTCTCAG GAGAAACTGT CTTCATGTCG
2101 ATGGAAAACC CAGGTCTATG GATTCTGGGG TGCCACAACT CAGACTTTCG GAACAGAGGC
2161 ATGACCGCCT TACTGAAGGT TTCTAGTTGT GACAAGAACA CTGGTGATTA TTACGAGGAC
2221 AGTTATGAAG ATATTTCAGC ATACTTGCTG AGTAAAAACA ATGCCATTGA ACCAAGAAGC
2281 TTCTCTCAAA ACCCACCAGT CTTGAAAGCC CATCAGGCGG AAATAACTCG TACTACTCTT
2341 CAGTCAGATC AAGAGGAAAT TGACTATGAT GATACCATAT CAGTTGAAAT GAAGAAGGAA
2401 GATTTTGACA TTTATGATGA GGATGAAAAT CAGAGCCCCC GCAGCTTTCA AAAGAAAACA
2461 CGACACTATT TTATTGCTGC AGTGGAGAGG CTCTGGGATT ATGGGATGAG TAGCTCCCCA
2521 CATGTTCTAA GAAACAGGGC TCAGAGTGGC AGTGTCCCTC AGTTCAAGAA AGTTGTTTTC
2581 CAGGAATTTA CTGATGGCTC CTTTACTCAG CCCTTATACC GTGGAGAACT AAATGAACAT
2641 TTGGGACTCC TGGGGCCATA TATAAGAGCA GAAGTTGAAG ATAATATCAT GGTAACTTTC
2701 AGAAATCAGG CCTCTCGTCC CTATTCCTTC TATTCTAGCC TTATTTCTTA TGAGGAAGAT
2761 CAGAGGCAAG GAGCAGAACC TAGAAAAAAC TTTGTCAAGC CTAATGAAAC CAAAACTTAC
2821 TTTTGGAAAG TGCAACATCA TATGGCACCC ACTAAAGATG AGTTTGACTG CAAAGCCTGG
2881 GCTTATTTCT CTGATGTTGA CCTGGAAAAA GATGTGCACT CAGGCCTGAT TGGACCCCTT
2941 CTGGTCTGCC ACACTAACAC ACTGAACCCT GCTCATGGGA GACAAGTGAC AGTACAGGAA
3001 TTTGCTCTGT TTTTCACCAT CTTTGATGAG ACCAAAAGCT GGTACTTCAC TGAAAATATG
3061 GAAAGAAACT GCAGGGCTCC CTGCAATATC CAGATGGAAG ATCCCACTTT TAAAGAGAAT
3121 TATCGCTTCC ATGCAATCAA TGGCTACATA ATGGATACAC TACCTGGCTT AGTAATGGCT
3181 CAGGATCAAA GGATTCGATG GTATCTGCTC AGCATGGGCA GCAATGAAAA CATCCATTCT
3241 ATTCATTTCA GTGGACATGT GTTCACTGTA CGAAAAAAAG AGGAGTATAA AATGGCACTG
3301 TACAATCTCT ATCCAGGTGT TTTTGAGACA GTGGAAATGT TACCATCCAA AGCTGGAATT
3361 TGGCGGGTGG AATGCCTTAT TGGCGAGCAT CTACATGCTG GGATGAGCAC ACTTTTTCTG
3421 GTGTACAGGA ATAAGTGTCA GACTCCCCTG GGAATGGCTT CTGGACACAT TAGAGATTTT
3481 CAGATTACAG CTTCAGGACA ATATGGACAG TGGGCCCCAA AGCTGGCCAG ACTTCATTAT
3541 TCCGGATCAA TCAATGCCTG GAGCACCAAG GAGCCCTTTT CTTGGATCAA GGTGGATCTG
3601 TTGGCACCAA TGATTATTCA CGGCATCAAG ACCCAGGGTG CCCGTCAGAA GTTCTCCAGC
3661 CTCTACATCT CTCAGTTTAT CATCATGTAT AGTCTTGATG GGAAGAAGTG GCAGACTTAT
3721 CGAGGAAATT CCACTGGAAC CTTAATGGTC TTCTTTGGCA ATGTGGATTC ATCTGGGATA
3781 AAACACAATA TTTTTAACCC TCCAATTATT GCTCGATACA TCCGTTTGCA CCCAACTCAT
3841 TATAGCATTC GCAGCACTCT TCGCATGGAG TTGATGGGCT GTGATTTAAA TAGTTGCAGC
3901 ATGCCATTGG GAATGGAGAG TAAAGCAATA TCAGATGCAC AGATTACTGC TTCATCCTAC
3961 TTTACCAATA TGTTTGCCAC CTGGTCTCCT TCAAAAGCTC GACTTCACCT CCAAGGGAGG
4021 AGTAATGCCT GGAGACCTCA GGTGAATAAT CCAAAAGAGT GGCTGCAAGT GGACTTCCAG

TABLE 1-continued

| Polynucleotide Sequences |
| --- |
| 4081 AAGACAATGA AAGTCACAGG AGTAACTACT CAGGGAGTAA AATCTCTGCT TACCAGCATG |
| 4141 TATGTGAAGG AGTTCCTCAT CTCCAGCAGT CAAGATGGCC ATCAGTGGAC TCTCTTTTTT |
| 4201 CAGAATGGCA AAGTAAAGGT TTTTCAGGGA AATCAAGACT CCTTCACACC TGTGGTGAAC |
| 4261 TCTCTAGACC CACCGTTACT GACTCGCTAC CTTCGAATTC ACCCCCAGAG TTGGGTGCAC |
| 4321 CAGATTGCCC TGAGGATGGA GGTTCTGGGC TGCGAGGCAC AGGACCTCTA C**GACAAAACT** |
| 4381 **CACACATGCC CACCGTGCCC AGCTCCAGAA CTCCTGGGCG GACCGTCAGT CTTCCTCTTC** |
| 4441 **CCCCCAAAAC CCAAGGACAC CCTCATGATC TCCCGGACCC CTGAGGTCAC ATGCGTGGTG** |
| 4501 **GTGGACGTGA GCCACGAAGA CCCTGAGGTC AAGTTCAACT GGTACGTGGA CGGCGTGGAG** |
| 4561 **GTGCATAATG CCAAGACAAA GCCGCGGGAG GAGCAGTACA ACAGCACGTA CCGTGTGGTC** |
| 4621 **AGCGTCCTCA CCGTCCTGCA CCAGGACTGG CTGAATGGCA AGGAGTACAA GTGCAAGGTC** |
| 4681 **TCCAACAAAG CCCTCCCAGC CCCCATCGAG AAAACCATCT CCAAAGCCAA AGGGCAGCCC** |
| 4741 **CGAGAACCAC AGGTGTACAC CCTGCCCCCA TCCCGGGATG AGCTGACCAA GAACCAGGTC** |
| 4801 **AGCCTGACCT GCCTGGTCAA AGGCTTCTAT CCCAGCGACA TCGCCGTGGA GTGGGAGAGC** |
| 4861 **AATGGGCAGC CGGAGAACAA CTACAAGACC ACGCCTCCCG TGTTGGACTC CGACGGCTCC** |
| 4921 **TTCTTCCTCT ACAGCAAGCT CACCGTGGAC AAGAGCAGGT GGCAGCAGGG GAACGTCTTC** |
| 4981 **TCATGCTCCG TGATGCATGA GGCTCTGCAC AACCACTACA CGCAGAAGAG CCTCTCCCTG** |
| 5041 **TCTCCGGGTA AATGA** |

TABLE 2

Polypeptide Sequences

A. B-Domain Deleted FVIII-Fc Monomer Hybrid (BDD FVIIIFc monomer dimer): created by coexpressing BDD FVIIIFc and Fc chains.

Construct = HC-LC-Fc fusion. An Fc expression cassette is cotransfected with BDDFVIII-Fc to generate the BDD FVIIIFc monomer-. For the BDD FVIIIFc chain, the Fc sequence is shown in bold; HC sequence is shown in double underline; remaining B domain sequence is shown in italics. Signal peptides are underlined.

i) B domain deleted FVIII-Fc chain (19 amino acid signal sequence underlined)

(SEQ ID NO: 2)

MQIELSTCFFLCLLRFCFSATRRYYLGAVELSWDYMQSDLGELPVDARFPPRVPKSFPFNTSVVYKKTLFV
EFTDHLFNIAKPRPPWMGLLGPTIQAEVYDTVVITLKNMASHPVSLHAVGVSYWKASEGAEYDDQTSQREK
EDDKVFPGGSHTYVWQVLKENGPMASDPLCLTYSYLSHVDLVKDLNSGLIGALLVCREGSLAKEKTQTLHK
FILLFAVFDEGKSWHSETKNSLMQDRDAASARAWPKMHTVNGYVNRSLPGLIGCHRKSVYWHVIGMGTTPE
VHSIFLEGHTFLVRNHRQASLEISPITFLTAQTLLMDLGQFLLFCHISSHQHDGMEAYVKVDSCPEEPQLR
MKNNEEAEDYDDDLTDSEMDVVRFDDDNSPSFIQIRSVAKKHPKTWVHYIAAEEEDWDYAPLVLAPDDRSY
KSQYLNNGPQRIGRKYKKVRFCANTDETFKTREAIQHESGILGPLLYGEVGDTLLIIFKNQASRPYNIYPH
GITDVRPLYSRRLPKGVKHLKDFPILPGEIFKYKWTVTVEDGPTKSDPRCLTRYYSSFVNMERDLASGLIG
PLLICYKESVDQRGNQIMSDKRNVILFSVFDENRSWYLTENIQRFLPNPAGVQLEDPEFQASNIMHSINGY
VFDSLQLSVCLHEVAYWYILSIGAQTDFLSVFFSGYTFKHKMVYEDTLTLFPFSGETVFMSMENPGLWILG
CHNSDFRNRGMTALLKVSSCDKNTGDYYEDSYEDISAYLLSKNNAIEPR*SFSQNPPVLKRHQR*EITRTTLQ
SDQEEIDYDDTISVEMKKEDFDIYDEDENQSPRSFQKKTRHYFIAAVERLWDYGMSSSPHVLRNRAQSGSV
PQFKKVVFQEFTDGSFTQPLYRGELNEHLGLLGPYIRAEVEDNIMVTFRNQASRPYSFYSSLISYEEDQRQ
GAEPRKNFVKPNETKTYFWKVQHHMAPTKDEFDCKAWAYFSDVDLEKDVHSGLIGPLLVCHTNTLNPAHGR
QVTVQEGALFFTIFDETKSWYFTENMERNCRAPCNIQMEDPTFKENYRFHAINGYIMDTLPGLVMAQDQRI
RWYLLSMGSNENIHSIHFSGHVFTVRKKEEYKMALYNLYPGVFETVEMLPSKAGIWRVECLIGEHLHAGMS
TLFLVYSNKCQTPLGMASGHIRDFQITASGQYGQWAPKLARLHYSGSINAWSTKEPFSWIKVDLLAPMIIH
GIKTQGARQKFSSLYISQFIIMYSLDGKKWQTYRGNSTGTLMVFFGNVDSSGIKHNIFNPPIIARYIRLHP
THYSIRSTLRMELMGCDLNSCSMPLGMESKAISDAQITASSYFTNMFATWSPSKARLHLQGRSNAWRPQVN
NPKEWLQVDFQKTMKVTGVTTQGVKSLLTSMYVKEFLISSSQDGHQWTLFFQNGKVKVFQGNQDSFTPVVN
SLDPPLLTRYLRIHPQSWVHQIALRMEVLGCEAQDLYDKTHTCPPCPAPELLGGPSVFLFPPKPKDTLMIS
RTPEVTCVVVDVSHEDPEVKFNWYVDGVGVHANKTKPREEQYNSTYRVVSVLTVLHQDWLNGKEYKCKVSN
KALPAPIEKTISKAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK ii) Fc chain (20 amino acid heterologous signal peptide from mouce Igκ chain underlined)

(SEQ ID NO: 4)

METDTLLLWVLLLWVPGSTGDKTHTCPPCPAPELLGGPSVFLFPPKPKDTLMISRTPEVTCVVVDVSHEDP
EVKFNWYVDGVEVHANKTKPREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTPPVLDSDGSFFLYSKLTVD
KSRWQQGNVFSCSVMHEALHNHYTQKSLSLSPGK

TABLE 2-continued

Polypeptide Sequences

B. Full length FVIIIFc monomer hybrid (Full length FVIIIFc monomer dimer): created by coexpressing FVIIIFc and Fc chains.

Construct = HC-B-LC-Fc fusion. An Fc expression cassette is cotransfected with full length FVIII-Fc to generate the full length FVIIIFc monomer. For the FVIIIFc chain, the Fc sequence is shown in bold; HC sequence is shown in double underline; B domain sequence is shown in italics. Signal peptides are underlined.

i) Full length FVIIIFc chain (FVIII signal peptide underlined (SEQ ID NO: 6)

MQIELSTCFFLCLLRFCFSATRRYYLGAVELSWDYMQSDLGELPVDARFPPRVPKSFPFNTSVVYKKTLFV
EFTDHLFNIAKPRPPWGGLLGPTIQAEVYDTVVITLKNMASHPVSLHAVGVSYWKASEGAEYDDQTSQREK
EDDKVFPGGSHTYVWQVLKENGPMASDPLCLTYSYLSHVDLVKDLNSGLIGALLVCREGSLAKEKTQTLHK
FILLFAVFDEGKSWHSETKNSLMQDRDAASARAWPKMHTVNGYVNRSLPGLIGCHRKSVYWHVIGMGTTPE
VHSIFLEGHTFLVRNHRQASLEISPITFLTAQTLLMDLGQFLLFCHISSHQHDGMEAYVKVDSCPEEPQLR
MKNNEEAEDYDDDLTDSEMDVVRFDDDNSPSFIQIRSVAKKHPKTWVHYIAAEEEDWDYAPLVLAPDDRSY
KSQYLNNGPQRIGRKYKKVRFCANTDETFKTREAIQHESGILGPLLYGEVGDTLLIIFKNQASRPYNIYPH
GITDVRPLYSRRLPKGVKHLKDFPILPGEIFKYKWTVTVEDGPTKSDPRCLTRYYSSFVNMERDLASGLIG
PLLICYKESVDQRGNQIMSDKRNVILFSVFDENRSWYLTENIQRFLPNPAGVQLEDPEFQASNIMHSINGY
VFDSLQLSVCLHEVAYWYILSIGAQTDFLSVFFSGYTFKHKMVYEDTLTLFPFSGETVFMSMENPGLWILG
CHNSDFRNRGMTALLKVSSCDKNTGDYYEDSYEDISAYLLSKNNAIEPR*SFSQNSRHPSTRQKQFNATTIP*
*ENDIEKTDPWFAHRTPMPKIQNVSSSDLLMLLRQSPTPHGLSLSDLQEAKYETFSDDPSPGAIDSNNSLSE*
*MTHFRPQLHHSGDMVFTPESGLQLRLNEKLGTTAATELKKLDFKVSSTSNNLISTIPSDNLAAGTDNTSSL*
*GPPSMPVHYDSQLDTTLFGKKSSPLTESGGPLSLSEENNDSKLLESGLMNSQESSWGKNVSSTESGRLFKG*
*KRAHGPALLTKDNALFKVSISLLKTNKTSNNSATNRKTHIDGPSLLIENSPSVWQNILESDTEFKKVTPLI*
*HDRMLMDKNATALRLNHMSNKTTSSKNMEMVQQKKEGPIPPDAQNPDMSFFKMLFLPESARWIQRTHGKNS*
*LNSGQGPSPKQLVLSGPEKSVEGQNFLSEKNKVVVGKGEFTKDVGLKEMVFPSSRNLFLTNLDNLHENNTH*
*NQEKKIQEEIEKKETLIQENVVLPQIHTVTGTKNFMKNLFLLSTRQNVEGSYDGAYAPVLQDFTSLNDSTN*
*RTKKHTAHFSKKGEEENLEGLGNQTKQIVEKYACTTRISPNTSQQNFVTQRSKRALKQFRLPLEETELEKR*
*IIVDDTSTQWSKNMKHLTPSTLTQIDYNEKEKGAITQSPLSDCLTRSHSIPQANRSPLPIAKVSSFPSIRP*
*IYLTRVLFQDNSSHLPAASYRKKDSGVQESSHFLQGAKKNNLSLAILTLEMTGDQREVGSLGTSATNSVTY*
*KKVENTVLPKPDLPKTSGKVELLPKVHIYQKDLFPTETSNGSPGHLDLVEGSLLQGTEGAIKWNEANRPGK*
*VPFLRVATESSAKTPSKLLDPLAWDNHYGTQIPKEEWKSQEKSPEKTAFKKKDTILSLNACESNHAIAAIN*
*EGQNKPEIEVTWAKGQRTERLCSQNPPVLKRHQR*EITRTTLQSDQEEIDYDDTISVEMKKEDFDIYDEDEN
QSPRSFQKKTRHYFIAAVETLWDYGMSSSPHVLRNRAQSGSVPQFKKVVFQEFTDGSFTQPLYRGELNEHL
GLLGPYIRAEVEDNIMVTFRNQASRPYSFYSSLISYEEDQRQGAEPRKNFVKPNETKTYFWKVQHHMAPTK
DEFDCKAWAYFSDVDLEKDVHSGLIGPLLVCHTNTLNPAHGRQVTVQEFALFFTIFDETKSWYFTENMERN
CRAPCNIQMEDPTFKENYRFHAINGYIMDTLPGLVMAQDQRIRWYLLSMGSNENIHSIHFSGHVFTVRKKE
EYKMALYNLYPGVFETVEMLPSKAGIWRVECLIGEHLHAGMSTLFLVYSNKCQTPLGMASGHIRDFQITAS
GQYGQWAPKLARLHYSGSINAWSTKEPFSWIKVDLLAPMIIHGIKTQGARQKFSSLYISQFIIMYSLDGKK
WQTYRGNSTGTLMVFFGNVDSSGIKHNIFNPPIIARYIRLHPTHYSIRSTLRMELMGCDLNSCSMPLGMES
KAISDAQITASSYFTNMFATWSPSKARLHLQGRSNAWRPQVNNPKEWLQVDFQKTMKVTGVTTQGVKSLLT
SMYVKEFLISSSQDGHQWTLFFQNGKVKVFQGNQDSFTPVVNSLDPPLLTRYLRIHPQSWVHQIALRMEVL
GCEAQDLYDKTHTCPPCPAPELLGGPSVFLFPPKPKDTLMISRTPEVTCVVVDVSHEDPEVKFNWYVDGVE
VHANKTKPREEQYNSTYRVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSGGLYSKLTVDKSRWQQGNVFSC
SVMHEALHNHYTQKSLSLSPGK ii) Fc chain (20 amino acid heterologous signal peptide from mouse Igκ chain underlined)

(SEQ ID NO: 4)

METDTLLLWVLLLWVPGSTGDKTHTCPPCPAPELLGGPSVFLFPPKPKDTLMISRTPEVTCVVVDVSHEDP
EVKFNWYVDGVEVHANKTKPREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTPPVLDSDGSGGLYSKLTVD
KSRWQQGNVFSCSVMHEALHNHYTQKSLSLSPGK

C. Single Chain BBD rFVIIIFc Polypeptide (i) Single Chain (SC) B-Domain Deleted rFVIIIFc Chain amino acid sequence (FVIII signal peptide underlined, HC double underlined, remaining B domain in italics with R1645A/R1648A bold and underlined, Fc region in bold).

(SEQ ID NO: 8)

1 MQIELSTCFF LCLLRFCFSA TRRYYLGAVE LSWDYMQSDL GELPVDARFP PRVPKSFPFN
61 TSVVYKKTLF VEFTDHLFNI AKPRPPWMGL LGPTIQAEVY DTVVITLKNM ASHPVSLHAV
121 GVSYWKASEG AEYDDQTSQR EKEDDKVFPG GSHTYVWQVL KENGPMASDP LCLTYSYLSH
181 VDLVKDLNSG LIGALLVCRE GSLAKEKTQT LHKFILLFAV FDEGKSWHSE TKNSLMQDRD
241 AASARAWPKN HTVNGYVNRS LPGLIGCHRK SVYWHVIGMG TTPEVHSIFL EGHTFLVRNH
301 RQASLEISPI TFLTAQTLLM DLGQFLLFCH ISSHQHDGME AYVKVDSCPE EPQLRMKNNE
361 EAEDYDDDLT DSEMDVVRFD DDNSPSFIQI RSVAKKHPKT WVHYIAAEEE DWDYAPLVLA
421 PDDRSYKSQY LNNGPQRIGR KYKKVRFCAN TDETFKTREA IQHESGILGP LLYGEVGDTL
481 LIIPKNQASR PYNIYPHGIT DVRPLYSRRL PKGVKHLKDF PILPGEIFKY KWTVTVEDGP
541 TKSDPRCLTR YYSSFVNMER DLASGLIGPL LICYKESVDQ RGNQIMSDKR NVILFSVFDE
601 NRSWYLTENI QRFLPNPAGV QLEDPEFQAS NIMHSINGYV FSDLQLSVCL HEVAYWYILS
661 IGAQTDFLSV FFSGYTFKHK MVYEDTLTLF PFSGETVFMS MENPGLWILG CHNSDFRNRG
721 MTALLKVSSC DKNTGDYYED SYEDISAYLL SKNNAIEPR*S FSQNPPVLK*A *HQ*AEITRTTL
781 QSDQEEIDYD DTISVEMKKE DFDIYDEDEN QSPRSFQKKT RHYFIAAVER LWDYGMSSSP

TABLE 2-continued

| Polypeptide Sequences |
|---|
| 841 HVLRNRAQSG SVPQFKKVVF QEFTDGSFTQ PLYRGELNEH LGLLGPYIRA EVEDNIMVTF |
| 901 RNQASRPYSF YSSLISYEED QRQGAEPRKN FVKPNETKTY FWKVQHHMAP TKDEFDCKAW |
| 961 AYFSDVDLEK DVHSGLIGPL LVCHTNTLNP AHGRQVTVQE FALFFTIFDE TKSWYFTENM |
| 1021 ERNCRAPCNI QMEDPTFKEN YRFHAINGYI MDTLPGLVMA QDQRIRWYLL SMGSNENIHS |
| 1081 IHFSGHVFTV RKKEEYKMAL YNLYPGVFET VEMLPSKAGI WRVECLIGEH LHAGMSTLFL |
| 1141 VYSNKCQTPL GMASGHIRDF QITASGQYGQ WAPKLARLHY SGSINAWSTK EPFSWIKVDL |
| 1201 LAPMIIHGIK TQGARQKFSS LIYSQFIIMY SLDGKKWQTY RGNSTGTLMV FFGNVDSSGI |
| 1261 KHNIFNPPII ARYIRLHPTH YSIRSTLRME LMGCDLNSCS MPLGMESKAI SDAQITASSY |
| 1321 FTNMFATWSP SKARLHLQGR SWAWRPQVNN PKEWLQVDFQ KTMKVTGVTT QGVKSLLTSM |
| 1381 YVKEFLISSS QDGHQWTLFF QNGKVKVFQG NQDSFTPVVN SLDPPLLTRY LRIHPQSWVH |
| 1441 QIALRMEVLG CEAQDLY**DKT HTCPPCPAPE LLGGPSVFLF PPKPKDTLMI STRPEVTCVV** |
| 1501 **VDVSHEDPEV KFNWYVDGVE VHNAKTKPRE EQYNSTYRVV SVLTVLHQDW LNGKEYKCKV** |
| 1561 **SNKALPAPIE KTIAKAKGQP REPQVYTLPP SRDELTKNQV SLTCLVKGFY PSDIAVEWES** |
| 1621 **NGQPRNNYKT TPPVLDSDGS FFLYSKLTVD KSRWQQGNVF SCSVMHEALH NHYTQKSLSL** |
| 1681 **SPGK** |

What is claimed is:

1. An isolated cell line comprising a recombinant vector encoding a single chain FVIII polypeptide, wherein the single chain FVIII polypeptide comprises residues 20 to 1457 of SEQ ID NO: 8.

2. The cell line of claim 1, wherein the single chain FVIII polypeptide further comprises a heterologous moiety.

3. A polynucleotide encoding the single chain FVIII polypeptide of claim 1.

4. A vector comprising the polynucleotide of claim 3.

5. The cell line of claim 1, wherein the cell line is a mammalian cell line.

6. The cell line of claim 2, wherein the heterologous moiety is a half-life extending moiety.

7. The cell line of claim 6, wherein the half-life extending moiety is an immunoglobulin constant region or a portion thereof, albumin, albumin binding polypeptide, PAS, the C-terminal peptide (CTP) of the β subunit of human chorionic gonadotropin, polyethylene glycol (PEG), hydroxyethyl starch (HES), albumin-binding small molecules, or combinations thereof.

8. The cell line of claim 1, wherein the cell line further comprises a polynucleotide specific for a FVIII polypeptide processing enzyme.

9. The cell line of claim 1, wherein the single chain FVIII polypeptide further comprises an immunoglobulin constant region or a portion thereof.

10. The cell line of claim 1, wherein the single chain FVIII polypeptide further comprises albumin.

11. A polynucleotide encoding the single chain FVIII polypeptide and the half-life extending moiety of claim 6.

12. A vector comprising the polynucleotide of claim 11.

13. A polynucleotide encoding the single chain FVIII polypeptide and the immunoglobulin constant region or a portion thereof of claim 9.

14. A vector comprising the polynucleotide of claim 13.

15. An isolated cell line comprising a recombinant vector encoding the amino acid sequence as set forth in SEQ ID NO: 8.

16. A vector encoding the amino acid sequence as set forth in SEQ ID NO: 8.

17. A method for producing a single chain FVIII polypeptide comprising culturing the cell line of claim 1 under conditions sufficient for production of the single chain FVIII polypeptide.

* * * * *